(12) United States Patent
Yoon et al.

(10) Patent No.: US 9,402,873 B2
(45) Date of Patent: Aug. 2, 2016

(54) **METHOD FOR PREVENTING AND TREATING *SALMONELLA* TYPHIMURIUM INFECTION**

(75) Inventors: Seong Jun Yoon, Seoul (KR); Soo Youn Jun, Seoul (KR); Hyoun Rok Paik, Jeollanam-do (KR); Dong Hwan Kim, Kyeonggi-do (KR); Sang Hyeon Kang, Seoul (KR)

(73) Assignee: Intron Biotechnology, Inc., Kyeonggi-do (KR)

( * ) Notice: Subject to any disclaimer, the term of this patent is extended or adjusted under 35 U.S.C. 154(b) by 79 days.

(21) Appl. No.: 14/343,926

(22) PCT Filed: Sep. 9, 2011

(86) PCT No.: PCT/KR2011/006728
§ 371 (c)(1),
(2), (4) Date: Aug. 25, 2014

(87) PCT Pub. No.: WO2013/035906
PCT Pub. Date: Mar. 14, 2013

(65) Prior Publication Data
US 2014/0363401 A1    Dec. 11, 2014

(30) Foreign Application Priority Data
Sep. 9, 2011    (KR) .................. 10-2011-0091699

(51) Int. Cl.
*A61K 39/112*    (2006.01)
*A61K 35/76*    (2015.01)
*A61K 38/16*    (2006.01)

(52) U.S. Cl.
CPC .............. *A61K 35/76* (2013.01); *A23K 10/16* (2016.05); *A61K 38/162* (2013.01)

(58) Field of Classification Search
None
See application file for complete search history.

(56) References Cited

U.S. PATENT DOCUMENTS

| 7,935,355 | B2 * | 5/2011 | Sotomayor | A61K 39/0275 424/184.1 |
| 7,988,978 | B2 * | 8/2011 | Sotomayor | A61K 39/0208 424/203.1 |
| 8,771,936 | B2 * | 7/2014 | Kang | A61K 35/76 424/93.6 |
| 8,846,368 | B2 * | 9/2014 | Shin | C12N 7/00 435/235.1 |
| 9,211,309 | B2 * | 12/2015 | Yoon | A61K 35/76 |
| 2010/0135962 | A1 * | 6/2010 | Kang | C07K 14/005 424/93.6 |
| 2010/0166709 | A1 * | 7/2010 | Kang | C12N 7/00 424/93.6 |
| 2010/0247567 | A1 * | 9/2010 | Sotomayor | A61K 39/0208 424/203.1 |
| 2013/0011369 | A1 * | 1/2013 | Yoon | C12N 7/00 424/93.6 |
| 2013/0022579 | A1 * | 1/2013 | Kang | A61K 35/76 424/93.6 |
| 2014/0017205 | A1 * | 1/2014 | Shin | C12N 7/00 424/93.6 |
| 2014/0348799 | A1 * | 11/2014 | Yang | A61K 35/76 424/93.6 |
| 2014/0363401 | A1 * | 12/2014 | Yoon | A61K 38/162 424/93.6 |
| 2016/0053234 | A1 * | 2/2016 | Yoon | C12N 7/00 435/235.1 |

FOREIGN PATENT DOCUMENTS

| KR | 100941891 | 2/2010 |
| KR | 100941892 | 2/2010 |
| KR | 1020100075262 | 7/2010 |
| WO | 2010034479 | 4/2010 |
| WO | WO 2013/035906 A1 * | 3/2013 |

OTHER PUBLICATIONS

Parks et al, Appl. Environ. Microbiol. 2012, 78/1:58-69.*

* cited by examiner

*Primary Examiner* — Nita M Minnifield
(74) *Attorney, Agent, or Firm* — Meunier Carlin & Curfman LLC

(57) ABSTRACT

The present invention relates to a composition comprising STP-1, a bacteriophage isolated from nature, capable of infecting *Salmonella Typhimurium* so as to kill the same as an active ingredient, and a method for preventing and treating *Salmonella Typhimurium* infection using the said composition. According to the present invention, the bacteriophage STP-1, an active ingredient of the composition, has a killing activity against *Salmonella Typhimurium* and has the genome represented by SEQ. ID. NO: 1.

2 Claims, 2 Drawing Sheets

METHOD FOR PREVENTING AND TREATING *SALMONELLA* TYPHIMURIUM INFECTION

BACKGROUND OF THE INVENTION

1. Field of the Invention

The present invention relates to a composition usable for preventing or treating *Salmonella Typhimurium* infection comprising a bacteriophage, isolated from nature and capable of infecting *Salmonella Typhimurium* so as to kill the same as an active ingredient, and a method for preventing and treating *Salmonella Typhimurium* infection by using the said composition. More precisely, the present invention relates to a bacteriophage isolated from nature which is characterized by having the genome represented by SEQ. ID. NO: 1 and is capable of killing *Salmonella Typhimurium* specifically, a composition usable for preventing and treating *Salmonella Typhimurium* infection comprising the said bacteriophage as an active ingredient, and a method for preventing and treating *Salmonella Typhimurium* infection by using the said composition.

2. Description of the Related Art

*Salmonella* is similar to *E. coli* in the aspects of morphology or physiology but is categorized in an independent genus for the convenience in clinical use by the proposal of K. Kauffmann et al. *Salmonella* has been isolated from enteritis and gastroenteritis patients and from animals with diverse diseases since *Salmonella* Choleraesuis was first isolated from a pig died of hog cholera by Salmon and Smith in 1885. *Salmonella* has also been isolated from healthy animals such as chicken, cow, pig, goat, dog, and cat and from our environment.

More than 2,000 serotypes of *Salmonella* have been reported so far and it can be largely divided into two groups, one of which is the group that has host specificity and the other of which is the group that does not have host specificity. *Salmonella* is Gram-negative bacilli and spore is not formed. It is a parasite living in a variety of animals.

*Salmonella* infection is generally called salmonellosis, which carries the symptoms of rough skin, anorexia, conjunctivitis, depression, loose feces, splenomegaly, and even death. The most frequently found *Salmonella* in pig industry is *Salmonella Typhimurium*. The loss and damage caused by *Salmonella Typhimurium* infection in livestock industry, particularly in pig industry, is huge. Therefore, it is urgently requested to develop a novel method to prevent and treat *Salmonella* infection efficiently.

The utilization of bacteriophage is now highly drawing our attention as an effective way of treating bacterial disease. In particular, our interests in bacteriophage grow with the preference of nature-friendly method. Bacteriophage is an extremely small microorganism infecting bacteria, which is generally called phage in short. Bacteriophage replicates within bacteria after infection. Upon completion of the multiplication, offspring bacteriophages are coming out of the host cells with destroying the host bacteria. The infection of bacteriophage in bacteria is very unique and specific, so only specific bacteria can be infected with a specific bacteriophage. That is, there is a limitation in bacteria that can be infected with bacteriophage. Thus, bacteriophage can only kill specific target bacteria without affecting any other bacteria.

Bacteriophage was first found in 1915 when English bacteriologist Twort was studying on the phenomenon that *micrococcus* colony was being melted clearly by some reasons. And also, French bacteriologist d'Herelle noticed that *Shigella disentriae* was melted by something in filtrate of dysentery patient's feces and afterwards he discovered bacteriophage independently by the following study and named it bacteriophage which meant 'eating bacteria'. Since then, bacteriophages corresponding to different pathogenic bacteria including *Shigella, Salmonella* and *Vibrio cholerae* have been continuously reported.

Owing to its capability of killing bacteria, bacteriophage has been in the center of our interest to fight with bacterial infection and studies followed thereon. However, since Flemming found out penicillin, antibiotics have been supplied and the study on bacteriophage has been limited in some east European countries and old Soviet Union. It was not until 2000 that the conventional antibiotics demonstrated their problems in use because of increasing antibiotic-resistant bacteria. So, once again, bacteriophage draws out attention as an alternative anti-bacterial agent that can take the place of the conventional antibiotics.

The present inventors have tried to develop a composition usable for preventing or treating *Salmonella Typhimurium* infection by using a bacteriophage isolated from nature and capable of killing *Salmonella Typhimurium* selectively and tried further to establish a method to prevent or treat *Salmonella Typhimurium* infection by using the said composition. As a result, the present inventors succeeded in isolation of a proper bacteriophage from nature and obtainment of a sequence of the genome distinguishing the phage from others, leading to the completion of the present invention by confirming that the composition developed by the inventors could be effectively used for the prevention and treatment of *Salmonella Typhimurium* infection.

SUMMARY OF THE INVENTION

It is an object of the present invention to provide a novel bacteriophage capable of killing *Salmonella Typhimurium* selectively.

It is another object of the present invention to provide a composition usable for prevention of *Salmonella Typhimurium* infection comprising the said bacteriophage as an active ingredient which is capable of killing *Salmonella Typhimurium* selectively by infecting *Salmonella Typhimurium* and to provide a method for prevention of *Salmonella Typhimurium* infection using the same.

It is also an object of the present invention to provide a composition usable for treatment of *Salmonella Typhimurium* infection comprising the said bacteriophage as an active ingredient which is capable of killing *Salmonella Typhimurium* selectively by infecting *Salmonella Typhimurium* and to provide a method for treatment of *Salmonella Typhimurium* infection using the same.

It is further an object of the present invention to provide a disinfectant for the prevention and treatment of *Salmonella Typhimurium* infection using the said composition.

It is also an object of the present invention to provide a water additive for the prevention and treatment of *Salmonella Typhimurium* infection using the said composition.

It is also an object of the present invention to provide a feed additive for the prevention and treatment of *Salmonella Typhimurium* infection using the said composition.

To achieve the above objects, the present invention provides a composition comprising a bacteriophage as an active ingredient which is capable of destroying *Salmonella Typhimurium* by infecting *Salmonella Typhimurium*, and a method for preventing and treating *Salmonella Typhimurium* infection by using the said composition.

The present invention also provides a disinfectant, a water additive, and a feed additive that can be used for the prevention or treatment of *Salmonella Typhimurium* infection.

Advantageous Effect

As explained hereinbefore, the composition of the present invention and the method for preventing and treating *Salmonella Typhimurium* infection using the same have an advantage of high specificity against *Salmonella Typhimurium*, compared with other conventional chemical compositions and methods using thereof. That is, this composition does not have any effect on other useful resident flora and can be used only for the purpose of prevention and treatment of *Salmonella Typhimurium* infection. Thus, side effects are hardly accompanied. In general, when other chemicals such as the conventional antibiotics are used, general resident bacteria are also damaged, resulting in the decrease of immunity in animals and bringing other side effects. In the meantime, the present invention provides an advantage of nature-friendly effect by using the composition containing natural bacteriophage as an active ingredient.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
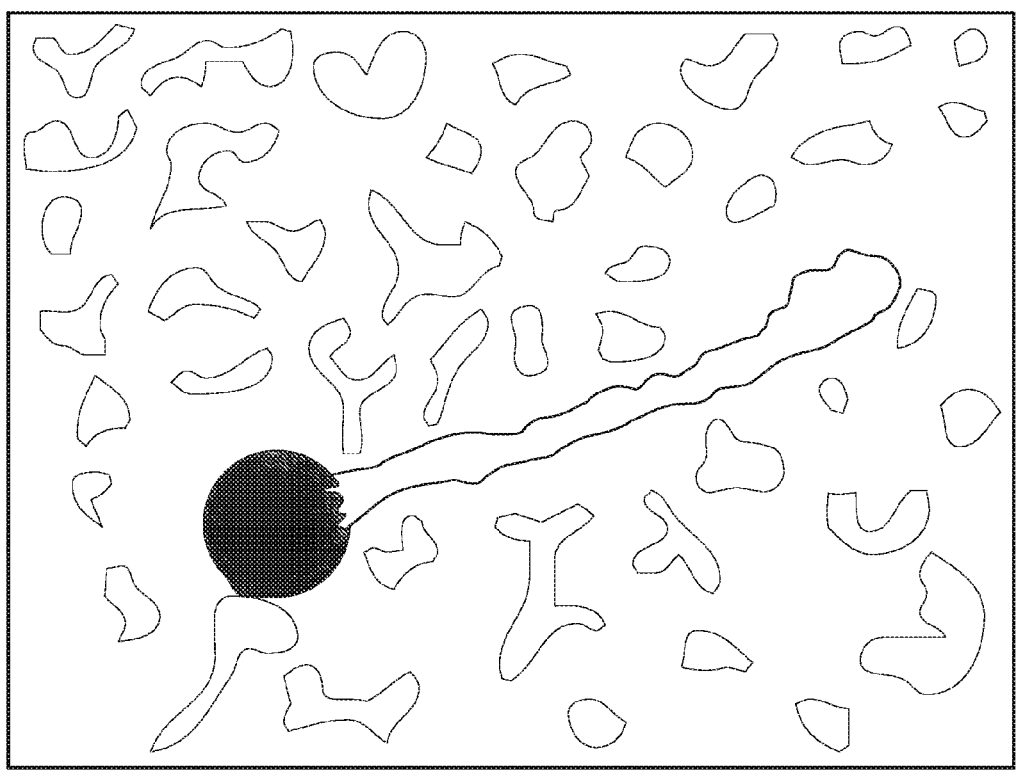
FIG. 1 is an electron micrograph showing the bacteriophage STP-1.

Hereinafter, the present invention is described in detail.

The present invention provides a composition comprising the bacteriophage isolated from nature and characterized by having the ability to infect *Salmonella Typhimurium* so as to kill the same, and a method for preventing and treating *Salmonella Typhimurium* infection using the said composition.

The bacteriophage used as the active ingredient in the composition of the present invention is the bacteriophage STP-1 having DNA represented by SEQ. ID. NO: 1 as its genome. The bacteriophage STP-1 was isolated by the present inventors and deposited at Korean Collection for Type Cultures, Korea Research Institute of Bioscience and Biotechnology on Sep. 5, 2011 (Accession No: KCTC 12012BP).

The present invention also provides a disinfectant, a water additive, and a feed additive that can be used for the prevention or treatment of *Salmonella Typhimurium* infection.

The bacteriophage STP-1 included in the composition of the present invention is capable of killing *Salmonella Typhimurium* efficiently, suggesting that the bacteriophage is effective in prevention or treatment of salmonellosis caused by *Salmonella Typhimurium*. Therefore, the composition of the present invention is useful for the prevention and treatment of salmonellosis caused by *Salmonella Typhimurium*. The term "salmonellosis" in this invention generally indicates all the symptoms caused by *Salmonella* infection including fever, headache, diarrhea, vomiting, etc.

The term "treat" or "treatment" in this description indicates (i) to suppress salmonellosis caused by *Salmonella Typhimurium*; and (ii) to relieve salmonellosis caused by *Salmonella Typhimurium*.

In this invention, the term "isolation" or "isolated" indicates the separation of bacteriophage from nature by using diverse experimental techniques and the process confirming the characteristics of the bacteriophage that can distinguish the bacteriophage itself from others. This term further includes the course of proliferating the bacteriophage by using biotechnology in order to make it a useful form.

The bacteriophage of the present invention includes the bacteriophage STP-1 and its variants as well. In this invention, "variants" indicate those bacteriophages which have the same genotypic/genotypic characteristics as the bacteriophage STP-1 even though there is minor variation in genomic sequencer or polypeptide encoding genetic information. Needless to say, the variants herein include polymorphic variants, too. It is preferred for those variants to have the same or equivalent biological function to the bacteriophage STP-1.

The composition of the present invention can include pharmaceutically acceptable carriers such as lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil, but not always limited thereto. The composition of the present invention can additionally include lubricants, wetting agents, sweetening agents, flavors, emulsifiers, suspensions and preservatives.

The composition of the present invention contains the bacteriophage STP-1 or the variants thereof as an active ingredient. At this time, the bacteriophage STP-1 or the variants thereof are included at the concentration of $1 \times 10^1$ pfu/ml~$1 \times 10^{30}$ pfu/ml or $1 \times 10^1$ pfu/g~$1 \times 10^{30}$ pfu/g, and more preferably at the concentration of $1 \times 10^4$ pfu/ml~$1 \times 10^{15}$ pfu/ml or $1 \times 10^4$ pfu/g~$1 \times 10^{15}$ pfu/g.

The composition of the present invention can be formulated by the method that can be performed by those in the art by using a pharmaceutically acceptable carrier and/or excipient in the form of unit dose or in multi-dose containers. The formulation can be in the form of solution, suspension, or emulsion in oil or water-soluble medium, extract, powder, granule, tablet or capsule. At this time, a dispersing agent or a stabilizer can be additionally included.

The composition of the present invention can be produced in the form of a disinfectant, a water additive, and a feed additive, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Isolation of Bacteriophage that can Destroy *Salmonella Typhimurium*

A bacteriophage capable of killing *Salmonella Typhimurium* was isolated from nature or from animal samples. *Salmonella Typhimurium* used for the isolation was *Salmonella Typhimurium* ST2, which was isolated previously by the present inventors and then identified as *Salmonella Typhimurium* by the inventors.

Collected samples were loaded in TSB (Tryptic Soy Broth) medium (casein digest, 17 g/L; soybean digest, 3 g/L; dextrose, 2.5 g/L; NaCl, 5 g/L; dipotassium phosphate, 2.5 g/L) inoculated with *Salmonella Typhimurium* (1/1000), followed by shaking culture for 3~4 hours at 37° C. Upon completion of the culture, centrifugation was performed at 8,000 rpm for 20 minutes and the supernatant was recovered. *Salmonella Typhimurium* was inoculated in the recovered supernatant (1/1000), followed by shaking culture for 3~4 hours at 37° C. This procedure was repeated 5 times in total in order to increase bacteriophage titer if bacteriophage was included in the sample. After repeating the process 5 times, the culture solution proceeded to centrifugation at 8,000 rpm for 20 minutes. Then, the supernatant was filtered using 0.45 μm filter. The obtained filtrate was investigated by using general spot overlay assay to see whether bacteriophage that could kill *Salmonella Typhimurium* was included.

Spot overlay assay was performed as follows. *Salmonella Typhimurium* was inoculated in TSB medium (1/1000), followed by shaking culture at 37° C. overnight. Then, 3 ml of the obtained *Salmonella Typhimurium* culture solution ($OD_{600}$: 2.0) was spread on TSA (Tryptic Soy Agar) plate medium (casein digest, 15 g/L; soybean digest, 5 g/L; NaCl, 5 g/L; agar, 15 g/L). The plate medium stayed on clean bench for about 30 minutes to let the spread solution is dried. After drying, 10 μl of the prepared filtrate was spotted on the plate whereon *Salmonella Typhimurium* was spread, which was dried as it was for 30 minutes. After drying, the plate was incubated at 37° C. for a day. It was then examined whether the clear zone was formed on the spot where the filtrate was spotted. If the clear zone was formed thereon, it suggested that the bacteriophage that could kill *Salmonella Typhimurium* was included therein. According to this procedure, the filtrate containing the bacteriophage that could destroy *Salmonella Typhimurium* could be obtained.

Pure bacteriophage was isolated from the filtrate confirmed to contain the bacteriophage capable of killing *Salmonella Typhimurium*. The isolation of pure bacteriophage was performed by plaque assay. More precisely, one of plaques formed from plaque assay was recovered by using a sterilized tip, which was then added to *Salmonella Typhimurium* culture solution, followed by culture for 4~5 hours. Upon completion of the culture, centrifugation was performed at 8,000 rpm for 20 minutes to obtain supernatant. *Salmonella Typhimurium* culture solution was added to the obtained supernatant at the ratio of 1:50, followed by further culture for 4~5 hours. To increase the number of bacteriophage, this procedure was repeated at least 5 times and then centrifugation was performed at 8,000 for 20 minutes to obtain supernatant. Plaque assay was performed with the supernatant. Generally, the pure bacteriophage isolation cannot be accomplished simply by performing the above procedure once. Thus, the previous steps were repeated again using one of plaques formed from plaque assay. After repeating the procedure at least 5 times, the solution comprising pure bacteriophage was obtained. The repetition of this pure bacteriophage isolation processes was not finished until the sizes and shapes of plaques were all similar. The pure bacteriophage isolation was confirmed at last by the observation under electron microscope. If pure bacteriophage was not confirmed, the above processes were repeated again. Observation under electron microscope was performed by the conventional method, which was as follows: copper grid was soaked in the solution containing pure bacteriophage, followed by negative staining with 2% uranyl acetate and drying thereof; and morphology was observed by taking pictures with transmission electron microscope.

The solution containing pure bacteriophage was purified as follows. *Salmonella Typhimurium* culture solution was added to the pure bacteriophage solution at the ratio of 1:50, followed by culture for 4~5 hours. Upon completion of the culture, centrifugation was performed at 8,000 rpm for 20 minutes to obtain supernatant. To obtain enough amount of bacteriophage, the said process was repeated 5 times in total. The final supernatant was filtered with 0.45 μm filter, followed by precipitation by using polyethylene glycol (PEG). Particularly, PEG and NaCl were added to 100 ml of the filtrate (10% PEG 8000/0.5 M NaCl), which stood at room temperature for 2~3 hours. Then, centrifugation was performed at 8,000 rpm for 30 minutes to obtain bacteriophage precipitate. The obtained bacteriophage precipitate was suspended in 5 ml of buffer (10 mM Tris-HCl, 10 mM $MgSO_4$, 0.1% Gelatin, pH 8.0). This solution was called bacteriophage suspension or bacteriophage solution.

At last, purified pure bacteriophage was obtained and this bacteriophage was named bacteriophage STP-1, which was then deposited at Korean Collection for Type Cultures, Korea Research Institute of Bioscience and Biotechnology on Sep. 5, 2011 (Accession No: KCTC 12012BP). The electron micrograph of bacteriophage STP-1 is presented in FIG. 1.

Example 2

Extraction of Bacteriophage STP-1 Genome and Sequencing Thereof

Bacteriophage STP-1 genome was extracted as follows using the bacteriophage suspension obtained in Example 1. To eliminate *Salmonella Typhimurium* DNA and RNA which might be included in the suspension, DNase I and RNase A were added to 10 and of the bacteriophage suspension (200 U each), which stood at 37° C. for 30 minutes. 30 minutes later, to neutralize DNase I and RNase A activity, 500 μl of 0.5 M ethylenediaminetetraacetic acid (EDTA) was added, which stood for 10 minutes. The solution stood at 65° C. for another 10 minutes, then 100 μl of proteinase K (20 mg/ml) was added, followed by incubation at 37° C. for 20 minutes to break the outer wall of the bacteriophage. Then, 500 μl of 10% sodium dodecyl sulfate (SDS) solution was added thereto, followed by incubation at 65° C. for one hour. One hour later, 10 ml and of the mixed solution comprising phenol chloroform:isoamylalcohol at the volumetric ratio of 25:24:1 was added thereto and the solution was well mixed. Centrifugation was performed at 13,000 rpm for 15 minutes to separate layers, among which the upper most layer was obtained. Isopropyl alcohol was added to the obtained layer at the volume ratio of 1.5, followed by centrifugation at 13,000 rpm for 10 minutes to precipitate genome. The precipitate was recovered, to which 70% ethanol was added, followed by centrifugation at 13,000 rpm for 10 minutes. The washed precipitate was collected and vacuum-dried, which was then dissolved in 100 μl of water. Genome of the bacteriophage STP-1 was obtained by repeating the above processes.

The genomic sequence of the bacteriophage STP-1 was analyzed with the obtained genome at National Instrumentation Center for Environmental Management, Seoul National University, by using shotgun library construction. Particularly, the bacteriophage genome was cut by random shearing technique using Nebulizer to obtain DNA fragments (1~6 kbp), which proceeded to end-repairing. The repaired DNA proceeded to electrophoresis on agarose gel. Then, gDNA fragments (inserts) in 3~5 kbp were obtained. The obtained DNA fragments of the bacteriophage genome were inserted in pC31 vector by using T4 ligase (ligation) to establish library. The recombinant plasmid introduced with the DNA fragment of the bacteriophage genome was inserted in DH10B', a kind of *E. coli*, via transfection. The transformant harboring the plasmid was cultured, from which the plasmid containing the gene fragment was extracted by using plasmid purification kit (iNtRON). The size of the DNA fragment included in the plasmid was confirmed by electrophoresis and the final effective clones were selected. The plasmid of the selected clone was recovered, followed by gene sequencing. Contig map was made using the obtained gene sequences by the conventional method. The total gene sequence in 157,662 bp was analyzed by using primer walking. The confirmed genomic sequence of the bacteriophage STP-1 was presented by SEQ. ID. NO: 1.

Based on the genomic sequence of the bacteriophage STP-1, similarity to those sequences of the reported bacteriophages was investigated by using BLAST. As a result, the genomic sequence of the bacteriophage STP-1 demonstrated the highest homology (93%) with the sequence of *E. coli* bacteriophage vB_EcoM_CBA120 (*Escherichia phage* vB_EcoM_CBA120) (GenBank Accession No. JN593240.1). The total genomic sequence of the *E. coli* bacteriophage vB_EcoM_CBA120 was 157,340 bp, which was similar to the size of the bacteriophage STP-1. Open reading frame (ORF) of the total gene sequence of the bacteriophage STP-1 was analyzed by using ORF finder. As a result, the bacteriophage STP-1 had total 207 ORFs, which was different from the *E. coli* bacteriophage vB_EcoM_CBA120 (203 ORFs). Among ORFs of the bacteriophage STP-1, multiple numbers of them were confirmed not to exist in the sequence of the *E. coli* bacteriophage vB-EcoM_CBA120.

Therefore, it can be concluded that the bacteriophage STP-1 is a novel bacteriophage which is completely different from any of the reported bacteriophages.

Example 3

Killing Activity of Bacteriophage STP-1 to *Salmonella Typhimurium*

Figure 2:
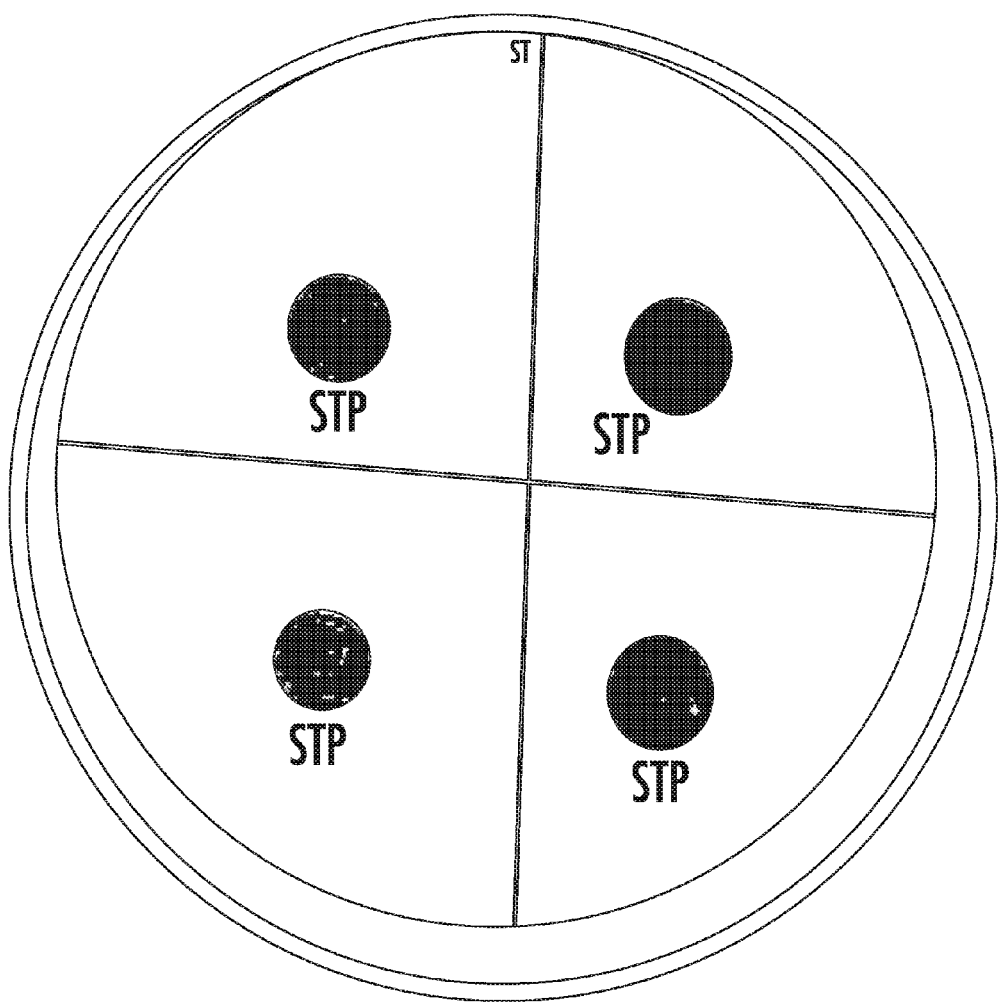
FIG. 2 is a diagram illustrating the killing activity of the bacteriophage STP-1 against *Salmonella Typhimurium*.

Killing activity of the isolated bacteriophage STP-1 to *Salmonella Typhimurium* was investigated. For the investigation, clear zone formation was first observed by spot overlay assay according to the same manner as described in Example 1. 50 strains of *Salmonella Typhimurium* were used in this investigation. They were isolated and identified by the present inventors as *Salmonella Typhimurium* earlier. The bacteriophage STP-1 was confirmed to have the ability to kill all the *Salmonella Typhimurium* used in this experiment. The result of this investigation is presented in FIG. 2. In addition, killing activity of the bacteriophage STP-1 to *Actinobacillus pleuropneumoniae, Bordetella bronchiseptica, Enterococcus faecalis, Enterococcus faecium, Streptococcus agalactiae, Streptococcus mitis, Streptococcus uberis, Escherichia coli,* and *Pseudomonas aeruginosa* was further investigated. As a result, it was confirmed that the bacteriophage STP-1 did not have killing activity against those bacteria.

From the above results, it was confirmed that the bacteriophage STP-1 can be used as an active ingredient of the composition formulated for the purpose of prevention and treatment of *Salmonella Typhimurium* infection.

Example 4

Application Example of Bacteriophage STP-1 for Preventing *Salmonella Typhimurium* Infection 100 µl of the bacteriophage STP-1 solution ($1 \times 10^8$ pfu/ml) was loaded to a tube containing 9 ml of TSB medium. Another tube containing 9 ml of TSB medium alone was also prepared. The *Salmonella Typhimurium* culture solution was added to each tube ($OD_{600}$: 0.5). After *Salmonella Typhimurium* bacteria were added to those tubes, they were all transferred to 37° C. incubator, followed by shaking culture, during which the growth of *Salmonella Typhimurium* was observed. As shown in Table 1, the growth of *Salmonella Typhimurium* was suppressed in the tube treated with the bacteriophage STP-1 solution. In the meantime, the growth of *Salmonella Typhimurium* was not inhibited in the bacteriophage free tube.

TABLE 1

Suppression of *Salmonella Typhimurium* growth

| | $OD_{600}$ | | |
|---|---|---|---|
| | Culture 0 min. | Culture 15 min. | Culture 60 min. |
| Without bacteriophage solution | 0.5 | 0.7 | 1.5 |
| With bacteriophage solution | 0.5 | 0.1 | 0.05 |

The above results indicate that the bacteriophage STP-1 of the present invention not only suppresses the growth of *Salmonella Typhimurium* bacteria but also even destroys them, so that it can be used as an active ingredient for the composition formulated for the purpose of prevention of *Salmonella Typhimurium* infection.

Example 5

Treatment Example of *Salmonella Typhimurium* Infectious Disease Using Bacteriophage STP-1

Treating effect of the bacteriophage STP-1 was investigated in pigs infected with *Salmonella Typhimurium*. Particularly, two pig groups were arranged and each group had 5 weaning pigs at 25 days of age. The test animals were raised separately in laboratory animal facilities (1.1 m×1.0 m), during which experiment was performed for 14 days. Environment was controlled in the thermal insulation facility. Temperature and humidity were regularly controlled and the floor of the pig room was cleaned every day. On the $7^{th}$ day from the experiment started, all the pigs were orally administered with *Salmonella Typhimurium* solution. The *Salmonella Typhimurium* solution for oral administration was prepared as follows: *Salmonella Typhimurium* was cultured in TSB medium at 37° C. for 18 hours; The cells were recovered; and the recovered cells were suspended in saline (pH 7.2) at the concentration of $10^{11}$ CFU/ml. A day after the administration of *Salmonella Typhimurium*, the pigs were orally administration with the bacteriophage STP-1 ($10^9$ PFU) (bacteriophage solution treated group), twice a day, by the same method as used for the oral administration of *Salmonella Typhimurium* solution. The control group pigs were not treated with the bacteriophage STP-1 (bacteriophage-non-treated group). Feeds and drinking water were equally given to both the control and the experimental groups. All the test animals had been observed every day since they were administered with *Salmonella Typhimurium* to see if they had diarrhea or not. The condition of diarrhea was examined by using diarrhea index. Diarrhea index was made by Fecal Consistency (FC) score (normal: 0, loose feces: 1, moderate diarrhea: 2, and explosive diarrhea: 3). Diarrhea index was continuously increased in the control group pigs for 4 days from the administration of *Salmonella Typhimurium*, but the index was slowly decreased afterward. In the meantime, diarrhea index was constantly reduced in the experimental group pigs from the next day after the administration of *Salmonella Typhimurium* (Table 2).

TABLE 2

Diarrhea index

| | Days after *Salmonella Typhimurium* administration | | | | | | |
|---|---|---|---|---|---|---|---|
| | 0 | 1 | 2 | 3 | 4 | 5 | 6 |
| Control group (bacteriophage non-treated) | 0.4 | 0.8 | 1 | 0.6 | 0.6 | 0.4 | 0.3 |
| Experimental group (bacteriophage treated) | 0.4 | 0.3 | 0.3 | 0.2 | 0.2 | 0 | 0 |

The above results indicate that the bacteriophage STP-1 of the present invention is very effective in the treatment of infectious disease caused by *Salmonella Typhimurium*.

Example 7

Preparation of Feed Additive and Feed

Feed additive containing bacteriophage STP-1 at the concentration of $1\times10^9$ pfu/g was prepared with bacteriophage STP-1 solution. The preparation method was as follows. Bacteriophage STP-1 solution was evenly sprayed on maltodextran at the proper weight ratio, which was then vacuum-dried at room temperature, followed by pulverization into fine powders. Silica was added thereto at the weight ratio of 5% and the mixture was well mixed. For the drying process, either reduced pressure drying, drying at elevated temperature, or freeze drying could be used. For the control, bacteriophage free feed additive was also prepared by spraying buffer (10 mM Tris-HCl, 10 mM $MgSO_4$, 0.1% Gelatin, pH 8.0) alone which was the same buffer that was used for the preparation of bacteriophage solution, instead of bacteriophage solution.

The above two feed additives were mixed with feed for hog respectively at the weight ratio of 1:1,000.

Example 8

Preparation of Water Additive and Disinfectant

A water additive and a disinfectant were prepared by the same method because both were formulated in the same form and have only difference in their use. The water additive (or disinfectant) containing bacteriophage STP-1 at the concentration of $1\times10^9$ pfu/ml was prepared. The method of preparation of water additive (or disinfectant) was as follows. Bacteriophage STP-1 was added to the buffer which was generally used for the preparation of bacteriophage solution at the concentration of $1\times10^9$ pfu/ml and then well mixed. For the control, the buffer itself was used as the bacteriophage free water additive (or disinfectant).

The prepared two different water additives (or disinfectants) were diluted with water at the ratio of 1:1,000, resulting in the final water additive or disinfectant.

Example 9

Investigation of Feeding Efficacy in Pig Farming

Improvement of feeding efficacy in pig farming was investigated by using the feeds, water, and disinfectants prepared in Examples 7 & 8. In particular, this investigation was performed by observing death rate. 30 piglets were divided into three groups (10 piglets/group) (group A: supplied with the bacteriophage containing or free feeds: group B: supplied with the bacteriophage containing or free water; group C: treated with the bacteriophage containing or free disinfectants). The investigation was performed for 4 weeks. Each group was divided into two subgroups of 5 piglets. Those subgroups were either treated with bacteriophage STP-1 (subgroup ①) or not treated with bacteriophage STP-1 (subgroup ②). The test piglets were 20 days old. Each group piglets were raised in an isolated cage separated from each other at regular intervals. Each subgroup was sorted and marked as shown in Table 3.

TABLE 3

Subgroup sorting and marking in feeding efficacy test on pig farming

| | Subgroup sorting and marking | |
|---|---|---|
| | Bacteriophage STP-1+ | Bacteriophage STP-1− |
| Feed | A-① | A-② |
| Water | B-① | B-② |
| Disinfectant | C-① | C-② |

The piglets were supplied with the feeds prepared in Example 7 and the water prepared in Example 8 according to the conventional method as shown in Table 3. Disinfection was performed with the conventional disinfectant and the disinfectant of the present invention by taking turns, three times a week. The day when the disinfectant of the present invention was sprayed on, the conventional disinfectant was not used. The results are shown in Table 4.

TABLE 4

| Group | Death rate (%) |
|---|---|
| A-① | 0 |
| A-② | 20 |
| B-① | 0 |
| B-② | 40 |
| C-① | 0 |
| C-② | 40 |

From the above results, it was confirmed that the feeds, water and disinfectants prepared according to the present invention could help to reduce death rate in pig farming. Therefore, it was concluded that the composition of the present invention was effective in the improvement of feeding efficacy in pig farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating *Salmonella Typhimurium* infection in a subject animal in need thereof, which comprises the step of administering a composition comprising an isolated bacteriophage STP-1 having a genome comprising SEQ. ID. NO: 1 and deposited under Accession No: KCTC 12012BP as an active ingredient to a subject animal.

2. The method for treating *Salmonella Typhimurium* infection according to claim 1, wherein the composition is administered to a subject animal in the form of a feed additive, a water additive, or a disinfectant.

* * * * *

SEQUENCE LISTING

<160> NUMBER OF SEQ ID NOS: 1

<210> SEQ ID NO 1
<211> LENGTH: 157662
<212> TYPE: DNA
<213> ORGANISM: Bacteriophage STP-1

<400> SEQUENCE: 1

| | | | | | | |
|---|---|---|---|---|---|---|
| atgaaaatgc | gcaagtccga | gcatttcgtg | cgctcttctt | ctaccatcgt | cggacagaca | 60 |
| ttcaatgtca | agatgacgga | taaattattt | gaaacattat | tttcaagtct | ctacaaatat | 120 |
| aaagaggcgg | cgtctttgcg | tgagacgttg | tgtaatggta | tagactcaca | taatatgcgt | 180 |
| gatcgccaac | aacgctggat | gccatcgcat | tatgctcctc | tcactcctat | gcctcaacga | 240 |
| tacagcaaac | atcttgcccc | caagggaact | cctgttgttg | tacatttacc | ggatgttatg | 300 |
| gaaccctggc | tggaaattaa | agattatggg | gttggtcttc | cattagaaat | gatcatcggc | 360 |
| gagcctatta | cagcgcgtga | agatgaagtg | ctggttgaag | gtaatatcgt | cgtgaaggaa | 420 |
| gacgaaatcc | ctgatagcac | tgctgttatt | ggtacacctg | gttattataa | tggggtactg | 480 |
| gtattccgcg | ctgaggatgg | cgagatcatt | cgtggtcctg | gtttgtatac | aacactcttc | 540 |
| catagtacaa | agaggacga | cgacgggcaa | ataggggcgt | ttgggctagg | ttctaaatcc | 600 |
| ccatttgcgg | tatctgattc | atttacagta | gaaagtcgct | atgaagggaa | actgtatcgc | 660 |
| ttcctgatgt | atctgaatgc | ggacagaatc | ccaactgtgg | atctcattac | caaggattta | 720 |
| gatacccgtg | atcctaaacc | ggaggacact | gatgagttca | acggcctgac | tgttaaagtt | 780 |
| cctgtaaaga | atcagcgttt | taccgccttt | gaacaagagt | tggtccgttt | gggtcgagtg | 840 |
| atgcgaccctt | caatgcgtcc | gaaggttgaa | acgccagtt | atgctttccg | ttggtctgac | 900 |
| atcaacttcg | aaaaccgtgt | aggcaacaca | tatatccaac | cgaagtcaga | ttccgacaac | 960 |
| atccactatg | ctgtcatggg | cggggtttct | tacccgatag | atctcgacca | attggactct | 1020 |
| gaaatatgca | ccgtgctgga | aaaattcccg | agttcctata | ccttcttcga | acttggggaa | 1080 |
| ctgaatgtac | cgccttcacg | cgaagacttg | tcatacgacg | aattcactcg | tgaaagcctg | 1140 |
| aaccgcgtgt | tcaagcatgt | ggccgaaaat | atcatgcaag | cgaagatgta | tgaacttcgc | 1200 |
| caagcggagt | caatgggtcc | tcttatgttg | tatatgaaaa | agactcagct | gactgatatg | 1260 |
| ttcggtagtg | gtttccgtaa | attagtggag | cgagaatttc | ctgcagataa | ccgtttctac | 1320 |
| aaaggcacgt | tccgttatat | cggagcgccg | gacgtcgtgc | gcgattactc | tttggatgca | 1380 |
| cctttccggt | ctattggtag | tccttacgaa | attgaagtac | acgacaacgg | tgtagtacac | 1440 |
| gacagcattt | atgtgaactc | tgtcggaaat | tggttgaaat | ctaaatcaaa | aattgctgtt | 1500 |
| attattgata | actcgaatcg | tgctcgaaac | ctgaagatac | aaacagcacg | caataacttc | 1560 |
| aatgtcgtta | tcgtcgtcaa | accgaatgaa | aattattttca | gtaatcggaa | tcagctggcg | 1620 |
| gcacataaag | aatcatttac | caaccatgag | gaattgaagt | cttattttga | atcatggatc | 1680 |
| ggtgtacaag | aaacaacgcc | ggactacctg | gtctttgccg | ataaactgat | cgaggttttt | 1740 |
| ggcgatttat | tcaatccgga | tgaagtctat | ttcatgcatg | aaatggaata | tgttcgcccg | 1800 |
| accgttgaaa | aagatcctgg | gatgtttagt | ttccattaca | attcatttaa | cttcgacagc | 1860 |
| gtttatgaat | tagatggaaa | aaccgtttca | gatattattg | attcgggcaa | aaagatcgta | 1920 |
| tatatcgaag | tatctggccg | agaaggtatc | cataaaattc | atggtattac | cttacgacaa | 1980 |
| tccgcggctg | gacatttgcg | tgaagcgatg | gaaagaacga | agttcggcga | gaatggaaac | 2040 |
| gaaaacctgt | ttgatttgct | gggagcacat | ccaacaatcg | ttcttgcgcg | tcgtaaatct | 2100 |

```
gttccgatga tgaagaaatt cccagaagta ttcatcccca ttgacgcagt gtttgatatg    2160
ttgcttgagc attataaaga tgaatttcag gcgcttgaat ctaagaaact cctgaaactt    2220
cgcaagggca taaacatcat gtctcatcgc attgattatg gtgccaagct gttgattgat    2280
tcccatggaa aagttacgga tggctatgcc catcatcaac acagggcaaa agcaatcatc    2340
agttatgcga acaacaaat cactgaagaa gaatggaaga ttgttcgtat gctggccaaa    2400
cgaaatccgt ctggatcggg gtacggttat ttccgcaagg ctgttgagga attacattat    2460
catatagaaa tgccttctc aactacgaga ttttccgcg cctgtaacca gttaactcaa    2520
gttgttgatt tattgaatga aaattaact gctgaaggat ttgatgagat aaaggtcact    2580
agcactatat ctcaaaagca aaggccaaa accgatacc gagttgaatg tcatcgtttg    2640
gtgaaattca tgatgtcaac atatcagcct tcggcacaca acgcgattga agatgccact    2700
agatttgtga aggctatttc aaaacgtatt ctcggggcat aatagcccca ttaccccaca    2760
gtgagaacta caagatgaat gctatagaaa acgtattct caagctgttg aatgagaaca    2820
gaagtcaaag ttcaatagcc agtgaattgg gcgtaccgcg ctcaatgata caacgcgtgt    2880
cggataaaga actgggagtg gatccagctt cgattaagtc tctgaccact gaacagattc    2940
aagaaataca aaccaagagc agcaaaggtg aaagcaattc ttctctggca tcagtttatg    3000
gcgtcagtgc caaacaatt gcccgcgccc tgatggttcg tatcatcaaa gaatctaata    3060
acgtggtcgt gatttcgcca attaaagaat tgactgaaga agggaaaatc cccgacacct    3120
atgaagttct ggaaggttcg gtgtctgtcg attctgaagg cgaagaatgg tatgttggcc    3180
gtttcctgga aaaccaaaca gtgtttatct gtatgcgtta cgatagctct gctgctattc    3240
aggccaaact tttcagaagc gaagaactga accgttaga aactcggtca agccgcttca    3300
atgaagaaaa tatttcgccg ttggccgaat tggcgacagc actggttgat ggcgttacca    3360
aagtcaatga tggcgtggta atcagtgtac aacatgacgg cgaaacatac ccgatgcgcg    3420
gttcccttga tgcccgtcgg cgcgtgggtt actttgatgt aatttttaggc cgtacacttc    3480 gtctggcatt gtcatccgta ttattcgtgg tcaagactgt tgcggttgtt ggagaaacag    3540
gcgacaagca aactcagaat tcattaatg aaaaagatct gtctgtgttc ctgaacgaac    3600
accagatcat gattttgccg gaaagtatcg taatcgtggt tgatggtaaa ccggaaacga    3660
tcacaacgag ccaccaggcg tatgaccgta ttgttgaagc gattaaaaat cgtgacgtca    3720
aaacagcgta cactctgatg aaaccgcgtg aagccatcaa acaattcacc acaggcatgg    3780
ttgacctttc agacaatcgt gttcgctggg gtggctatga tatcaccgga acttccgttg    3840
ccaaacgcat tttggctttg gcattaaaag gcgattatcc gaacttggaa cgcttgggtc    3900
gtttcctgga caaaatgttc caaaacccga gcgccgcgct ggttcagtcc ggtcgaatct    3960
atgaattcat ggcatattcg gatatcgaaa ttcatgaaga cggtgatatc atcctgtata    4020
aatccgttcg cggtaactac atggacaagc gcacaggaaa agttagtaat gctcctggca    4080
ccattgttcg gatggctcgc tcattcgtga acgataacaa caaagatctg tgctcttacg    4140
gtcttcacgt ttgttctctg gcttatctga acaatgtttt tggtagcctg gacaacgcg    4200 ttgtccgttg caaactgaac ccgaaagata tcgtgtctat cactgatgat tatggctcca    4260
gtaaaatccg ctgctgtgaa tatctcgtgt tggatgacta taccacggaa tacaaccgcc    4320
aacataaatc cattgatgtt gaaggtctat acaagtaacc gcgaactgac ataaaagagg    4380
gggcttcggc ctccttttct ttgaggtcga tatggaaacc agagatgttt acttcgtgta    4440
```

```
tgagcaacag gcatttggat cactgcgccg aaaaacaaag ttccttgttg attcattcca    4500
atttgatgga gaactcaagg aatactcgtt caggaatttt cctccgagag aagtcatagg    4560
cgaccagttc gtgaaattat tttgtcgttg tggcggctgt gactttaacg acgacggata    4620
ttccatgcat gtttattgct gcaattgttg tggtaaatat attacagtct ataggagaac    4680
tgatcatggc gaagacacaa agaaaattg aaaacaccca aaccattcaa gaaatcactg     4740
cacaggaaga aaataaactt cccagttatc tgcaacgcgt ggtggataac gtgcctcagg    4800
gcggcgacgg cggtattgtc tacgctggtg actacggttg ggtgtgtgaa tataaagacg    4860
gctctaagga gcttctagag gaactcaccg gacttgccgg aactttgcgc cgttatgggt    4920
tagataaatt cggtaagccg atgaaaccag gtactgtggt atcaaccgat attacagttg    4980
aagttcttct tttgctcgat atcaatgatc ttaaaacact tgcggaaccc ctgggtatcg    5040
acgcgactga ccgtaatgaa ataatctcgc aattggctga aaaactgcag attaaataat    5100
cccagtgtat aactgctgat tataattcaa tatggctatc gttgacgaaa gcaatttgat    5160
ggagtacgct ctaagacatt atatcacccc tggtgtctca agagatgatt tgatggtaga    5220
cattcagcga atttcgctaa ttaatcaatc attgaaaaga tttgtgccag ggaaaagtcc    5280
tcgagtactt atcaatcaat tgattattct tttcaatacc tttgaaaccg aagccgtgtg    5340
tcgaatgttg gtgttgaaaa cggataagaa ccaacatcct cgtcttaaag cagcactgtt    5400
gacgttaggt gtttggcgag atgatttatg ttccggttca tacgaaccag ataacgagct    5460
gatgatggct ctgaacaacg atttggatga gtggaggaaa ccatgccaac aatcacagta    5520
ttagtcgcac cggaagttgt ccgcaacaaa cccgaaaccg aacgcaatca tgtcgtgacg    5580
ggtgttgcaa agggttggca aaagaccagc ctcaaccaag atcctgatga gatcctgacc    5640
gaatgtaaag gtcttgacgc tctgctcacc aagagcaatt tacaagcgga cggtgtcacc    5700
aaagtggatc ccaccaagcc tatcggcttt caagtatctt atgaaatcca cgatccgaat    5760
gccattttaa ccaccggact tgtgattact ccagctacag ccagcgggga gatcggacaa    5820
tttgttgaat tgctagcgac ggtatcccct gccaatgcca catatcaagg cgttaattgg    5880
tattctggtg atattacgaa agctgtacat gtcggtggtg gtaaattcaa attgctggct    5940
tcaggaactg taacggttta tggtgtcacg gttgaaggga atcacacaga ttctacggtt    6000
attacagttg caggcgctct gtctttgtct actgatttac ctgccaccaa agacgtaact    6060
tccggacaag acggaacctt tagtgttgtt gctgcgggtg gtacaactcc atacacttat    6120
gtgtggcatt tctctgatac tcctgggggt gcggggtcag ttatcgatgc tggcactaat    6180
gccaccgccg ccactgctaa cctggttatc acagcagttg aagccgcaaa tgaaggcgaa    6240
tattggtgtg ttgttctga tgcagatggc cattctgtca cgtctactcg ttgtgaaatg      6300
gctgtggtgt aatttatgaa gagcttccag gatttccttg aagactcttc tgctccggca    6360
accacgaccg ccgatgtggg gaaacccgaa ggcggtatgg tcaaggagcc tgtcaaaaaa    6420
ccaaaagatc ttgaagaaga gtctgatttt aaaaagatct ttggcaacat tttcaaagat    6480
ttggatttat ccaaggcacg aaaatggaat tcaggacag gccaatacga cgattaaaga    6540
ggcttcggcc tcttttcat ttccagcatt gggtgtataa tggacccgtt ccccatgagc     6600
ggaacctaac tgaggatata ccaaatgcaa tctatgatca aacgtaaaat agaaatctcc    6660
atgaatgccc atgtcgatat gatccagcag cttgtggcag atgcgtatga gatacaaaag    6720
gaacgtcaga ttaggggagt gatagaccct atttgctccg gcaacatgct ctactacaga    6780
atgctccgcc agaccggaca tacagccgct ctgaagaaac tactttctaa aaagtttcag    6840
```

```
gtcgaaaacg acgcatatgt gtttggcatc ttccatactt ctcgtgaacg tgatgcattc    6900
ttctatcctt cccgcaaccc tcagacgggc gaagaattac ttatccctga tgtcgacaag    6960
aaagagagca cgacgacaat cacccatttc atggggacca ggatcgataa ggctaacata    7020
atcgtgttct ctgacactct acatgatgta aacgtttag ccgctgcccg tgaaatgttg    7080
caggatgctc ggaccagtct cacaaatttg actttagtag tgtttctggg ctagatatct    7140
gtgtggggag agaactcccc attttgaatc ggaggtgatt tatgttacgt tgcaagagag    7200
gttccaactc ctttaagttg ggtatgctga ctggagtaac gttcatgatt gctttagaca    7260
gccttgtggg actgctttcc cttcctgatt tcaggatgga acgattcata ttgttagttc    7320
tatttggcgg tgtctcggtt attagtgctt tgaaagcgta caaaaagatc tgatttaact    7380
cacacacaca gcaattttga tttgagaccc tatatcatgc tcccattact caatgttcca    7440
aaagaacgta tgacgccgga tagtgaaggc aagacccatt acaacatata cagtcgaagc    7500
cgcacagaac taggcagatt cctttcccat tttgcatacc atcccatgga tactgttgat    7560
ggtaatttca attcgttaga aggctactgg tattggctaa aatatcgcca cgacgacttg    7620
cgtagtcttt acgggaacga cgccaagcaa tttggacaaa ccctggccaa gtcacgcatc    7680
gttgtattgt cccctgatga tcccaaattt aaacgagaca ttatcgcagc gacgagtcaa    7740
aaattgctga caatgccatc caagttgaga ttccaattgg cccacagccg tcttccctg    7800 attcacgctt atgaacatca ggggaaatac agttttcaaa actctatgga ttttatcata    7860
cagcatatta accgcttccg tctagaagga tatttgaaat gaattttcta aaaactatct    7920
tcaatacatc atatgaactc agccagcgcg atcctaatcg ttctcctgtg tttgtatatt    7980
gcaaactcgt ggaagagtct tgtgaactat cagatgtgct ttatggaatc gctgcatccg    8040 aaccctgaa cggtgaagtg gcggacgtta tcatctcggc tctggatcta ttatatgttg    8100
tggattatca acaagttcaa caacatgggt ctatgaccaa agaagaaatc tttgactcca    8160
tggtgtttgc tttggctacg gccaatcaca caactgatct cagccaacat acgttggaag    8220
attattggtt ctgtagtggt gttgaaacta tagacaaata tcttgcgatg gttaatcatt    8280
acaaaggccg catcactcgt ttactgaacc aacctcaacg ttcagaagat aatatggtgg    8340
acctggtttc aaatctgata cgcaatactg ccaaattggc gtgtgggtat aatcaaaacc    8400
atatcaacac gatcgttaaa gtagaacatg ccatagaaca caaagttgaa aagtggcgtg    8460
gtaaatttgg tctataagcc aaccccatac ataatcttgt gtgtttacca ttgacgggat    8520
aggccgatgt ccaacaaaat tgatattgaa cgcaaataca aaaagctcac tcacatagag    8580
catatcctac ttcgcccaga gcgtcatctg ggcagtatcc gttcgtctgt ggggacggtg    8640
tgggtgtatg acccaaccaa agacaaagtc atcttccgtg acaactttga gtactcccct    8700
gcgctgatca aacagtttga tgaaatcatc accaactgtg ttgaccacag caagaccct    8760 gagggtaaag gcttgacgga aatcaccgtc acggtctccc ctatgaacgg tcaaatcatc    8820
gtttccgaca acgggggtat ccctgtggtc aagcatggcg tcaccaatga gtggctccct    8880
gagatgttgt ttggctcgct ctatgcgggc agcaacttca acgatgagga cgaggagtac    8940
aacaaccaga agtccggcgg ccagaacggt gaagggcttc gctcgtcaa cgtgttctca    9000 aagtggttcc gcgttgctac cagtgacggc aagaagtctt atactcagct gtttgaagac    9060
aacatgagca gaagtccaa tccggtcatc ggcaatacac cgaaagagtt cggcaccact    9120
attgcctgga tccctgatta tgcgcgcctg ggtgttaagg ggcttgacca gaacaacctg    9180
```

```
ctcatgattt accgtcgtgc attcgaagtg gcggcatgca acccgcgcct gaaggttgtt    9240
ctcaacggca agcaaatccg cattgatcga tttggtcatt tcgttgatta cttctacgct    9300
ggctcggctg ttgatgaaac ggatgattgg tctgttgcta tcactccctc atctggtgtg    9360
ttcatgcatg cgtcatacgt gaactcaatc gccacgcaca tcggtggacc tcacgttgat    9420
tatgttgccg accagattgt ggcggcgata cgccctcagc tggttaagaa gttcaagacc    9480
gaactgaagc cagcgatgat caagaaccac atgtcattgt tcatcgccgc cgacatcaac    9540
aaccctcgct ttgacagcca gaccaaggag cgcatgacga ctcctgtgag ccagtttggt    9600
acgtcctaca agcccagcga taaactgatt cgcaaggcgc ttgagttcgt gacagcaggg    9660
ctgagtaaag aactggcttc attacgcaat gaacaagaag atgccgaatt tgaaaaggcg    9720
aagaaggata tcagcaaacg ggattatcgt gagattgaga agtattatcc ggcgaccgcc    9780
agaggcgacc gcagtgggtg ttctctgcta ctgacagaag gtgatagcgc atccaaccct    9840
atcctgaacg ctcgtgatac caagaaaatt ggtttgttcc cgcttcgtgg taagttcatc    9900
aactgcctga acgcccgcg ctcaaaggtg atggcgaaca agaattcaa gaatttatgc    9960
accattcacg gcggtgctgt gccaggccag ccgcttgata tcagtcgcta tccacagacc    10020
gtcgtggcaa cagacgcgga tgacgacggc attcacatcc gtgggttgtt aataactctg    10080
tattgtacgt tctggcctga atacgttcgt cagggtaggc tgaagctcct tcgtactcca    10140
tacatgcgcg tgtggtgtgg taatataatg catgaattca tgaacaatgc cgaatatgag    10200
gagttcctga agacaccgga cgccaagaag atcacgaaga agaaatatct gaaaggtctt    10260
ggcggtaaca gcactgaaga cttcaagcgt attctaaaca acctggatgc gtatactacg    10320
acggtcacgc tggacgatgg atacaagcag tcactgaaga atggcttcgg tgatgaggcc    10380
gccgattacc gcaaaacctg gtttagcgat gtttgcctat ttgaaaccga ggatgaataa    10440
gatggttgcc aagagcatta ctgtaacgga ctttgtcaac accgaccaca aggagttttc    10500
cgtggtcaac agcatccgtc aaatccctca gctgattgac agcctgaagc caagccagcg    10560
caagatcctc ttcgctgctc ttgaatacaa caaggaggag attgttgacc gccttggcat    10620
gttcgccgcc gctcgcacga attacaaatc tggtggtgag aacatgagcg gtacgatcgt    10680
gaacatggct cagggggttcc caggtacgaa caacatccca tactttgacc gcgatggcca    10740
gtttggttca atcatggggc gcgaagcgtc ttccgctcgt tatatttcag tggcagtgtc    10800
tgaagttatc cgtaagatct tccgaaagga ggacgatggg atattggaat acaattatct    10860
tggggaagag aaactggagc cgaaattctt tttacccatc ctgcccatgt ttctcgtgaa    10920
tggtatcaat ggtatcggct cgggttatgc caccgacacc ccatgccact gcgttaagtc    10980
cgtgctcagt gccctgagag cacttctccg tggcgaagac ccgaaggact aaaaccgta    11040
ctggaatggt ttcaaaggag agacaggcta tactgaggaa ggaagagcat acagtcgtgg    11100
attgttcacc cgcgttaatg caaccacttt gaacatcacc gaggttccta ttggttggtt    11160
ctctaaaacc tatgagacca aagtgctgtt gcctctgtac aaggcgggtg tcctcactga    11220
gtacgccaac gatacgaccg aagatggttg ggatatcact gttgtattca agcggggtga    11280
attgtcaag ttgaatgacg aacaggttga acagatgttc cgtctctact cagctaataa    11340
gcccgtgtgg acagcttggg atgaagatgg tgttattcac cgttacgatg gttggaaaga    11400
tatgttgctt ccatttttca attatcgcct gagtcgctat gaagatagac gtcagtatct    11460
tatcaaggaa ttgaccgcaca aaatacaccg tttgaacaat cgtgccatat tcattgggtg    11520
ggctgtcgtt acagatatgc gccggagcct cacggaactg aaagcgttat tccagacaga    11580
```

```
ctatcctgat tttgatggcg atctcgatga tttattcaag atgtctttat catcaattac   11640
actagatgcc cgtgaacgtt tgttgaacca gataaagaat ttagaagttc aacgagaaga   11700
attaaataat aagcaagaca tcgatcttta tactgaagat ttagatgatc ttgaaaaggc   11760
attgggccta taaatccgga gggtgaattc cctccaaaca agcaaggggt tcaccatgtt   11820
tgtatatttc cgcagtctct cattgctgac tttcttctat tggttgttcg atatcttatg   11880
ccctcgtttt attaaagagg aagttgcttt tgtcaatcat gaaggccaac aagatttatg   11940
gatacctctt tgcgctcttt ctgatgtaac cgaatcggat gaagtgggta tggttggcac   12000
catgcgttca tttaatttat ttggattcgc attattccct aagttaattg agaattaca   12060
cccatacaat cctgatgaag aagtggaggc gtgatatgtc aaaattattg actccaaaat   12120
tattatcaat gggtggttcc atatattttc attgtcctgg atgtaatatg cttcatcctt   12180
atcgcatttc agggcaaatg cctggcccaa tatggcaatg aatcacgat ctcgaatcac    12240
cgactttcac tcctagtctg ttggtgaatc attctgatcc aaatagccgt tgccatttat   12300
ttttgacaga tggcaaatta caattccttg agattgttt ccacgaatta aagaatcaaa    12360
ccgtggagat ggtcgatatt cctgaacctg aaatatggat agattagatt atgaaattac   12420
ttggatattt tcgttctttg cctactggat ctcctaatgg gtgtcaatta tactctgaag   12480
tgaaagggga cgtgaacgac actcacatcg ccttgtatgc tcgtgatata cctgacccaa   12540
ccaagtttga tcggcgtgtt gtggctgctg ccaacaaata tggtgatgtg atcgttgtaa   12600
gcgcccgaca tcacgacaaa ttgatgaaca cgcaactcaa acgattgaag gaagcaggta   12660
ttatcgaaac cacccacact cgtgaacaag ggtttattga taactatggg caatggatgt   12720
cccgtgaaga ggctgctgtg gtcgctcgtg aagccggaca aactaatcag gtccgtttga   12780
agaacactcc tttcaaagaa ctcttttccg aagacctcta ttgaataaat tggcggtata   12840
attgccgcct aaccccataa tgagacaaat aacatggcaa atgaaattgg tgatattgcc   12900
cagttccgtg ctatttcacg ccgcctgaaa tcgtatggac tcgtcatcga agaaatagat   12960
gaagatgttc agggtgtatt ggaagggatg tttgggagta ccgttggaac ggaattattt   13020
gaacttttaa agatggcagc tgataaccaa ttcgttgaat atatttctga acacgctatt   13080
gatggtctga ataaatgaac gagttatatg aatttgaacg cgtgtatgag tccgcttcag   13140
tttcaggata catgaaacga ttatatcaag aaatctgtgt tcgtttgata atgcgaggaa   13200
tatctgtcaa ttgcgttatg gcacagacag acagttttat tatgacactc actgaccatc   13260
gccagaatat gtgtatcatc caggttagct gtgtcaacaa cgaaattata caatggagac   13320
gttacgcatg accacatatg ttatcacaaa cggcgattta ctgaaagccg ctacgagttt   13380
taatctcatc aatgctttcg ctcatggcgc aaattgttgg tctgtgatgg gcgcaggtat   13440
cgccaaccat gttcgattag atttcccaga aatttaccga gccgaccaat tagatgaacg   13500
tggtccggaa caacgtttgg ggaacatgtc ctatgcgttt gatcatgaca ctggtgtctg   13560
gggattcaat ttgtacactc agttctaccc tggtcctaac gcacgcatgc cttccattat   13620
cagttcagtt cagattatgt ttgaacaagt tcacgatatc attgaggcaa aaactgacga   13680
aacagtctat gttggtttac ccgccatcgg ctgtggcatc ggtggattga aactgtttca   13740
tgtggtgagc cagattaata aaatcgcgga tactatcttc gaagatacca ggcgtcgtgt   13800
cgtacccgtc ttttatatcc gacagggtga cgggttgaa caagatttac aagaactttc    13860
ccagatggta gactacggaa tctctgtcgt cgctagtgaa gaagatatca tcgaagagga   13920
```

```
aggtattgga tgaagcgtga ataacagaa gagatgctcg ccaaagccgt tcttcatccc    13980
aaggtgcgtt ttgcatttat ccctacacgt ttacacgatg gaaattgggt atggctggag    14040
cattatgttc gcgctcctat cggcctatat gcccaactcc gttatggcgg cgaagtcgag    14100
ttaaaacaat atcgcgtcgg cggggggatta ggcgggttgg atgacgggga atatttccca    14160
catcgaaatt tcgccatgaa cgataattca tatttcaaag tcgagtatgc caccgcttgt    14220
gggacatatc ctttgaaact tcttttagag aaagcagggg aaactgatgt ataaatctaa    14280
tttcttggcc gtcgctgata gcgaaactct cggtcgttgg gatgatgctg tcatgttgtc    14340
ttgggcacag actatcgccg acctgaccaa gcgttatact cttcagcagc ttgttgtaga    14400
gcgcacgaca tttatcaaac tgaatgtcaa agaacagatt gaacttggcc gtgtgaaaga    14460
ccagggcact gtggaatggt ggctgggtac aggtaaacgc aacccgtgcg acgccgcccg    14520
agctatcagt ctatatccga ccgacaagga tatttctatt ttcaaattgg ccgatgaaat    14580
tcgcagggga tgccatcgcc ttgggatcga cccgcgatcg gttgactggt gtgataggaa    14640
tctgtttgac ctacgcaagg ctcagcacat cattgaggtg acgtgtaagc aagattccaa    14700
cgaaccttgg gactatcacc acacatttga catcgtaagc tggctgaagg gtgttgggca    14760
gcaggatcga tatgctggta tcaaggcgtg ggaactggaa ggcatggtct atcatgatcc    14820
tcgttatgat gcggcgcttg actggctacg cattcagaaa accatggaag acctgatggg    14880
gctgaaggta gaaggatgat tctttccttg ttttcatggt tgtttacaat catagttttc    14940
ttcatagtct gtgttcaata ttttggaggt tcttaaatgt tctttcaaat tgtcggggtg    15000
atcacgacca ttgttttttgt tgccataacg ctttggatat tgtattcttc atttatccat    15060
ccgattttc aggctctcag tattacgcgt tggctcacag cgtgttcttt gaaatccgga    15120
agcgaatgcc cttctttatc gtccaaatgg aaattcttca aatgggcgta tgaagtcgga    15180
ggagtccgaa caaccagata ttcaaataat gtgggggaat ggtttagcat cggcaattgg    15240
cgtttgtacg aatctgaaga caaataagcc ccgaaagggg cttttctatt tgtataatgt    15300
attatcattg taccatcata tctttatggc gcacaacaaa tgaaagagca agaaattatc    15360
cagcattgta ttcgcttagg aacattaaaa cctctctatc aggctttgcg tttcaatgcc    15420
attaaattca aaccttttatc aagaactatc gcaacgttct ttgccatgcg ttctgttgga    15480
aaaacgattt tctttgagca tgacatttat tttttatacaa agattaatgg cgaagattta    15540
gataaaatga ttttcgtgaa cgacgataaa aatatgaaga taaaagtgga aaacgaattg    15600
cgcaggataa atgattcttt aagaggaata ttttaatgga aattgttgtc tcaatatctg    15660
attgtgattt tgtataccgt gttcttcaag gggatgctcc attaccggag aataatcaag    15720
aagtgacgtt gttctggtct ggtggggtgg atagcacata catgttgatt tggttgttat    15780
cgaaaggata ttcagttcat actgtgtatt gccacctcga aaataataaa tttaaatcta    15840
agcgcgaaaa ttgggcgagg aataaaaatac acaactggat taataaaaat gccccacttc    15900
tcatgtatcg ttggacacat catcaagaac ctatcagtag catcaacgtc ccgaacggtg    15960
gttttcgctc ttgtttagca caagccccga tatggttatt aaacacgcaa tttaaaggca    16020
ggagcttgcc ttccacgtat atattggcat atgttaacgg cgatgacgca atacactgga    16080
tacccgcctt taataaagtc attgaagggt acaacatgat gaccagagac ggggaaagac    16140
ctattgaaat tttatatcca ttgattagtc tcaagaaatc ttggttctat catcacatgt    16200
ccccaataca tgacttaatg acatggtgtg aattgccaat tttgaaaaag aattgtgatt    16260
gccctgcgtg tgttcgacat cgccatgagt tatcatagag atgaaacgtt cagttgttgt    16320
```

```
aaatgacatc acgagattga taaatcttat caaagacgtc ttcccacaac aggtggatgt    16380
tgagtatgtt gggaagaacg gaaagtgcta tcaggttgct ctggttctga agcatgtgta    16440
tcctcaagca gagatccatt acagccagat cgaaggtcat gtgtatactc tgattgacgg    16500
acattactac gacatcgaag gcatccactt cagtgtccca ccagacacgt gtttgctcga    16560
acataataga ggtcacaaac cgcatcgttg gcataaaggg tttgtgaacg tgccgatttt    16620
agaatggctg aggaaaccat aatggcggga attgtaaagc accttggtga cactcatctt    16680
gggcataaga aggtctttaa accgcgtgga tttgatacac aggaagccca tgacgctgcg    16740
gtcattgaca gtatctttca ggggttgaag tctcggacg ttcttgaact ggctggtgat     16800
atatgcttca tcgggctga agggttcatt cgcctgatgc gggagggtgc caagcgaaac     16860
attgatgagt ttaagcgacg ccccgttccc gatgactggc gtccgaactt tatcatcaag    16920
gtggcacaag gcaaccatga cagctttaag atgttgttgt ctctgtatct ggacggctgg    16980
attagctcct tcggcgctat gtatgaacgt gacacgcctg ttggccgtgt gttgacaaca    17040
catgttcctt atcaattaga ccgttgggcg tataatatcc atggtcatct tcacgaaaat    17100
attcgcgaag agcgcgaata cctgaactgc agttgggaac aattcaagcg tcctgtaacc    17160
ctggctgagt tattatacac aaatttagga attgtgttat gagaatattc tttcctggtc    17220
agaaagtacc cgaagaaata caaaaggtcg agttatttgg ttataaaagc ggtgatccgt    17280
tcctgcgatt ttcttcacca tgtatcgtga agcgcaatca tgaagggcat tatgtgcgcc    17340
caatcatcct catgggttct gtcatgacgc tgagagccaa aacagactcc gtcgttatta    17400
ccggaagtcc caacataccc aatggaaaga ctacgctaaa ttgcaagccc atcctgtcgt    17460
cttgggtgtt aattggattt ctgtctataa tcttgtttta tcgttacctt actgacttgg    17520
ggatcttatg aaaaagccac gcatcacagg acatcaactc tgcgtccttt taggaatgtt    17580
gaattttgaa aaaggtgaag ctagacgcct ttgtcattgg tatttcaatc ccaaatcttg    17640
gacgaacgat aaagggaaaa cggtttggac ttttcatgcg ccaccgatat ctggcgggtt    17700
tcgttctgta aagggtgatc catgggatac gcgttcaggt caatccttgt tgtctaaagg    17760
tctgatagaa cctgcgttta caatggttca tgacaactct gaagagtata agcattggcc    17820
gaagtctgaa gtaacattct ataggcttac agacctcggt aaagcatgta ctgaataata    17880
ttttaggtta ttgaagaaag gggaaggtat acttcccctt aatttattgg gagagacaaa    17940
catgatttca ttaaaagaaa tgtacgaacg cctcgaagaa ctgaaatcta agaacgtct     18000 gtattcagaa gagaatgcag aaatgtcaga tcttatcgaa aaaattgcgt tgcgtgaaaa    18060
gtatcttcaa cgttatatca atcacccacc tcacattgtt gaacgtgtga acgttgaact    18120
ggaaaaactg tccccaatca cgtatgacaa attgggtatg gataaagtcc acacggctat    18180
ctctggtgtt gtgaactcta tgttggcgtt gggacaagta tttggtcgcc aggaccatga    18240
tgatcttatt ttctacattg agaaaaatgt ggtggtcaaa tgaacgttca tcgcctgaag    18300
tttgagttaa ctcgaaggga agacaacgaa ctcatatatg gggaaatttt catatatgat    18360
ccttatgata cggaatacac tgaatggctg aagataatat tggctggtga agtcgataaa    18420
gtataccgtg ccattgaaaa ggacgccaaa ggagtattaa gttttggtca tcttcgagtc    18480
gcggccatga ttggttcagc tttagaaata gtgtctgaag cgatagccat agatctacca    18540
ggggaacata tcttcatccg tgaatctaaa gttgatatgg caacgaatta tgtgatgaaa    18600
ttgaccttga cagaaaatat ggaaaataac aaaccaagca ttttccgccg tttcatgaac    18660
```

```
aaattaaagg gtgttaaaaa tgattaaacc acgtatgatg ttcgcccata tgcgatcagc    18720
tgcagcatat ggtgtaacca gttatgctcg gcgtctgcaa gtcggttgtg ttatcgtaaa    18780
ccctgaaact gatcagcctg tggctatcgg atggaacgga acgcctcctg gcatgccgaa    18840
tgtttgtgag atgaacaac acgggcaaat tgttacaaac ccgtgtgtca ttcatgcgga     18900
ggaaaatgct ctaatgcgta tccccgaaaa tgcagatgat ttcacagggt tggttatgtt    18960
tgtgacacat agcccatgcc ctgattgcac tcagaagatc atcgacaacg gcaagatcga    19020
taaagtatat tatcaagagc catatcgtat catggatgga atcaaaaaat tgatgaacgc    19080
tggaattgaa gtttatcgga tggtagacga tatggcgatc cttaaacacg ttttcgacga    19140
tcaaggcgaa gtcggatacg aacaaatctt atccaaccca gacaaagtaa ggaattaaaa    19200
tgcgttatgt agaccgcatg ctcggcgaaa atgaacatgt catcgctttc acccgcccga    19260
cttggtggag cggttttttgg atttatgttc tggttatttt aacgattatc ccaacatttg    19320
gattcagctt gttatttctg ataccaacaa ttttaaatgt attgacaact gaattcgcag    19380
tcaccaacaa gcgtgttatt gtcaaacggg gatttattcg tcgtgatgct gatgaacttc    19440
gtcttggtaa agtagaaacc attaaggtgg accagtctat tacaggccgt atcctgaagt    19500
tttcaaccat cagtgttatt ggcacgggcg gtactcgcct gttggctaca ggttgtgcta    19560
aagggaacga attccgtcaa aaaatttatg atcatctggg tgactaaatg attactgcag    19620
gatacaccgt cgatttgtat tgtgagtgtg ttgaatgcaa atcttgtaat tgggcttggg    19680
aagaacatca ccccagatgt gggatgaagt cttatgctgg tgaatcttgg ggagactgtg    19740
ctagacaagc ccgtgctgat gggtggatga tatgcaggga caaacaaact tgctttgccc    19800
ctggacatcc aaggaaatca gggtaataac aaaccatcat cttccgattg cgttggttgt    19860
ttattagcag tttccttctt catttgctct ttcaacgcat taatcctttg agcgcggcgt    19920
cgatcttcca tttcgacttc gcgcttttc ttagaacgaa gagcaaattg ttttttaact    19980
tctgggtctt cacctggcac caaatgttct tctgtccaga taatgaattt ccaacccacc    20040
tttgcacaat gttctttagt tgctgtccac tttgcctgat ttaccaacca agtgcgcatt    20100
gaattattga atgttgattc cttcatcgtt ttagttttgc gaggttcttt aatctggtct    20160
ttgggtttta tttcaataag agtaatttgt aattcatcgg aatcctgccg acgagtccaa    20220
accttcaaat ccatgaaata acgatgggcg cggccatcaa ccggagatat gtaagggatt    20280
acagtttctt ctgaagacca atagacgata gcaggattca tatcacaaaa tttaaaggcg    20340
acaagttcta gcgaagaacg aaatactatt ttgttcacgt cgcctttata tttcttggga    20400
tttacgggaa catacttccc ctgcaaatac atagccatat tctagtccta aatagtgtca    20460
tcactctatt ctaattaaag ggcttcagac catggcgaat ttcaagtcga ccatcgataa    20520
gatcaaagtt ctgaacacaa aaggcttggc caagtctcag aagcaattgg tctatccttt    20580
agacataaca gggggtaaaa ccctcggcca ttatgttcta ttcaacatca accgaatatc    20640
tggttcttca tatggagaca ccacaaccca aaccgtcgaa aatccgatac aaaatccatt    20700
gggtaagact cctgtggttt acggctctaa atcgggttct attagcaaat atgcttgggc    20760
gcgtcatgtc cgctctaacg agtcaattgt gttgtgtatg cccgaatcca ttacaaccaa    20820
ctatggcgtt ggctggaacg gctccgagtt gggattagca ggtatgggtg cccaattctt    20880
atcacgcgcc gcccaagata tgagtcaatt caaacttggg gatgctttga atgttgggaa    20940
agaaatgggg agatttgcgg caacaaaggc cattcaatct gcttcggaag caattccttt    21000
cttgccgaca attaatgctc atgacacatt agaattgttt acaggtacga tgaccaaccc    21060
```

```
gtatgtggaa atgatttcc aaggggtgcg caaccgagaa atcccgttca cattcaaatt    21120
cactccaaga tcgcaaaaag aggcgaaaat ggtgcgggag attatccgtt tattcaagat    21180
gcacatgtat ccagaataca aatacaacaa gaattccagc gcattctatc ttcatccatc    21240
cacgtttgat atcacgttca tggtccaggg agaacgcaac aaatggttgc atcggatatc    21300
gacttgcgtc ctatcaaata tgtttgtcaa cgagacgcct gactcttcat atgctgtaca    21360
caaagatgac agcatcgtgt cgacacaaat cgacatgacg tttatagaac tagaaccgtt    21420
gcacaaaggc cgctttgata ccgaaggcga cagcttctaa ggagaaagat gccatgaaat    21480
attttgagaa atttccactc gtgtggcatc aattaattgg tgtcaaagag gatgaccaag    21540
tcctgttaca gaacttaaca cgacgggtta tggttgttaa gaaaattagg gacatagaag    21600
ggcttctcct gccgtatact gttttcgatg gggaaacccc aaggtctttt gccgaacgcg    21660
tctacggttc cttcgagctg ttttggatcc catgtcttat caatggtatc atggacatcg    21720
cagaggactg gccaaaacca gagcgccgta tcaatgaaga actgacggat cgatacggcc    21780
ttgacggaat gtgggatgtg aaatactacg ttgacgaatt cggtcatgaa acagatccta    21840
gagcaatacg tttagcatat ggccttggtt ctatggatga ttccacgatt atcgccaact    21900
atggtctgac aggtattaca tatcatgatg atgctataaa caaaaacgaa gccaaacgga    21960
atattcaggt tctagaccca gattatgttt cttcctttgt taatcagctg gaacaggagc    22020
tgaccaaatg atcgaaaata aagaatccca ggacggaatt ttaactccgt ccacaacatt    22080
tgatttgaaa tatatggcga tattaccaca cacgcctgaa ggcggtactc ccaagcctta    22140 tgaccttca tcgttgttc aagaattcaa cgtatatcag gatcttggtc tggaagggaa    22200
tgcttcaccg tcgctgacag ctaatattct gatcaaagaa ggctgggata tattggatac    22260
gatgccaatc ctcggaggtg aggaagtagt ggtatcgttc aaatcgcctg cagcttctga    22320
ttacactaca ctttcattac gagtcagtcg ggtggggaga gttgctgacg aatcgaactc    22380
ttcttcgaaa aaggcatttt ggttacactt ggtgacaaca gacgcgtatc gagatagcat    22440
gttgcgtaaa tctgttggat taagcggttc ttattctgag atggcagcta agatctttga    22500
gcaactgaat tcacgcacca aatttgaaga catagatcct tcatatggga tacaagaaag    22560
gttcgctacc cctctttggc ctgtactccg ctccatagat tatatggcca gccgtgcata    22620
tgacgaatta ttcatgccgt tcgttttcta tgaagacttt acgggttatc acttcaaaag    22680
catgacaaca ttgttcaacc agggcaacca gtctatgact gctgaagaga acaagaggc    22740 aagcgcggaa aagaaattct tccgtgatcc tcaagatgcc ccgttaatgc aagacaataa    22800
cttcaactcc gaacgtttta tgcggacgat catcaaggct gaaagaaac tggcgcgtga    22860 tcagtacatg gcgaattatc gggatatctt ggcagtgaac gagcgcgtgt atgactttag    22920
tacaaaatcc acgacagcga cccaacgcat ttattcagaa tggtttgaca gcactgctca    22980
ccttgatccg ttccctttgt tctctgatca attcgaccgc gagaacgtta ggtacattga    23040
agcgcaaccg gatggtgccg aacaaataga ttacgcacga cgcgttatag aattcagcct    23100
cgcgtcaacg gttatgcgtt tactggtcgt gggggataac cgtctgaatg ttgggcaggt    23160
ttattatatt gaagatttgt cgaaccgccc gaaatctaat gaaaacattg ccgagttaag    23220
taagttatca acaggccatt atatcgtcac aaagatacgc cataagattt cacgcctgac    23280
aaatgattat caatgcgtcg ccgagattgc caaagatagt atgatccaga aggtcttacc    23340
gcctcagact ggtcaaactg tggcttctac accaactccg acgccaatag agaaaggaca    23400
```

```
agcccagaag gtctgagagg tgacaaatgg cagataacaa tcaaccgaca ccagggcagc    23460
aagacatcgt caaggttttg gataaaatca aaaagaaat  gatggagcgc aagcaattgc    23520
gcgcccaatc cgagacgaat aaacagctcg ccgatgtcaa caaacaactg caatctctga    23580
agacacgcca ggcgtctaat caggagcaga aagtcccgcc aattaaattc catcggtga     23640 atgatattgt tggtgggttt gtccgcgtca gtcctatttt cacaagggat tacagcactt    23700
ggatgaaaga caccgtcagt ctaacaaagg atggcaatga agaactgatg cgtatcgcca    23760
ccaagatcga aaaatttggt gaagcggcga atggtccggt tgacgacatg tcagttgaat    23820
atcttgacat gatatcagat caattaggtg cggccaacga agatagtctt gaacgccttg    23880
atggattaaa ggataagctg gcgttggtcg gaggggagat cgtaaacctg actgacataa    23940
tgcttcaaac acataaggac acgctggatt tcaataaaga tgccagtaac gaaactgtta    24000
cccgcctcga cagcattgat gacaaattgg gatacatgaa cgaagatctt aatgatactc    24060
tgacacgtat ctatgaaagt gatcaaaaat atagagaaga agagaaattc cgtcgtggcg    24120
aagaaggtaa ggaaaacaag aacaacccag aggctggttc tatccctccg tctgagccta    24180
aacaagatgg tcaatcttct gggttaggcg cggcgctggg ggcactcctt ggactgggcg    24240
cgttaaaact cctgatgtcc ccattaaaac ttgttggtgg cttcattaaa ttattcatgg    24300
ggtttggtgc tgggatcggc gggttgcttg cgcctctgaa agcagcaacc aagatgcttc    24360
gagttggacc tctggcgtta ataacatctg tatttgaatt cggtaaaggt ttctttaatg    24420
ctaaagaaat ccttggtaaa gcgcaagtat cgatcgttga tcgggttcag gcagggataa    24480
cagagctggt cggtagtttc ggggatctcg ctgattgggt tgctgaaata ttcggatgga    24540
acaatgctgg gtttggaaag gcgttccgtg aacaagtgct gaaaatgacc gaagcgcccg    24600
tgcgttggtt gaactcgatt gttgattggg tcaccaacga tttgtttgcg ggtatcggga    24660
agagtacatc actgaccgaa atccctggta aacttgcaga caacttacaa ggccaattga    24720
taaaattggt tgattgggta acgggcggga tatcaggatt gattgatgat ggcatggcgg    24780
ctgcaaataa agtcgttgaa gatatgaaga aaggatttgc ggaaaacgtg aagaaaccat    24840
tctttaatat gttgaatgcc ataaccaatg ccatgtttga tatcgtggat aaattcgtga    24900
gtatcatacc tgatgctctg ggtggtgaag cagccaggaa caaaatggcg gaagcaagac    24960
agtctatgct aatcagccaa gacgataagg ctcctgagaa tgcgtctacg ccgccaagca    25020
gccaatcacc agcacaaccc aatgccaata tcagcacgtt aactccaatg ccttctgggg    25080
tgtcctcaga cgctgtcaac gttacggata gaacttcaca attgaaagac gcatacgcag    25140
ggattggggg aggtactctg ggcgggcttt atccggttca aggaagagca gccaataaca    25200
tcgaagaagt taaatccgcc tatgctaacc cgccagccag tgttgtggtt ccagtacaac    25260
aaaatgtgga caactcgaag aaagtcagta cgacgaacaa cttcaatagt tcacagttgg    25320
agccgtccaa ccgtactgat acagggcgca ttctctggga ttggtaatca aattccgtgg    25380
gcaaggatta gctcacggag ttttccttt  gtgtattctg tgttttcatc aggaacaact    25440
gaattggttt tctttaataa aaaggactca gagttccaat agatgtcatc cttgagtatt    25500
gtatcatata aatggatgaa ccccactact ttattcaatc caacgagaaa ccaaattgga    25560
tagcgtttaa caataatatc tgtcagtaaa ggtggatgcc cattaccatt tcctttgata    25620
tattggataa aattcacgcc tctttctttt atctcaggga tcatatatct ctcaaaatgt    25680
tcaagaaaat tatatgagaa gttgtcatac aggcggcgat attcattata attttcttga    25740
gcctgtcttg taagtaatgt tgtcacccac gtctttggtg atttaacaaa gttggcaata    25800
```

```
atataatttt ccaccacttc accttgggaa gattcgaacc gacgagcaag tttagcaaat   25860
tgtttggcca cgccctgttt agaatagaac gtttcaaact tgtaattgtt catcggccca   25920
tacaggccat aatcaaagtc ttttgtggtg aaatgcaatt tgatcgccat atagatgcaa   25980
taaacgttga atgcccttc atattgcatt ttctcccact cagttatcat ggagtttctc    26040
cttgcgtttc tgtctttcaa gtcggcgacg ttctgagcaa aactggtagt actcagacag   26100
caatcctttc tcttttataa agagaatggc gtttcgaaaa gcaattccaa ttttggcata   26160
tgacggcgga tttttaccaa ccacgtgatc tctcctctgt gcgaacgaaa cgttgaaact   26220
cttctgtttt tccttggcga tgaataaaca ccaaagccaa aataaaacga cggaatgatt   26280
ttgggataag acgataaccg tttgtccaat tataaacgac atcagaacaa ttcatcatct   26340
tcatcatctg taattcagaa actcccaatt ccctcataat gtttatgagg tgaagagaat   26400
cattgtcttt ccttggtttc ttatcaataa gtttcataat aacacctggt aatgatttct   26460
tggaattata ctgctactgt ctttattgaa tggggttccg aagaacccca attttcatgc   26520
cgcttccaac aacaccaaaa tattttcgat atatgctttc tggatagcat agacttcagc   26580
cagtgtatta gcgactttct tgtctgtgcg tacttcaacg agacgtggaa ggaatagaga   26640
cttcatggcg tcatcggttt tatcctgtac gccattagag agaacggcgg caatcttacc   26700
aatgaagtcc tcttggtttt cccacattcg tagtctcaac tcatccgaga tccccgatac   26760
gccaacaact aagaggccat cagaggtctt gcagaggaga gatccaaatg tcttggcgtg   26820
cttccctttc ttatcggcct cgttgaagcc aacgatttca aggtcacatt ctacttccat   26880
tttcagcttt aacccttcag atgatgttcc atcttcccaa ggcatatctg cggccttaca   26940
aatcgtgcct tcttcccgac gagccaaagc gtctttgaag tgttcgacag cttcttcaaa   27000
tgaatgaaca acacgggttt cttgaacctg aaccaggccg tcatcccctt cgaacaactg   27060
ttgtatgata tcaaaacggc gctcatatgg ggtgtccaca cgctgagcat tgaaccaatt   27120
atcatacggc acaacgtccc ataccccgata gatcaccttg taacgatctt ccaggggttc   27180
acccgtttgg ataacactgt tgagcttacc attgccgata gcccgaggca acactgtatt   27240
cgttttcaaa tcaatgacga gcagttcacc atggaagacg cttccaccaa tccccgcatc   27300
gtagatcagg tctttgaaaa ccaatgatag gttatcaacg gaaccacccg caataagaga   27360
accggaacga gaacgaatct ctgggtctct tccataacga cagatgatgt tggcaaacat   27420
gccatctgac ttcagctggc tgaagacgcc gcgcttgaag tccatcttct tcagcaagtc   27480
aatcgtcatg ttatcataac ggtgatatgg aaggatatta atcagacgcc ctgtaccacc   27540
tgctgcgttg aatgctgcgt ttataccttt ctcggcaatt cccgctttga tgtctctgtc   27600
gagtataatt tgtatcaggg tatggtaatc cggatggatt ttggttgcag ccttcgcaag   27660
ttcttgatct gccttcatcc caccgatctt gcgttcggcc atcatatcga gaacatcata   27720
aacctgatcc cagctaccaa caacgccgcg cgagagcatg cgagggaatg cgtttagatt   27780
gaattgagtg cggtaataag aacgcatcgg gtcgtagacg tattgaagga aatcaaccaa   27840
ttctgggttg tttctgaacg cctcggtcag cacagctttc ttggcgttgg tgcctttggt   27900
atcgcgaaga ttttgaatta tttctaaaag aggaagcatc atgtgtctcc agggttattc   27960
gtcatgctat tataacccta gagacttcaa tagatttatt tgctgcgtct ttttctggcc   28020
ttgtcaacaa tctgaagaac atccactcca tatttgcgca ttcttctatt attgatccat   28080
tcggcccaaa ccggttgaaa aagaataatc aagatcccga aaaataatat tgcagaccaa   28140
```

```
atataaaatg aaatatcttt catatgtctt ccttccaaac aaatccatac ttggaaagat    28200
aatctggttt cgttccatta cgagttcgag cacgatccac gatagattct acagtttcta    28260
ccttgtgaat agggacattt ccattgttca tatactcttt aaacaacctg tgaagatata    28320
tcaaaaattg tttatcgtaa gtgtcgttgt aattccaaaa ccatacagca gcctgatatc    28380
catctttaca tgctattttc aaataaaaac aatttgattt tgatacacac gattctatga    28440
acggccaacc caaacctttc atgaaatatt gaaatattc ttcaggagta gtgtctgggt     28500
ctttgtggtc taagttgaaa tcatctatgc taggaaccaa acttttggac acacgactac    28560
tcagaataag ttttatgtct ttaatatttt tcgtggtatt ttctggttgt aaatctgagg    28620
agacggcctc aacaacccgt tttcccaaag attttttgat tcccataacg agaatacaga    28680
ccccaaccat actaagaaca gcaatcaaaa tatctgttga gtcaataatg accataaatc    28740
ccccaaatga aggggcatat gccccttcta tattattttg ataaacttgc cagataattg    28800
tccgcttctg ttgctgaagg ctattggta gaataattgg aatcagcgat ttcagcttcc      28860
cgcaggatag catcaacatc tacattaatc attccagccg cgtaatcgat gtcttccggt    28920
aaagttaacc caagatcatt tgattctttc tgaattcgga ccaattcgag attagactta    28980
acagcgtcca gtttgtcacc taattcaaca attgccgaat tcaatttcac actgccagat    29040
tcgatctctt tgactttatc cagaagagct tcaccaatac gacgacggtg gagtatgatc    29100
aaggcttcg cgcgggtagg agttactccg cgagcgatcg catctttcaa aatgttttct      29160
cgcttgatgg cttcagccag attttcatca gcggtcttct tcatcttaac gccatggtgg    29220
acattggtta cacgggcttc ttctaaacgc cggatttcat cagatagttt ccgtgcagcc    29280
agattcaaac gcttctcagt atctgtgagt ttatccaatc ctgcagttaa attggcctcg    29340
acagtgctga acaggcggtt taaaaaggtt ttcagtgaca ttaatatatt cctcaattat    29400
ttcttgggtg gtgtgacaga ggtgaaggac tccttccaac tcttgaattt ttcaatcagg    29460
gattctttcc ccatctcacc gttggaaaca tcatggatat aagcaaatgc gtcataccca    29520
tatcctggta aagcagaaca gattcgaagg tgaaccaaag attctcccac agaaaccaaa    29580
taatgatcgc gacgatcatt cagagcataa tgattgtcgt gaaacttgtc gatgatggtg    29640
cagtttttag gctcaacatc aatcgctaac ccattggcct cagagccgcc gcgcccaagc    29700
gtacaacctg gaataatgt ttctacgagt gtgggcattg tttattcctt ctgtttaatt      29760
cccatgtatt atatgggtaa acgtttattg aattatttgt tgtgatagcc aagagctttg    29820
cggactttt cacggtcata tgtatcgacc tgaattgctt cacgattaat ccgacgcctg      29880
tgatgtcggg tgagcgcttt atacacggcc ttggcctcat ggtatggcag acaatcgaaa    29940
caaaaaccga tatcgactct ataccctgcg ctgctattga ctgtatatgc atatacccct    30000
acgccgttat agatgacagc atcgataccg acaaagcgtt caccattcca ttcaacgtca    30060
tcagcgtcga tggcatcaat aagacaacgg atttcgacgc ttaggggttt ccccaacaac    30120
cagttaaaat atttgcgcat gtcatttact catcagtgaa agaagattga ctttatctga    30180
acgtgcgttt ggtgagtaat gcacgtcctg agagtgcctc ttacagcacg gacaatcctt    30240
ggtggcaatt acacagggag ccttatccac ggcatatccg gcttcttcgg cttccttcac    30300
ggtgttaaat ggcaagtatg cacttgtgcc ttgccctccg catgaacatt ccattagaaa    30360
tcctccttgg taatgaagag caaatcagat ttcagatttt ggcgcttgac acggcggaca    30420
tgtcgatgct ccttttaat accgtctgaa cgttttgatt tagagcggcg atttttgtat     30480
gtgtccgctg ggtacttgtc atggcctgga caacaagatc cagggtagta aacatccaag    30540
```

```
atttcccgtt tcattaacgt ttcctcttaa atgggatgat cagggctatg attaacagca    30600
tagctgtgat cactccgcat gcgataagac cgaatgcaaa tgctttcaaa acaaattgta    30660
aaagaatcat aatttcctca gttttgccct tgtaatctga gtttgtttaa tacctttgaa    30720
ttcggtcaat tctttgacac gacctcgaat gatcatatcg ccttctaaaa actcggtttc    30780
catataggaa gtcttccatg taatggtatt gccttccttg gttttgaaag tatacagata    30840
cgtgtcacca taatcagatg aatacaggaa aatccttgct tcaaatttga cctgtgcttc    30900
taacatttca ccaacttcac caacccaatt tgatacagtg cgcgtttggc ggggggtgtg    30960
gatataatca taatactttg ctgctcccca acgaactgtt gttgagtctt taacaaggtg    31020
ataaccaggt tcgcacatac gtttcagccg gacgttgaaa tcgttatttt cagacaacga    31080
tgcgatgaaa agcatcatat gatacatctc tgattgagca tcttcacggg ctttaacagc    31140
cttgttatag aatatctcaa tgtcagaacc tttctccgga cgagtgccgc tagagatatg    31200
accaagaacc cgaccaaaat catcactttt aatgctcagg ccggacagca aaacctgaaa    31260
acatttacac aaatatcctt ctgtgtcaac ataatctggt tcattaaccc gataaatccc    31320
ttctgggtca tcttcatcgg gggtaaacat ttcgtgaata gacatgtaat aagacataac    31380
cgcatcaagg gatttctgat gcgggacata atgatgcata cagctgctac ccacgagcat    31440
ctgtgcgcca gattgttcgt tacgaacgac atatgtgtta tgacgacgca cagatttgtt    31500
gcaatgctcg caccaagata cgttttcagc ttcaaatctt tgaacgaaat ttgggtggat    31560
gtcatctgac agtttattca gaatgacttt tggatactgg tggttgaatt gtccaatgat    31620
actccaccca ccataagaaa cggggcggtc gatgccttca ccagttagag tacaatcttg    31680
ccaccaacga taaattttt cgccagtgat agaatcgcgg tgttgtgttt tgtatggttc    31740
actgaactca acaagaggga actcgagttt caggccgttt gccgttcttt caagtttggc    31800
aagacgttcc ttgaagcgac caatgttatt aattgggatg ctgaaggtct tggcttttct    31860
ttttgcctct ccagatgtag tgaaactttt ccaatgtaag ttaaatgata gccgcaagtt    31920
ttattgaagt aaagttttat tgaagtaaag cccaacaaat gttgggcttt aaccgatatt    31980
attcatccgt gcgatcaggc gcggcgttag gatacagcga ctcataaaga tcttggtatt    32040
tggcgctggt ctcgatggtc ttggtataag ttccaccagc gcgatcggta acgactttgc    32100
gcagatcaac ggctttgatg cctgtttctt ttgccaattc agccagggct tcggtaacaa    32160
aggtctgttc agacttgata cggatctggg cggcacgaca attttctaaa gtctgcatca    32220
tcttttgacg cagttttgga tcagaaggga gttgataaaa accaaatttgt tcaactgaca    32280 taatatatcc tcattaatga cgagaaccga gtggaccgat actggttccc aaacggcgca    32340
ggaagaaata aacgatactg tgaaaaccaa acttaggaat aatatcaacg ccttcaacat    32400
tgtaatattc ctgagtgttg gtctgtactg gcaacggaaa agacggaaga tcaagctgaa    32460
ccaattcacc tggttcgcaa tgtatcttga cattcttacc ccaataccga cgattcttat    32520
aaaattctag agtctgctct gtagtgagtt tgagactggt ttctccagac tggcacacct    32580
gttgtgccgc ccgaatcagg tcagctataa atgcaacatc cgacatgatg tgctcctggg    32640
ttaatattca gatcatagag attatacccct atgatcacca ttattgaagt taaccgaaat    32700
tccaattatt cacggtctcg gctttcttga catcatttac gtcgcctgtt ttgtttaagt    32760
catgtttgat atgaacattc tcaacataac gggcttcctc ttctgtcagg tctcgcttga    32820
cttcattcca atccaagtca aacaatatct gtttatcttg atccataccg aacaagaacg    32880
```

```
atttgagttt ctgtttattg gcataacggt ttttcaagat agacgctcgg gctttcttaa    32940
cagccgccag ttcatcaggg gcatagaacg ccatgatgaa gtctgcaacc ttcggaatac    33000
cgatagcatc tgccaggtcg ctaatatcac catcagtcgc cgattgtttt tcacggttaa    33060
attgcatacc tgtccataca gggcaatcaa attcaaatcc aagcgcacgg aattcacgcg    33120
ccaccgacgt ataatacacg ttggtgttct gcattaaatg gcaggaagg cgagaagacg     33180
ctgattcacc caagtagtct ataataatga cgtccggcgt aattcccgtg gatgtcgcat    33240
aatcaaggat atcgcggcga tatagtcctg tatgcccagc gcctgaagga tattccttga    33300
taacaatatc acccttcatg gaaccgtctt gacgagttcg caacttttgt atcgtggcga    33360
catattcatg tcgtgagagc ttctctaagg actcgaagtc cctgcgcatc atacgggcat    33420
caaggcggtg acgccagacg ttctcagcca cttctagggt gaatacgaat acgttcaacc    33480
cttgctcgga gtaaccagca gccaaatcaa tcagagttgt tgtcttaccc gcattaattg    33540
cacccgtcac gatgttcagc gttttcttac caacaccacc acgagtcgct ttgttgaata    33600
tctctacagc gaaaggaatc ttcgcttcat tagagttcat gtggtcgtat tgttgttcag    33660
ccatttccca atagatatgg ccaagataag aatcaaaact tatcgccaac gcctcttgta    33720
ggagagttgg aatcgtgttc atctcatctt tacgtttctc atcaccatag atgttgacgg    33780
cgtgtttgat cgcattatga acagcttict gccgcgccca actttctgtt tcttttacaa    33840
gccattcctg atggaatgtg ttgtcattga tattctcaag agcagaaata gcttgttcaa    33900
atacgtgttc gttgagcgaa gtcttttcca gcataataga caacgcttca accgaaggac    33960
gagcattata ttcgcaagtg taatggtcaa tgagaccgaa tataattttc tcgccttcgt    34020
tatcgaaata atcggctttc aaatacggct ggatctttct ttgatattct tcgttataga    34080
ttaattggga aagcacgaca gattcgagta acattggcaa ctaccccacc aaaattttgt    34140
tgtaatcctg agcattttgc tgtatcagat caactaagat atccccagac accacagtga    34200
acaagtcatt ttcttttcaaa ttaacaaata acaaacgcca tggtttcttc aatatatctg    34260
ttgtaaagga taaccgaggc tctccattat ctaaatggac acccactttc cctatacgaa    34320
attgaacgcc acggaatttg ccttccgtta tttcgattat tgctaactga tcagaaccag    34380
ggtcgatgat tttgtaatta acgggggagt ctcctccccc tgcaatatta ctcggttgtt    34440
ttgatgacat tatcgaggcg ctccagcata tctgcaggca taccgaact ctgagagata     34500
ccgaacatgt tgttcacatc gtcaacaaag tctgggtttt ccagcagcgg ataccagaag    34560
tcatccccca gctctgcctt acgatatttc ttttctttt ctggatcaaa cccgcctttg     34620
gcagtgcgtt gataccaaga gccactcacc aaatccacat accccagcat gcgcgcaatt    34680
tctaacatac cggaccaacg gtcaataccg ccttcataca acacagtgac agggaacttg    34740
gcttttcac ggacaaagcg gcctttcata atgttgactg taaactgcca tcccaaaagg     34800
tcttttgtctt ctttaacttg agaacgcgtg atgaaccaca attggttaga agacaggaac   34860
ccctgtttac cgcctttgat gttcggctcg gcgtattggt tcccgatttc atcatagtac    34920
gagttgatcc ataccaaaac gaatttcttt tcagtgacca acggggtgat aacacgccaa    34980
aaactattga gagcgcgagc gcgggtcata tcttgtgtgt cttigcccgc tatggcatca    35040
tcaacttctt tggtagacgg caactggctg attgagtcaa tgaatacgat gatcttgtca    35100
cctttctgtg catcgttcag aagctgtgtc agcttgatct tcgtcttttc aacgttttca    35160
atcggcagat acaagacacg gtccatgtca atacccatag atgtccagta gttttcattc    35220
gcaccgcctt ctgaatccgc gaagatacaa attgcatcag gaaacttatc catgtaagcc    35280
```

```
ttaacatcca ccagcccaaa catggttttg aatgtacgag aatcccccac caactgtttg    35340
atgcctgata tcagaccacc atcaatacga ccggaccagg ccaaattcag aataggaata    35400
cccgtactgc aaataatgtc aggcttcagc gcatcggtct ttgacagcac ttcggcattc    35460
gggtccagtt tctttgctgt cttgagcatg cgagccatca atgaatcggc catttcgttt    35520
cctcttgctt gttgatcgta attaataaat cggtgcccaa gactttcttg gacaatatat    35580
tgattgcttc gtgaatcgcc attattacg ggagttttc atcgttaatt tcggaacccc      35640
cgcgttctgt taaatacata ttacgcagac gattgtgctg tgccctgttg acacaagaaa    35700
cattcaatgc gatattcagg atatacatca tttgttcagt tgtaacatcc tttggaatag    35760
catgaacata atatatcgca tcttcaaaat agatatgctg caatgactct ggaatttctt    35820
ccccgccaaa agcaaaatct tcaatgcgtt taaaagtgt ttccggctct ttggttgtaa     35880
tatgttgtgt tacagtagcc gcaccatctg gctctttctt gaaattggtc gcaataacga    35940
catgaccgcc tggtttaata aactcagcga agttctctgc catgtacggg gcatgttccg    36000
cataatatga tacgacaact gtaaacatta gaactccaga gtcagagggg tttcggcaga    36060
cttgtcatag ttcgcaccgc cagcagcacg tagacgattg cgatcgttct tgcgcttgtg    36120
ggccagcata taggtttcgg tgtccagatc caaataacca caagcctttg ataaaaaccg    36180
cacaaaacgg ataacatctg gttgaaccat aaatgacgta aaacattctg tgaccgattc    36240
cagattggcc gattggtcta tcactcgtcc gtccttgaag aaaaggtcaa tctgcatttc    36300
aactgggaaa gcagaaccaa atccagataa aatggaagac aacataaaat gtaccacgtc    36360
caccaattcg tagacagctg cttctcggtc atattgtatc ccaccgccat agatttcca    36420 gtcctgggtt gtttcgtcaa gaaactctgc ccactcacga tagatggagt tcaccaccgc    36480
cacatgagtc caatgtttac gccactcttc cccaaaatag gccacgttgg tggccttttg    36540
aagttcgagc agacttttga tatgctctgc tgtgatcatt tccgttccct ataaaatttg    36600
acgaatggtt gccaaccttc aaatgggtta acaaattcat aatcaacttt catctcatca    36660
atgaaagcct ctatgtcgtc ctctatgata ccgccgcgat ctgcctttga aatgcgggtg    36720
atgggacatt tagtgctcag cgcccattca tattcttgag gcgtccgtag atcactcaca    36780
atataatgaa tgttaggatt ctgttcaact aatgggagtt ggtaacgctt aaagaaagac    36840
aaaaacagat ccggttggac ataacgaagc cccgtatcgc tgccgagatg aagccagatc    36900
tgccttgggg ttaatccctt ggggttatct gggtgaacat atggcaagtc cttgatatcg    36960
tcctctactt cctctggcaa ccaaggatag atgtaatgag ccacccgacg caactcgtcc    37020
gagaaagata agcgctggat gtccatatca ccctgtaaat ggtgatagct gatgagggac    37080
tccaaacaga agtccttgcc ggagcgcttg cgcccgtaa agaattcaag gttcggatac     37140
atcatactgc accttccaag aacttgggat caacgatctt gcggtcaatc ggagaatgag    37200
cgagcgcgat gttcaaacca tgatcctgaa tcaggttcat gttgatgagc ttgtcgttca    37260
gtttgcagta caggcagtac gccatctgca cgatcaggcc gcgatccgcg ccgtactcct    37320
tcaggtgagc gacaacagtt tcccacgggc tgccgatatc acagtgatga agcacaccag    37380
tgaacagatt gcggatatgg ttctggttgg tcacgttcgt gaagtagatc atggagttga    37440
tgaaaccacc agtgactttt gtgtctttgg tgatcttgcc aagctgcttc tggctgactt    37500
cattgttgta gtaatgaaga ttgttagaga atagcttgta ctgaccgaca tcaacatcta    37560
acacctgagc aatcacttcc tgaagaatag agaactcaat gaagttgatt gaactcatcc    37620
```

```
cccacagaac atcctgtgag cggttgatga ccgtcaggtt cagacgacct tcaacgatgg   37680
cgaacaacag agccaggtta cacaccatgt ccttagtctt tgcttcgccg ctctcgctga   37740
acttcgccag accagcatcc gaatctagag ccggatcata gatggtgagg tacgcttgac   37800
gagtatttgg gttcttgcgt aggcggttga taacgctatc cagctggcca tgggcgtaca   37860
gacgcggacc ataagcggct cgccatgtat ggccattatc agagaagttg gcggcgcgag   37920
ggaggacacg ggacaagaag cgcacatcat cgcgcccaga cagaacccag aaggtctcgc   37980
cgatggcagc aatagccgat gagttgcgtc cttcaacaga cagccaacgg tcgcggatgt   38040
cagagacggt gatcgtcacg ccatcaataa aacgagtgcc gtctgtgttg atctccgcgt   38100
taccagggtc agattcaatc ccgtgctcac ggatagccaa gacagcctgt ttcagcatgt   38160
cgttgttgtt aattgctttg atttccatca ataaatactc ccaaaatcac gattgagaaa   38220
cgcaaaaaca gcctgctcta cagtcaggcc atcggacttc atcatacctg cgggaacggt   38280
agggaacaag cctttatgcc gttgacggtg atcatgaact ctctcccact tctcgaccac   38340
cagactttca ttgaagtctg cgccaccgtt acgcgattta acacgggcaa tacaggtttc   38400
aagaggggta tccataaaga ggacgaccaa ttcacgtggt gggcgtgtca ggcggggaat   38460
ccaagaactc aataatgtag acggaatgat gccttcgaaa atcacatcat atttcaggta   38520
ttctggttgg tcagcaatag acaacgcgaa caacatctgc tcagtatcct tcagagaatc   38580
aacccctttg gacttagact tgtcatattt accgacacag acaatattgt aagatggaca   38640
aaccgtgagc atgatcttac tgttatgggt tacgacatac gcctgaggat cattctccgc   38700
caaataagaa ggcacagtag acttaccact accattggag cctttaatgt aatacaactc   38760
tcctcgtgcc gaatattccc cttctacagc aggtggtttg acaaacaaat gcacagggcg   38820
cttcaacagc ccttttgagcg aataagacat gacatgctcc aataaacaaa aggagctgct   38880
attatagcag cccctttatc tattgaacgc ttctgaatta aattacgcag cagctttcgc   38940
ttcggccaac gcctgaggca accattcatt gattgctttc accagagatt cggcatcggt   39000
ttctttgatt ttctggcgtt tggtgaatga tttaccattc acatacagac tgaacccca   39060 gccgccggaa acgattggcg ccagatcaac ataagtattg gtgcgggcgt gtggattggc   39120
ttcatctgcc agttcggtaa cagggaactg gaaccagcgc atatccggat tcacatagct   39180
caaataaacc ccaggcacaa cccctgattc aaccgcagcc aggataggac cataattgga   39240
tgcgcgagcc gcttcaacca tttcttcacg cttgttatga cgacgcttgc gttcttcggt   39300
agaagatgca gggcgcattt cagaagattt cttggccaga accgccttcg cgttcgctaa   39360
agcctgatca tccttcggat tttcaacgtc ggcgattgct tcagcaacgg ttgtgcccag   39420
catacgacgg cgaacttctt cagcacgggc ttgagcttct tcgtcaagaa cttcttcgcc   39480
ttcaactacc agggaaatgg aaccgtcttt gttgacttca agagaaccgt cttcgacggt   39540
ctgggaattt tgatcaccga caggttgccc aaccgtttct tcggcgtcaa tcaccggatt   39600
tgattcaccg tcgccctgtt taaccccgc atcttcggtc ggtttaactt tttcggcttc   39660
agcgcggtca agagcttcga gagtctcttc tttctcttcc tggctcagac cttcgatgag   39720
ttcaaagcca ttggctgact ggaggacgcc ttccatcata cggcgtaacg tgacgttgcc   39780
gatgataagg tctgcacctt tgatttctgc ttgaagatca gcagcggttt taccatcaat   39840
ttcaaatttc aggccggact cgatatgaag aatataggac ataataaaaa ccctttttgtg  39900 tagtaacctt ctttgcagt ctaatgttca actgtgcgtc tggaacatta atatactgcc   39960
tttttagatg atgtaaacca ctttttattg aaaagttggt taacacttct gtgttagaca   40020
```

-continued

```
acggaacgct gtatcagcgc ggactggcgt gaatattaac tttgtatatc aatattgaaa   40080
actgtttcag gtggccacat ggcagacaac tcgatttgtg tgaatttggg ttgaacatac   40140
tggtccaaaa cttcgtccca gagagcatgt tctatgttgg caatcaacaa ttcgtcgtcc   40200
actatttcga cggaatgaac cactatccgg tggtcataag tcaaagcatc gctcacatga   40260
tcattttctg ctctcaggtg ctgcattatg aaatattcga ttacagattc cagtaccgtg   40320
ttcaggcgaa catatttctt catacagccc cctgcttgtg ttacaggtag aaattaggga   40380
tttctccgga ttcaaaacca aacccgttaa aattctgctc aacgtgtaag cgaattttat   40440
tcaccactac ctgacgatgc tcttcttcca tacaacgttc aatcaaagaa tacgctgtat   40500
atgacagact gttgaacaat ctggaaataa caaggcaatt ctcttcattg taaacgactt   40560
cagtatggat tgcgaaagcg tggtcttcgt cggtaagaat tttacagcct ttgaccacaa   40620
atggtttttc aaagaaatca cgagctgaat cagtgccaga ttctggcatt aaacggaaat   40680
cgccttcttc gccgaaaacc gctttcagat tttctttact gaattccgct tccatctgta   40740
tacgtttgtc ggcaagatat ttcgccgcaa agtagaattt acccactgca tcattagcag   40800
cgcggcggtt cgtagcggct tgggtataac cagaaacgaa gtcttcaatg aattccaatg   40860
cttctggttt gccaaaacga atttcgtcgc ccagatccaa gctggcttcg gaatcaagtt   40920
caatacccat aaccttaaga agatccgttt cattcagcct gtgctgatta acaattgtt   40980
ccttggaata tcccaactgg ctaccgagtt catatccggt tttaccaccc gaatctttat   41040
gggtgcgatc atatcgaacg caattagaac tgaattcaat accaaaaata cgatgtagct   41100
gtgacatatc ataacctcat gtttatagaa agccgttcgc gaattatcac gtagaacggc   41160
ttttagaact aaccattttt gtgtttacga cgtgcgtcct tccaaacaga catctgactc   41220
tgtttctgga atcgagcagt acgcataaac aaaacgacct cccaatattg cggttcaatt   41280
tcataaagtt gtgaacgaaa ttgatctgcg cggtataatt tgacacaatg attgtacaaa   41340
gggtgattcg caaaccgctt tagcgcatcc caggtaagtc tcaaacgtgt tttagaacga   41400
tatgcccgtt catttctcaa tttaatgaga tcttcaaata ccaacaatct gagtttaggc   41460
ggtaaataat ggaggtttag gccataaaga taggtcacac cacgttcacc gaatttcacc   41520
ccgtccccct tcacaaaatt gaagaagaac accagaggat acatatccca atacgggagt   41580
tcatctttag tcagcgcatc atatttgaaa taatacatgc gaccaacaat ataacgcaca   41640
ccctgaacag gacgtttatt ttcagcgaat gctttcatca tgtgattcgg agataagtta   41700
gcatctttcg acacgcgctc cataaaccac acatgagaac gacggatatt acgcttcgct   41760
tccggcccaa aatgttgacg atatttgcgg atgtaacgct tgaccagttc tggggcgtcc   41820
atctcggcgg gaagcaacaa cgggtcttct tcacccatag cgttcttagc catttgtcaa   41880
ctccttataa atatcaacag atatattatt taaatggagt cctcatcgtg gaagactatc   41940
gcaattttct aacgcaactg cttcaacggg gtatttcccg caagaacaga tttcgtgtta   42000
caattccgtt gccgcctggg atatttgatt ccaatgcaac actagcaaat gatgggaacg   42060
cgtatccttc atcttcatca tttggggatc tgttcaaaca aagcgcccgt attgtaaacg   42120
cattcttttgg agggacaaac caaacatctc gttccctgca aatgatgtgt atggtcgcat   42180
ctttacctgg tacagggatt gacactactc ccatgaccaa caacggcaac cacattaaaa   42240
tgccgaacaa caagacgaac attgatctgg agttgtcgtt cctcctcgcc aacgattatt   42300
atgaaaagtc ggtcatggac aaatggaaga atctgatatt cgacccatac acaaccaaga   42360
```

```
tgggttatta tgaagatttc gtgaccgata tttgtataga acaaatggat acagaagatc    42420
aggttgttca tcgcgtttat gtgactgagg ctcaccccat caacttcagt tctatagacc    42480
tggataaaag cgccgccgat caatttaatc agtacaacat ttccttttct tataacaaag    42540
tattatcgga gactgaatat gaaacgcgca gcctcgccag cgattttctt cctttgggta    42600
ttactgatgc tcttgcttcc ggagactggg aaaccgctgc gtcaaaagcc ggacagctgt    42660
ataaaaagat caaagaagga aacttcacag gtgaagccct gctggcttat aagcaactcg    42720
atcagcttgt aaacaatctg ctggtatca gcttggctga tttcgaaagg atctctatcg    42780
gcatccagag ggatatatta ggcaatgata acctgacggc gtctgagaag agtagtctgt    42840
tgggattgtt acaggatgtt gtcaaaaact aaaaagcccc gaagggggct ttagtgaaat    42900
tagtcttgct tcaggaactg ctcgaactca tcaatggaag ccgtctgttt cgcatcggca    42960
ccaccattat tggctggaac agattgctgt gcattagaag gctgagattg ttgttggttt    43020
agactttcct gcgctgttgg gcgctggggt tcctgagact gggtaggcgc atgtgccata    43080
gtagaagcac caccttcaac cagaggctga ttatcaggga tggccagaac tttgcgcaaa    43140
cgttttccca gatcttcgta cgatttgaag ttggccggat taaagaactc aaacagactg    43200 tgttctttt cccagatctc ttcaatgtat tcgtctgtcc ccaaaggtgc cggagtatcc    43260
cacttcacat tggtgaagtt ggccaccaga cctttccagt tgccgaactc tttctcttcg    43320
ccaaagaggt tcagaatcag gttcgcgcct tcccacatat cgaacgggtc gaatttaggg    43380
tcagttgaga acttaggatt ctgagccgaa tccaggattt tcttgacggc attaccgaac    43440
tcaagcaaga agaccttgcc gttgttttcc ggattgttgc catctttgat caccaggatg    43500
ttggcgtagt atttggtgtc cggcagacgt tttttgagaa ctgttttcag cttttcatca    43560
ttcgtttctt tctgttgtgc ccacagagga cggtcatggt cacgaacagg atcatcgtta    43620
ccgaaagtct gaggagagtt ttcgatatac caaccaccag caccctggaa tgcgtgtttc    43680
atgatcatgg cacacggagt taacacagca tcttcaggga tggtgccttc ttctttagcc    43740
ttcatgtcca ccaaagggat cgacaggaaa cgaatgatgt tttcagaagt acccttatca    43800
ttccaggtcc acttccagat gcgtgggtca cgaccgccac caacacgctg gccttgctga    43860
gcgagtcgct gttgcatagc ttcggcttgt tggccacgag attgtttaag acgatcaaat    43920
aaattaccca ttttaatatt cctctataat ccgccccttc gggctattct gtaaatgtat    43980
ttgtcaatta ttccgacggt gtaattatac tgcgttttgc tattgagtta acccgcaatc    44040
atttgttttg ctgggtctat ttcaataatg tcgtacacat ccgagaaggt tttgtgtcct    44100
tccaagaatg tatggtattc gatgacatag gatttacctt ccggcgtcgt gtaacgtaca    44160
cgatccatat catcagcatg ttcattgagg ctaccgtgac gccagcggat agaacctggc    44220
agatactctt gcgccttcaa catttttatag atttgctctt tgctcatgtt acaaccttaa    44280
atgagttttt tagatttcaa ttcacccttc aacaaccgag catcagaaca ttcagctgtt    44340
agccttgaca aaagaggagg cgtgatcaat tttttgacct ttgcttcttc gatgtcatac    44400
tcttcacaaa cactggccat cgtttcaagg attgattcct tgcgttggct tgctctcatc    44460
aacaccaatt cggaaaaaga atctggtgtg agcacttgtg ctatttgttg atcagacatc    44520
gattgtattc cccttccctg attgcttctt aatatgacgc aaaacgtctt tgaagccatc    44580
aggcgcggac tgaggaccac gaacaccaga tacgatcttt ggtgctccaa taatcatttt    44640
tatttcaccg ccacattcag aacatggctc taattcaggt gtatgacgtt cagcacaaga    44700
ttttcgagca ctaaacgaat ttccacaacc tgtacaggca taatcataaa acggcatgaa    44760
```

```
tcgcctccaa tacgtgtcgt agaaatataa taactgctcc caccagcgta gaaaacagga   44820
caatcctgct tgctttatca cgcagcaaaa catattcggc caacatatca gattgatttg   44880
cagctcttac attgacgtca ctatgtggcg aaaccgcata gaaagatacc atggcactta   44940
atgaatgaag gaatgtcaag aatcccttaa tccaaacaaa cgccgtcatc aacagcaagg   45000
cgaaaagcag tatatctgcc agcagccagt aattaatcat ttcttacacc tctattgaaa   45060
tcaggataat tttctatgaa gtaaggacca gaaaccatat ttgcaaacga atccacgagg   45120
tcatcgattg gctttggatc cttcacatcc aacatgtcca ttataccgcg catcttaacg   45180
ttgaacagct tctcaaagtg atctatcatg accaatttgt cggcatttcc tttaccacaa   45240
aaatgtttct taacaaaaga cggggtaaca atctgaaatt ccatattgtt acggcgcatc   45300
gcttgtttca atagagatgt gttctcggcg gtttggcata tgttgttgga gttttttgaa   45360
ttccccatag catagccttc tagggtgatg aaatccggct tctccgtaag aagtacggct   45420
tcagcccatt tggaaatgtt ataaaaccgt tcttcggggg attcatattt gggttgacgt   45480
aaaataagaa tattgtgtcg cacttgacga cagtgcttct caacggtatg gtgtgcatag   45540
aaatgaagat gatcaaaatc cagaggatct ttgtcgtccc agaagcacat ggctggacag   45600
ccgtaagaat agtcgattcc gcaaaatttc ataaaaatac ccataacgaa gtttcattgt   45660
gttatgggta tttagaccgg attatctggt gacgattttg ctttccggta aaatcaggcg   45720
aggtttggag tccatttctt cttgcatctg acgtatctgt tgcagtaatg cagaagtgtc   45780
cacatgacgt tgatccccc gcgcctcatc accatatgac acatggccgt ggcgtccac   45840 ataatgcgcg gtgcaaacca tcaaaacata acccaactca ccaacggcaa ccgttaaatc   45900
aaccacttcg gaagccaaag attctccgtc aacactgaga ttgggtgaat aatggatttt   45960
accatcagcc ataaattcgc tattcagcat aatcatgcca gcgatcgttt gtacaacggg   46020
gttcccctga tcatcagcaa cgaaaccgtc gaatgcgcct tcaaaccctg gcgcaatttc   46080 tccctttca tttgtgatca cagcgcgaag gcgttgaagg atgacgtctt gtacctgctg   46140
aatatcagcg cgttctacgt ttggcattat tgttctccag ttcataatcc cgttctttaa   46200
catattcata aagacgagaa gtaattcggt cggcattgcc tgtggtattc ttcacaaccc   46260
aaccgctcgt aaggacatcc attttatatc cacaatcatt atcttgaaaa taactttaa   46320 ttgtttcaag gcgacgacgt ttatgaaaat acggtattaa ttcgccaatg atgacacaat   46380
cgggataatg cttatccaga gtgtttatgt ctcgttgaac ccaaactgga ataacatctt   46440
cctcgtcaat tgggctgtac gttggatcaa cgataatcac attgaatcca taattcaata   46500
aatctttaac tcccagccac ccgaatttca tatcggacac ggtcatggcg acattcttta   46560
tccccaattt atttgcaaaa tctgtgagta atacaaaaaa gtccgtgttt gcatccggat   46620
aattaattgc gagttgctcc cccactttac tgaaacagaa cgcgtgcatt ttcagtcctc   46680
gttataaata caattacaat ataccgtgga gatacattat gaatttacca tcattgccca   46740
aaactgagag aacacataaa agtgatttct ggccgactgt gatcaaatac cgcgccttta   46800
cagcagggca acagaccatg ttacttcagg ttgctgatcc gaacactcct atgagtgagc   46860
gcgtggcaac attggagcaa ctatttgaca gttgtgttga tgctggcgtt ccctttagta   46920
aactgccaat cggtgttact gaagaagtat ttttaaagat gcgctgtata tctatcggcg   46980
aggtcatgaa gatacgttac aaatgtaata acaaagttca agccgaaacc aatgaaggtg   47040
gtgaagaacc agtttctggc cttaaagatt gtggtcaaga gcttgtgtta ccgatcccgc   47100
```

-continued

```
tcaatcaagt aaaatgcgtg tccccagaag gcttcaggga gacgtttgat ctaccaggtg   47160
gttatcatat aaagatgcgc cagccgtcct tctcggatgc ctcagtgctt aatgaagcat   47220
cctctgttga acaaatgatt gccacctttta tcgattgtct gtatgacgac gatggtcagg   47280
tttggaaggt ggaaaatccg gctgaacctg gtatcgatcc agaagttgct aaagaacgcc   47340
aacgcattaa ggatgaattt gtcaaatggg tcggggacaa tattgaatct gagattgttc   47400
aggacatttc gaatgatttc tttaaaaaga ttccgcgtat tcgttacgcg acaaaaatta   47460
aatgcccttc gtgtgggaaa gaacacgaag tcaaatttaa cagtgtcacc gagattttca   47520
tttaatttt gaaattgatt tactctccta ttttgtgatg tgtgacgaat taaaggcaca   47580
cggctatagc atatttgaaa tcagtgaatc gatgccgtgg catcttgatt tgcttaccga   47640
gacactgaaa attagattgt ctaagaaatc ttccaacccc acgtaatgtg ggttttctt   47700
tgcttacctg ttttataggt taagacagga acgtttaacc ttaaattgct ataacaccgt   47760
tgttgctgaa gtaagtgttg tgtaattggg gtttgaattt gttttgaagc aaaaataatc   47820
cttttctacg catgttctga ggtgtacagt attttcctcg cctttatgcc tccatggcat   47880
tggaatggga ctgcctgtca aggcggtgtt acgagcttca gcgagtagga acgaaaagaa   47940
taaaggttga acggaagcag agcttcctat aatatattat tcgacagatt tcaaatcccc   48000
gccataaata tcacatgatt ctaattgact aatgggtttc aatatgttag acaacttgcg   48060
ttggttttac gggcgcgttg aagacgtgaa tgatcccgat caaaacgggc gcgtcgcagt   48120
acgcatctat ggggtacaca cggaggatac cactctcctg cctaccgaat tattgccttg   48180
gggtaaaatg cttatgccag catctaacgc ctccttggca ggtttaggct ggtctccgac   48240
gggtatcact gtcggctctg acgtcatggg gtttgctttg gatgaagcat atcagaacat   48300
ccgtattgca tgggtatggc cagcagcaac accaacagat gggtcagata caaacccatt   48360
ggcgctgggt caggtcgttc aatctataga aaggcagaag tataatgccg tcgagaatgt   48420
tcctgttaag attgaggatg aaccgcaacc ggatccacaa ccaccagtag acggatatga   48480
tcctgagaag tggatgaccg tggctcgtgg ggaattgggt gtcaaagaat attctggtaa   48540
gttcaataac aacccaagga tattggaata tcataagaca acttccctgg ggcttcaga   48600
agatgaagtt agttggtgtg cgtcgttgt tggatgggtt ctgatacagg ccggatatac   48660
atcaacacgt tctgctttgg ctcgttcata tttacaatgg gggtctcctc tgtcagaacc   48720
acgttacggc gctgttgtag tgttccggcg cgggaacaac ccgacattcg gtcacgttgc   48780
attcgttcag aaatttgacg ccaactacgt ttggtgtatc gggggaaacc aatccgattc   48840
tgtgaaggtg agccgtttta gccgctcatc cgtgttgggt tatcgttggc caggtccagc   48900
aactacagct tcagcagctc cggcacaaca aaacggtaaa tggtctgaac ctattccaga   48960
tcgtaccccg aaagtccaag aaacaccgcc tccttctggt cgtgttcagg atattgacaa   49020
cacaggagag gtatcggttc cttcggctgg agggtctcgt tatccataca acaatgttat   49080
ggcttctcga gctgggcata ttatggaggt cgatgacact ccaggcgggg aacgtttgca   49140
ttggatgcac tcttctgggt cttacaagca aatgcttcct gacggtgatg ttgttaataa   49200
atcagtcaaa gatcattatg acctgacgat gttcgacaaa cgttattatg tggggggtga   49260
tcataacctg acaattggtg ggactgaagt acagcgcaag aaaggagaag tttaccactt   49320
acactcttct aactattcca atgtggtcgc tggaacagcg ttgatgaaat tttcccaatt   49380
ggctgagata caggcacaga acgtgttgcg tctcatctgt gaaatgttgg aagtttccaa   49440
tactttgaaa gtgcctaaaa tactggctag tgaaatagtt tgtgataagt tgtcggtggc   49500
```

```
gcagactatt gaaggcaaca tcaaatatgc tgaaggcgct ggtcgcgccg cctcacgtgc   49560
gggggcaact cctgtaacaa ctacaggccc aggtccaatt gatataaaac cggagttaga   49620
ggataacggc ggcaattttg gtggtaaagg cgcatgatta cactggtgag ggcagataat   49680
gccctctcgt gctggagagg caatatccaa aggggtttaa catgaaagag tacaaggaca   49740
ttgacctgaa gtttggcatg catccggtca ccaaagatgt cactaagaaa acaggcattt   49800
atgctgtact acaatctgtg cgtaatatag taatgtcgac ggtaggtgat tggccgacgt   49860
atccgagtat tggggcgggg ttgtatacca tgttgggaga aaacacaaat cccacgatac   49920
aggtcgacgt gaagaacaaa gttgaagatg ccattgctct ttttgagcca agagctgaat   49980
tgcaatctgt tgatgtatca ttgtcggacg attatcattc tctgggcgta accatcacgt   50040
tctatgtggt caacaaccca gagccgataa cagacaccat atggttaaaa cgtacaaact   50100
gattaaggtg cgttggtatt ggagcggttg gtaattattt caaaatgcgt cagtaaacgg   50160
tacagtaatt tcccacctat tctatggact atggtggttg gctttaggtt aaccaccat   50220 accatctagt ctccccgtca acacaaatgt aaacgaatg cgaaggatat cactgccttc   50280
agaacgcatt atttgacagt catggctgta ccctatttct ttcccttga ggacaagggg   50340 aacatgtgcg ctttcctta acagggtatc taaattttca aataaaggtt cttctttgtt   50400
attgacggaa tacaccgtct ctaatatcgg gaatttatac atatcatggc accaacgtaa   50460
tcacaatcat gttgagtacc gtatcaaccg cgacaccaga atcctcttca tgtatggttg   50520
aggcgcgcaa gtggatatct gaaatataat tgtctatatg catcgacgtc aaataaggac   50580
ggtgttgata cacaggacgg ttgacctgaa catattcacg cagaatgctg aatgaaaagt   50640
cttcacattg agtggtgtca atgcgcaaaa atctttgagc atgacaggtc tttaactcgg   50700
tcactttccc caaataatgg aggtctccgg atgaaccgat gcggaacatc acatctactt   50760
cagatttgaa aatttcgcgt tcaataagag tcgctggtgc ccaacaaact tcttccttgt   50820
cttcagcaaa caacgtgtct atcacttctg gtaattggat ataccaaag ttgtggcggg   50880 ggttggtgag taatttgttt gacatattat gctcctatta cgtgttgttt ggcttgttca   50940
taggctgtgc ggagttcaag ataagaatct gccaacaacg gtgatttgtc gttttccga    51000 ttcatgatta tttggtggtt aacgacagca cggcgtaatc tgagttctgc cacccagaat   51060 gcttttttgtt ttgcgtgtcc tggacgggcg cgtaggtcgt gataatgcat agaagcatga   51120
tatatttcag agttggtcat gatatagttc ctgctattca atttgtggcg tttgccaata   51180
aattactggg aagtataggc ggaaaggttt caaaagtaaa gccccctcatt gaggggcttt   51240 gaaagatcag cgtttcaaac ttgcggcgag tccagtaacg tcggtcacgg tttgatcagc   51300
caggacaatc acgggcatag acatgcgctg tttaccagtg atttctgta attcttccag   51360 cttgtaatct ttatcaagtt tcagaatctt atgttcaata ccgcgaatgc gacagatgtt   51420
ttcagcttgt aaacattgcg cacaaccttg tttggaataa atcgtaatca tttctcacct   51480
ttaggcaaat ttcagaccgt cggagactga tccagtaagg acaccagtca gataatcagg   51540
ggcttccgct tcctgtaatg catattgcat tgttttatta tctagccact catttatcca   51600
tggcaccgga ttgtctttac gggcttgtcc tggatatggg tggccaatag ctcccatacg   51660
gtgtgttgcc aaccagtcca ccatttgatg aaggatattt gcattcagtc ccagcattga   51720
gccgtctttg aacagataat tcgcccattc ttttttcttgg ttgacaacgt cgacatacat   51780
ctgggtcatt tcgccgcgca gttcttctct aataatggca aaatcaggt ccatcagtgg    51840
```

```
cagacggttc aggaaagtct gggtcaggat gaggtgatct tgctcatcac gagcaatctg   51900
acggatgatt ttagcgttgc cttccatttt gttgaggaat tgcatgaatg cccaagaaca   51960
cgcaaatgaa acatagaaac ggacgccttc gagggagttg gcggcaaaca gagcacgcca   52020
gaatgcacgc ttggcgttca tgatgtcttc acgggtgaac gcgcgtccag ccatacgcat   52080
cccgctgtaa cgcaccatgt cgtcgtagta tacgctgatc tgtccggcgc aatcgacgat   52140
ctcctgaacg tccagaacat ggtcaaaaac gataccagga tcattcactg tgttacgaag   52200
gatatgcgtg taagatagtg agtggatggc ttcttggcgc gtccactcca gaatagcaaa   52260
ttgcgcttct ggtgttgatg cccatgggcc aaacgcttcg aacggagcag caccctggat   52320
agaatccagc atggtctgtc gtttcaggtt gctgaagtag atgtgttgtt ccgcagcgga   52380
tagagtggca aagtctgctt tgtctttggt gacatccact tcttccggac gccagaattg   52440
gctgaggcct ttttcatacc attttgaac aaaaggccaa gccactttgt cataacgctg   52500
gatacttaca gggtcgccaa agaatggcag tcctgtatta tttgaagatg gatcgaatac   52560
tgagaattgc ttttgttcgt tcatgttcct ttcctgatga ataaggggtg acgaatcacc   52620
cctgatatta aacgtttgtg ttgtatagac ctaatcaaac aacacaggta tcacaaattt   52680
cttcaacttg tttcaactct tcatcttcct tggagtcttt gttggtgttg taatacagag   52740
ttttaccacc ccacatgtag aaagacagaa tatcctgcat cataagagag cgcgggatct   52800
tgccttctgg atatttctct gggtcatacc atgtgttggt gctgatagat tgatctaccc   52860
aacgttgtat gaccgcagcc gtcttcaggt attcaataca atccagattc catttcaggt   52920
catatagagg accaagggtt tctacatccg gaacgatctg tttatagacg ccgtccttgc   52980
tgcctttgat gctgatgaga ccttttggtg gctctatacc gttcgttgcg ttcagcacct   53040
gagaggagct ttcagttggt gctacggcta acaacgtggc gttacggatc ccatactcgg   53100
ataggttctg cttaagacct tcccagtcaa gaccataggc ttgcccaaca ggcttttttgc   53160 cattgggtag gatgtccagc gggagaggct gaaggtcggc tgttacaaat ccggaatcat   53220
ggatagttga tttcttacaa gatccgaaac gcatggccag acggttggac gctttgacca   53280
agtagaaatg aagatgcgcc atccacttgt ctagaagttc taatccgata ggcgatccat   53340
aacccgtgaa attcttggcc aggaaatgtg cgacgttgac gataccgata cccagaggac   53400
gatattcttc tacggccaaa cgggcttggc gagctgggta gtcctgatat tccaacaaca   53460
tatccaaagc tgaaaccaga acgaaagcaa catcttccat ttctgttgga tcttcaaacg   53520
ccgtcaggtt aaatgatgcg agtgtacaca gggcaatgcg accatcttca tcatcatact   53580
gttggaactc acgagtcgga agcgcgattt ctaaacacag attagagcta taaatcgtgt   53640
ccaaattgaa cggactatac tcgttcatgt gatcaacgaa tgcgatgtag atccgtccag   53700
tgtcagaacg ctggtctagt agcatttgga acacttcttc agcttgcagc tttttggaac   53760
gacataaccc ggcgtcggcg gccttgatca tattgtcgta catttcgcgg aatttattga   53820
cgtctgcgaa aaatgcttca tacatttcgc ggttgtcttt tggatcaaac aggtatagag   53880
gctgtttgtt caccaggcgc tcgaacatga cgcggttaat ctgaatccca tagtcgatac   53940
ggcgttcacg gttctcttcc aatccacggt tgttttgag aacaacgaca tcatcaaatt   54000
gataatgcca gatgggaaca tagcatgttg ccgatccacc acggataccg ccttgagagc   54060
aagacttcag ggcaccagtc aaatacttga tgaatggaac cagacctgta tggaccattt   54120
cccctttacg gatagggcta ccgatgccac gaattgcccc aacatcgaat ccgatgccag   54180
cacgtttgga aacataatcc acgatgcttt tcgcagtggc attaattgag tccaatgtgt   54240
```

```
caccagtttt gatcaataca caagagctga actgtcgggt cggggtgcgg acgccggaca    54300
taataggtgt tggaagactg aatttgcctg tactggcgta ttcatagaac ttcttcacca    54360
ttgtcagtct gctttcttta tcccacgctg agaataatgc catagcgatt gccatgtaca    54420
tgacttgagg ggtttcataa tacactttgc tgtcagaaga acgatcacgc aaaagatatt    54480
tttgagtcag ctggcccatt gctgcccaag tgaaattctt gtcgcgtttg tggttgatga    54540
ctgtgttaag ttcttcgaat tcttctttag agtaaagttc gaggaattcg cggtcataaa    54600
cacccagctt ggtgttcttt gcaaagatat ccagcaaatg aggtggcttg tactgaccat    54660
agacaacctt cgcagggtca tacgacttca ggcgggcagc aacatattga tagttgggtt    54720
tatcaacaga aattaaggtg gccgcagctt ggataatgat atcctgaatg cgttcggttt    54780
tcatgttatc ggtgaattgg atcttcgatg cagcttccac ctcagacacc gatactcctt    54840
caaggccgtc acatgctcgt tcaataacgg tatggagttt ttcaatgtca aaggggacag    54900
aagatccgtc ccgctttatg atgttaatca tagcgatcct cggtttgtgt ttatgcaggc    54960
tgttattata cgccgcctcc atggattgaa ggcggcgggg aagttcgtgt ggtatttaaa    55020
tgttgtacag gtcgttaatt tctaacatca ggcgggtgaa gttgccgcga ccattacgat    55080
cagacttatc gaattcgatg atgctgaatg gttgaaccca ctctggatat tcatccccga    55140
tttctacacc gtcaatttgc aaggaacctg tttccagctt gttgttgaag tctttaaagg    55200
aatccacata cgtctgtaac gcactatcac gcagtcgctt gttagactgt tgatatctc    55260 cattcacgaa gatgtacgaa gaatctgaag cacgggtcag taagttcttc agctgctcca    55320
tatcgcattc ctgcgcctct tcgataatca ggaaacaatc atcgaaagtc atccctttta    55380
cagtttcaag gtcttgaatt tctatgatgc gtttctccca cagatagttg aagaaaccgt    55440
cggaacccgt atctgttttg agaacctgtt tgaatgtctg tatgagcggc atcaaataag    55500
gcatcagctt ttcatatgtg tcaccaggcc ggaaccctgc tgtggcgcca gttggaaggg    55560
gagaacgcgt gatgataatc ttgttgatgg ttttgtcaat cagatgtttt gctgcagcag    55620
atgcaccaca ataggatttg cctgtacctg ccggaccgat agcgatagtg agatgttcat    55680
tgagtgcgga ttgatatgcg aggttctgat tttctgagag gccattgaac ggagcaattt    55740
tgaaatcacc tttagaaaat ttcatccagt cttcttcctt ctggatggtg tctttcttac    55800
gagcagattt tgtcttcgct ggcttcatgg atacaacttt agacgcagat tgcatgttga    55860
accttcctat atctacaggg gttgtcgaca ccttttaatta agcgacacgc ccagcatacc    55920
tgtatatcag ataaagaaaa aggccgtttc cggccttgag aattagcaga aactcttgta    55980
tgctgccgcc agtttagtat catactggtt tttcgcatat gccggaccat tgtaccgacg    56040
agcaaactcg gcccaattct tgttcttcag ggctttccac atattggcat cagccttgat    56100
gaacttgaca aatgccagaa ggtgagcgcg ttcaccagtc aggaaatcag tgaacatctc    56160
tttggcattt ggatatccac agatttggca gttgaacccc atgatctgga ataggccgta    56220
ggaagcactc tcgtaagcgc agtcctcgtc aagggtgatt gcaccctgaa ggcgttccaa    56280
ctccgcgtct ccgccgatat acccgccaga attggggtta accaatgttg ggtagagttg    56340
gtacagagca ttggctcttg cttgcccgaa tttggccgtc accttttttgt acatgatgtg    56400 gcgctcaaac agagttttga tcttgccagt tttggtaaaa cccgtgccac gggattctac    56460
ctggttcacc gctttcatac tggccagctc aacaccaagt tcacgtgctg cgtcaaccaa    56520
gtccgcttcg gtcagatgtt cctgatgagc gtctccagcg ttgcggatag catagaaggt    56580
```

```
ctttggtcca gcaataccat caataaccaa tccagcacct gcctgaacgg atttgacagc    56640
attctctgtt gccttaccaa atatgccatc ggctgtaagg gagaaaccga ttttgttgag    56700
gctttgttga agcgctttga cttcagaacc tcggttgcca agttttagaa tggccataag    56760 aaaataccte cgcaatgtat gcgaaggtat ttaaagtgaa agtcgaactt gaggatttag    56820
tgtcgattat ctgactacga cgacaggcat gatttctttg aaggaagtcc taacttcgga    56880
atcataccca tattttcaa atattttcaa catcgcttgt tccagttcct cttggaactg    56940
aggaaagtgc gcgttgggaa ttcggtcggc aacccataga gcgccaggag aggcttggat    57000
aattgctcta ctcatgtctc attctcctac caaaactttg aaaggggag gtttccccc     57060 ttgcggttaa gccaatttgt tcaccagagt ttctactgcg tcggcgctca gtttacccat    57120
tttgacatac tgggatttcg cttcaccgcc agcggctttc acgatatcac tgttgtcata    57180 acccttttc gggaatacca tcacggagaa ggttccgttg ttcagcgggt tcagctgaat    57240 gcggccttg ccgactacga tgtgccgta agtttcggtg ttcgcttcga caacgtggat      57300
gtcatggccc aggtctttca gcatgccaac cttgtcagca gttttggcaa ccacggcttt    57360
gtctacgaca acctgctcta ccagggtgaa gccgttggtc gctttcactt tgccgttcag    57420
cagattcatg aaggaagttt tgccaccagt gaagccagct gcctgagcga tgcggaacat    57480
ttcaactttt gcaacttcgg tgttcagttc aaaagagatg gtgccgttgg tgatcagagt    57540
tttggtagta gccatgatgt aattcctcat aatgtagttg ggtcgtttca cttttcattc    57600
ggcggggtgt tgtgtaccgc cctatgtgaa ctataatagt gcatgattat tgaagagtaa    57660
agtctttttc aataaatttt taaattattt ttgaagtatt ttaaaaggcc tcgtagaatg    57720
aggcctgaag ggaaataatt tgagttaaaa agttttaggt cggcttcttt ttcaaatact    57780
ggcgagccaa atccatttgt tcttcagtga taggacaacc gccgaagtcc accattccat    57840
tcctccaacc atggatgaaa ctcttagatt ctaagccaga taggacatat ccttcacggg    57900
cttgcatata cccgcgaaga atctcttcat cgtccatact attcagttct ttcaaatcca    57960
tcatatcttc ctcaagtcag aaaatcgtaa ggacgccgac agtccctgat atacgttctt    58020
ggctatgatc tgaagcagat cacgtatcgg gatatttccc ttgtcggggc gaaccatatc    58080
attgatatcc ttccacggta tttccggtgg aaacagaacg actttgactc cgctgtctat    58140
catcttctgt ataccgtcac aaacttgttt gttcctgtat tggttatcgg ggatatagat    58200
gtctccctta gcacttaata agtcggcatc ggcagtcgca agacaattag gtagaaacaa    58260
gctatcaatt ggaccttcta ctaccaactt tgttttgttc caaatgatgc gctcttcccc    58320 gtagattta gtgtcttcgt tcttaggctt gacagtggca taccgtaata ccccatcagg    58380
aaggttatcg ccgaatgcgc gccctgaac tatcttcatg cgcccgtctt gggtccagaa     58440
tgggattacc agccgctcat cttcgggtat cttcttttgc ttctcaacat ccgtttcaaa    58500
actcagaaga tcttgacgaa aatttctgct gtaatacaac aaagataacg tgctctccgg    58560
cattcccctg ccttcaacat aacgacgggc gatatgatca cggtcaagaa gatcaaggcg    58620
tatcatattc ccaaggtgct cttcatcccg tttggcgacc tgagaaccga tacgtgctgt    58680
ctgggtcagg cgctgtaatg gtttgagttt ttgtaacggg cgggaactgg tatccccat    58740 gatcctgaat ttttcaaggt tgtattcatt atacagacgc tcgtcaaact tcttcaacca    58800
gaattcaaac gcccaaccgc tcatttcatt acagttgtgg cacttgaaac gaaacacatc    58860
gtcatcacga tcataaaaga agtgaccacg acgcttgttg gcactcttct tagaatcccc    58920
gcataatggg caacgaaatt tggcgacagc gccaacacgt tcccagctga atttatcaag    58980
```

```
tcgggggcg agaaaattga tgtattgttc gtccaagaat ttcattagat atttggcctc   59040
tggaacactt ctgtcacatt ataatccacc ccgcgacttt gagctatgca aagctgtcgc   59100
caagccccat acaaaatatt ttgttccgca acctgattgc gttcaaagtg ggcgaattct   59160
tccagcatct gtttgtaccc taatagataa tgagggatat ctgtaggtct tcttttgtcc   59220
aaagatttag acaaatatga tgcataatgt tccggtgaag acaaagagga atattgcata   59280
ttcggaacgt gaacgggctt caaagatttt ctaggggtga agtacaacaa accccacttg   59340
ggagggaggt cttcaattt aataacatct gctgggcaaa catagaaacg atatgctccc   59400
atgcctatgg aaggattcat gcgatgaggt ttctttttgt ctgtcaggaa gtcggcgcgg   59460
gagactttaa cttccattaa tatagaacaa ccccaggtc tgaacccgat ggcgtcaggg   59520
gattcacgat tatcgaatga atttggttct acgaacacag caccacaatt catttgtttg   59580
tgtagaaatt ttgcagcgat ttgacaacct tctgagtgag aaggtataaa gattttgccc   59640
attgttatct gtatcctatt gatgacgaat gggcaaaatt ataacctgac gatgatccta   59700
ttgagttagg acaattgctt cagtttgtaa atcgtttgat agcacagagt cttgatttcg   59760
tcaagcgtgt tttgtaaatg gctatccacac tgattataga tcccattgac gtcgatgacc   59820
acgctgttga tatacgatat cggttcagga ttgtataatt tgatgttctc gaatcctgga   59880
atgtatatac cacccgcacc aatatacgct tccgtaaagg tgtccagcaa gtcctccagt   59940
tccccgtaga actccccgag tgccttgtgc ttggcatagg acgttgtaac gaagtggagg   60000
gcatgagagt gggctatagc aagcagtcca cggttgatga atatactcgc attgaccatg   60060
atatttaccc ctaaaaagaa atccccctg tatttagggg gattgtattt tataatcact   60120
ttttaccaaa aaacgatttt aataaattat caggaatttt tggaagacct aatttttgccg   60180 ccagttcttc tggggaatta cccaaaattt ttctgccgtt gatgagacca ccaacaaatt   60240
tggttcgatc tgttggactg cgaaggatag tggaggcacc gccaacttttt gcgtcataca   60300 tcagaatatg agcgccacgg tcaccgacga aacgccagcc ttccgcttca gtaacctgac   60360
ctttgtcagc tgacttgccg aagaaaaatt caaaaccatc atggacggca acgacttctt   60420
ggccttgggt aatgccgtgg gtctggtctg gagttagctt cactttgatg gtgttgccat   60480
tagtcaattc cagattatag atgtcggcct gattatctgg agtgatctgg gttacggtgg   60540
caccagtaca ccattgagtt ccgtcggcct gtttggtgat ggttacactt ttgccttgta   60600
tgccgccatg agtttgcggt tgttgagctt gttctttaaa atattcgata acggttttca   60660
tcgtggatct cctaaggatt ttgatgtatt tagcccccga agggctatg acttatttca   60720 gactaatctg aagattacca cccagcgatt gttcatattc actgtatgca ctatcaccat   60780
tactcacagc ccattcgtcg gattggcgag cgcgttcaag agtcatgaga tttggcacgg   60840
taggattata gcctttagat ttcgcgtcgt tgtataccgt ttgcaggtat tggttggcac   60900
ggttgatctg atccttgaat tcacgatatg ctccttcggt cgtattgcga cggaaagtga   60960
tatcccagtc cacgttcagt gtttgaccat cacggcttgc atagatctgc caatccaggt   61020
cgcgcccttt cggagcattg tcgcggatag aaccagcata tgttgcgagg tcgacacccg   61080
tcttcttggt agtccctggt tctttttcca gacgttcggt ttctttgctg atggtgttca   61140
gcatgatctc tgtcgtacgg cgatcaccca tgttgtggcc gcgccagagc accgcgccgc   61200
tgtcgtccac gtagatatca ttgaggaaga cttgttgcgg gttgtaattc gtgctgacga   61260
gggtctgcat gttcctcgtc accatactca tctcgtcaga ggtatcatca agaacaccttt   61320
```

```
gaacaaattc tttcttcaaa ggaagttcat atgttttcgg attgttcagg gtgcgacctt    61380
tgttagagac catcggagtg aatgctactt tacctttgtc gtagtaatag gtcacattag    61440
ttgtcaacac cgcgccgtca tacttcccgc ctttcgggaa attgacgcca gtccatgtga    61500
cagacatacc gttaacagtc tcaccaaata ccatggcgtt gctcggcatt ttcagggttc    61560
cagagttgac cagatccgca ccctgagcat tcagatcaat ggaaccgtag atggctccgc    61620
tgcgatcttt tagcatcaga gtcttgtcgc ccttctctgg aatgatttcc agcaggtgct    61680
tgccgcgcag aggctctttg ttgagttcca acagagcggt gttccctggt ttcacgcgat    61740
tcagaaccgc atcggctatt ttcagagtcc agtttgcggt ctctacatag ccccatccct    61800
gagaatgacg gatggacttg ataggatatg gagcgctcat tggtactgcg ttgatttccc    61860
attcaccgcg atactgatgt tcagccacgt atgtgatggt ttccatgact tcgtttgcca    61920
cccgacgagc atcaccagag atgacaccag gttgagtttc gatctcagag aacacgctgt    61980
acttcagatt cttaccgtcg accgaatcga agctgacaat gatcactaga ccgcctttgg    62040
tttgataacg cgcctgtccg attttcttaa tgctttctcc tgggaggtag cttgcttttct    62100 gatcaatgtt ggtatcaatg atacccaaca cacgggcgac gaaaccgctg tcgatcagtt    62160
gttcgatgct ggttgcaccg attgtggtgt tggaatctac aggcgcagat ttctgttgag    62220 aaccttttcca gaattttgtg gacgccgtgg taaaatcatt caggatactg atagggactt    62280
gcggtaattt caactgacga gcaataaaat cagcactttg tccgcgcaca gatttctcat    62340
tcatgtaggc accaacatac acaccaggct cattgtagtg aggggcgata tttgccgtga    62400
ctaagcgacc tttctctcta ccactccata tcatcatagg ctgattcccg tctgaagtta    62460
atttccagcc gttggaatca tcaacagaag atgatacacc cacatcagga ttattttttct    62520 ggtcaggaac gtcaccgact ttgtctgggt cgtcccaagt cacgcctttc attttcggac    62580
catcgaatac ctgagcagga tccttacctt tacgcacaac ccatacgaat gcacgatcag    62640
ggataggggt atacgtcagg tccatgacat tgagcttctg cttcaggccg gactgacgga    62700
tgatcttcgg caggagggta acaccacgtt ccaatgcttt cttggagaag ttaattgcaa    62760
agccgtcaat ggttttcccc aaaggcgtcg ccatgaattg ctttgttgct tcgatcatgg    62820
atgcgatgac acgcattgag ttttgaaac daccgattgc gtctggatag gtcgaaccac    62880
gtttctggcc tatgaagacc tgacgaacgt tcttgcccag cccctgcggg gtataaaatt    62940
ggatgcggaa ttcttttttcg tcttcatcaa caaatgtgaa gaaaatgtcg ccagcgttct    63000
tcttgccgaa tgtcaattca tacggggatg agttaaacgc ttcgtctaat tgtttagact    63060
cttcaagaaa gttcaagaaa gatgggatgg ccattgtaat tctcctgatt ataaaatcgg    63120 tgcggttttcc cttaattagc gaaagaaag ggatgctaac accccttttat tcttaacgac    63180 ggaacgggcg agacgcgttt tggcgattgt tgtaattctt atcaaattgt gccaacgccg    63240
ccggactcca ttcgcgttcc cattctttgt caacttcggt ttggttggca ggttcaatca    63300
tttcagcagt aggaaaatcg cgtttcataa tttcacgcaa ttgttcagaa ggggcggttt    63360
gggcgtggac taattcttca ccgtcgtaaa ctttggccat caaccatttg ctgccgtaac    63420
ggatatatgc gtcgaggatg attttcataa tgtagttcct gcttttcaag ttggtgtcgt    63480
actgcttatg tttagaatta tacgtgggtt attgaagaag taaggggct tttgccccttt    63540 ttattgaata ttttaaggtg ttggattgac aacgggaata tggaacctga ttccagagac    63600
aatgtccttc agctgaggct tccagccgtc caccaggcgg gacaacgcgt tagaaccagg    63660
atagacaata atgatgtcgc ttccggttac attatgttga gggaattgtg acatgtattg    63720
```

```
ctccatcgtc accoctgggt ctatcaacac aggaccgaca tccgaagatg catatgttgc   63780
ccccaaaccg tcgacgcccc atgctagtat tccataatca ggaatattgg cttcagaagt   63840
tatggtgaat ccgaagatac gattcagcgc agaaaaatca tacacgccgt gagcactgtc   63900
atatgtcaga taacccttg acagcatatc agcgaatatc gcgtctgtgt caccagttgc    63960
cagagtcggt atggtaaaca taactcacc tgccggagga gtaggatacg tgccgatagc    64020
ataaaggcac catgcgtcga tacatttctt gataaacgct tcaggagcaa cataatcagc   64080
caggcgcatc gttccagaat attcagaact gatgatgcct tccttcgcgc cctgaatggc   64140
cagaaatacc attatgtgtt catatccggt ctgagatgga gtgatattca ttatctggtc   64200
ctcttgagtt tctcaatcgt gcgcttattc atggcgatca ctcctgggtc gacctttggg   64260
tttattgcca tgcctttgaa agacacacat cgttgaagat atttagcctt cttcacgacg   64320
tcggctgcat aagaattgga tttctggtta cgattgaacc cagcattgta agaggaaagg   64380
gatttgcgga tgttttggtt atgatattct agccagaaat tcatttcatc aagggcagca   64440
ttggcagcat attcttgatt gaccagtaat tgatcgcga cattggcgta acacttctgc    64500
gttttgcatc cctcccgttt cccgacggtt tggacgcgat tttgaaatgc ccccatatta   64560
gccgatttga ggttattccg catggataca acatcttctc cggcgcggct ttccctccat   64620
gatattgcgg cgagagtgaa accaaggtct tgttgttttc ccacgtgata ggctgtggcc   64680
atggttgaaa gttgttgatc agaaaactca taatcacatt gggtggtact ttgggaagcg   64740
tgcacactcc cgctgcaat ggtaaaggtc acggacaagg ccatggcctt caacgttgtc    64800
atcgtcatga tggcgttcct tatgtgtttg tcgacttgca gctcgctgga gcctcctgac   64860
agggttaaaa gataaagggc acgtgatatt tagtgcccctt caccttattc gtagatcaga   64920
tggtatgatt cctcgatgca ttccaaccaa ccgtagacaa attccatagg atcatcccaa    64980
gctgtattgg aagcaatagt gaaattcccg tccaagattt gcatgtcagt atatttgttg   65040
aaacctaaca cggcatcaac gactattaag ccaccttgct ctagataacg cttgggtc     65100 aacgtcacct gataatgttt gtttcgccga ttccataact cgacagcgat atcacaagca   65160
atctgaattt catctttctc ttctgacata tgtttgtctc aaatattcag taaagattt    65220 acccaactta cggaatagtt taatacgacc gatcactttg acataaacat ctccatgaca   65280
tgggcgcggc ttacaccagc atcccaaggt cttccatct aattcaagga gttcatcttc   65340
ggtgatatcc ccttcaatca ggcgcacata caagtcgtct tcaaacaact caatacagtt   65400
tccccgcccg tggtctttga cctcgaacgg gtttccccat ttgccaggac ggccaatgta   65460
gacgtcgtgt ggttccttct tgaagtggac gactttcata tgattgtatc agctaaccag   65520
tatgctgccc aaacgcttac accaccgtac ataaaaccat agataatttc tccagagttt   65580
atgtggcgta aacacatatt cacagaacaa attgtgatta aaatcaaaaa taccaaacaa   65640
atagtagcca tcatgacata tcctcataat tagatagatt gatcaagaag acaggttcc    65700 ggtcatatat gaggtcaatg gccttgcggc tacccacagc ctcacatgtc caataactgt   65760
aattccctgc gatcttcaat gctagtcgga cgacatgacg cctcatattg tactgagcca   65820
actgatatcg gacgcgtgtc ttcttgcgcc agcattgatt ctccgctttg tacttgtaga   65880
ggatcatcag gcgaacggct ttgtacaggc gcttttcagc gcccttggat ttctttgata   65940
cacgaatcag gctacccatg atcaatcctt cttaatcact tcggtcatgc cattacgcag   66000
accataacga atgttatgtt ggaaatattc ttggaactcc tgttcacgct gactgatgac   66060
```

```
aaacagattg ttcccaccaa atttatgttt cagcatctca accgattctt gtacgccacg    66120
ctcgctcatg ttctcaagga tttcatctaa cacaaacagg ttacattgca ccgacgcctt    66180
gaggttggcc acgtcccgta gggctaatgt cacagccaga ttgagtcggc tgcgttgtcc    66240
tgtagacagg gagaatatgc tttgcccttt acgaccagca gcgctcatgg tgatttcaaa    66300
tgtatcatca acagcaatat ccaagaacat attgagtgct tcaagatact cgtttatttt    66360
actattgagg aaaggcaaat acaggctgat aattcgagcc ttggtctgat catcttttag    66420
gaagaacaga agatggttca ggtcttgcaa tttctcatcc aactctacgc gccgcgcatt    66480
cagatcttcc attaatgccg tgatgcgagc gatctcttct tccagggcgt cagttggtgt    66540
cggcttaacc gccaatttac gctctaaatc agcaatggat gcctccagag gggcacggcg    66600
tgatttcagg ctggtgagtt tatcagccgt gtcgttgata ctcttagaga gctgctcacg    66660
ggcttgacgg attgacgtcg tgatatcttc gtaacgggtg tctacggcct tgaggacgtc    66720
gttaattttg gactgttgtt cccgctgtaa agatgttttc tcaacagcag cgacatcata    66780
gaatccttgg atgtcgcgtt ttaatgtagc gatcgctgat tccgcttctc gaatttcatt    66840
gcgcaaagaa tccagttctt tgtcaataac cgaaatctga aagataatt ctgaatctct    66900 gacattgtaa ttctcaatca gggaattcac ttcttctagg gctgtatcaa cctgaagaat    66960
cttgtcagtc agttcactga tttgtggata atattgactt tcaatgcgtg atttggtatc    67020
gtccgacact aattgcgtac acgtagggca agtgcccata tcgtgaaaac gtttgatggc    67080
agattcatgg ccttccattt ctgtgacgaa tttgaaacgg aagttctctc cctgttgacg    67140
ccgcgccaac gctttattca gttcgtcgag attagcattc ctctgaccga ctagttcgtt    67200
tttgcgttct gtgaccaccg ccattctttc gcggatttct tgtaacgacc tttcgccgtc    67260
ggatacttct atgcgttcat aatcttcagc cttggtatcg gcttcatcct gaactgcttg    67320
gattttggcc gcatactctt cattgatggc atcgatatcc cctttcattt cggcattcag    67380
gcgattacgg acttctgata attctgattc caatttagag tcttgagcac gggactctgt    67440
cagttgttcc tgcactgcgc tgatatctga attcaggcta ttcagacgtt ccttctcttg    67500
gacaaggata tcagcagatt gttgctggat catcgcattg gaattattga tctgttccaa    67560
ctgcgattgc tggcctttta aatttacatc atgaaaggcg taatcattgg tgaccgtcgt    67620
gagttcattc gttactgtct tgatagatgc ttttacatct tcattcatca gactgaagaa    67680
ccccaaatcc cagattgtct ctaccatagc gcgacggtcg gcagtgtaca tttccgtgaa    67740
tgggatgaac ttctctttgc ccagaaccag ggagttctca acatcttct ggtctacgcc    67800 aatcaggttc acaatatatt tgttcatgtc ggctttggcc gcatcattca cgacctgctt    67860
ccactcaccg tctaccatct gatagacttc tacgaaatca ggtttgatac cacgacggac    67920
tttccattca cttcctcgag tggagaactc aacttcaccc acgcattcct ttttgttttg    67980
ggaattgact aatccggctt tcttttcttt cttgctgtat gtgtcattat acagaacgaa    68040
gaataacaac caaacaagca ttgtagattt gcccgcccca ttgtcatcag atgtgactag    68100
ggttgcaggg ttgcgttggt aatcaatttc catgaattca ttaccgatgg aacggaagtt    68160
tttagcgcga ccgcgatgga aagtcagttt gtgggtaatt tccccacgga tttcaaatgg    68220
tgcttcaaca gaaacaggag tgtccgcttc tttcaacagc gaaccgaatt tagacagtag    68280
atctacattg ttcattatta tgcatccaat gtgttcaaac gttgttgggc agcattataa    68340
aattgttctg caagtttgca aacattttca gggcgctgga tattgttggc tgcgcggata    68400
tctttcttca agacttccac cgcatcagta gccaccatct cttcagtgac ttctaccttc    68460
```

```
tcggaagcaa cagtaatcgt ccgatcgatg aagttgtaat cgatgcattt acagcgcttc  68520
aatgcgtcac agaacttttc ataatgcttg gcattgtcac ggttctgtac aatcacctta  68580
acgatttgcc cttcaatacc caaaacattg tttaaccaat cggggtcgat ccaattacct  68640
tcagtatcag aagacatttg ggtgtagtcg tattccacga accggaacaa cgtttgttgt  68700
tcgttgttgg ggataaacaa ttccccgcca ttcatgtcgt ctacatagaa tcctcggttc  68760
gtcccgtctt tgtggtcttc ccaggtaagg tgataaggag tcccaatata ctgaatgtta  68820
ccttccatcg aacgggtatg gaaatgtccg gtatccacgc gctcgaattt cgaaaggagc  68880
gccaagtcga tctgaccttt atcacataca gaggactggt acattttgaa ccctgccaac  68940
tccagatgcg caaaacagta cttggcgtct gtatcttgta tcgctttaat ggacgcatca  69000
tagttctctt tgttaatcca cggcagtagg agggtcttga cccttcaat cattacttca   69060 gttggttcgc tgtaataatg ataaacatcc ggtgccaatt cattaagata agaaggccag  69120
ttaatacgat tggactcttc taacgtgata tcatggttgc cgacgatgcc attccattta  69180
atacctgctt tgcgcagcgc tggcgtcaat tcatctttca accaatcttt atcgcgacca  69240
tacatgaatt tgcgaacatc aaacgtatca ccaaattgcc acacttcttt aatatcggcg  69300
tcaaccaatt ctggaataaa ataattgatg agataattct ttatgaattc tcgaacgtaa  69360
cgggaaccat tacggctccc aatatgtaaa tcgccaattt tagcaatcgc cattattttg  69420
ttgctcccgt tctaatgctc gtttctttgc ttcttcccaa tctggttcca tagaacatat  69480
ttcgtcttcc agattgaatt gagtagagcc gaagtcatag tctgaattat cttcggcgtc  69540
ggcggtaatg gtattttcac tctttgtgag acattgaagt ataccgcgag gaattttctt  69600
attcttttcc tcttctttga tggcgatttg cttttggcgt tccttttcgc gctgggcttc  69660
tttcttagtt tcaaaatttc cgatacgctc acggaagtcc attgttatac cagtgctgtc  69720
tacgaatgtc tgttgctgga agtctgggtc atctgataat gcagcgaaac cacctgcttc  69780
ttcaaatgaa cgcaacttga tataattgtg ttcttcttca ctggtgagtt tcttggcgaa  69840
tgaacgatcg gcgcacatcg ttacccaaga gaagaaattg atttttcctt tcttgccgat  69900
atgactgacg tcaaatgtat ggaggtaacg aaggatgttg acaacggcct cactgaccat  69960
gtcttcgcgg tatggataat cacgatagtt gtagcgcata ctcatgttct taataatcat  70020
ctgaacattc atgccacat aattgggat tcttggtagg ggtgttcctt cggccaaagc    70080 cttttgcga gccggaatcc aatctctcaa tattccaaca acacggtcat tatcttcgtc   70140
tgtgaaatat ttggtgacgt tatcacccct gtctacaaaa ttcatacccca tcgtgataat  70200 cctcaaatac caatgaattc attgaaagaa ccaacgactt tcttgaccga gaacggtta   70260 ttttcaagaa ccattgaact atcttctttg gctctaacgc tccactgatc cgcaatttcg  70320
ttgcccatcg ttcctgcatg acctttcacc catttaatt caagttcaca aattgaacaa   70380
actttgtcat aataatcgaa caactcgagc agaagttctg tgttcttagg cggcattcct  70440
tcatattccc atttacgacg ccactccaaa acgctattga taacatattg gctgtcggat  70500
atgatgcggg ctgggggaat gcagcgttca ccgcaattag agaatttcca taggatcttc  70560
attgcgttta taaccccgag taactcagct atattgttcg ttgacggcgg gggtaaatac  70620
ccataaaaca ctttccattg ctctccagtg attggactga tggcaaatgc ccaaccagcg  70680
gctcgtgtct tctgagggga tgatgccccg tcagtgtata tttcaatcat gtataagtat  70740
cccaaactgg ttttatcgat gaggaacgaa tcatgtcaga acgcgcatat cgtttcagtc  70800
```

```
tgaccgcccc agaaattgag cgtttgctct tgtctataaa tgattccata caaaagctgg    70860
acatcattta tgactacacg gcgggtggga ctgaaggtca agtcgcagct gcgtcagctg    70920
tcaaaaacat gtggctaaaa cttaatgaga tggtcacagg tgaaggtctt aaagacgcaa    70980
tcaatgcagc taacgacagc aacgtattca ccgattatta aagtctatt ttagatcgcg     71040
aaacttggaa atttattggt tctccggcag atttattagc aagggacgat atagacactt    71100
ccaattttga aggcggtgaa gtaatcctcc tacaaaagaa cgcttcgggc aacccagaat    71160
tccaatactg gaaagaact cctgtggcag gaggtgatcc aatatttggt tgggaatctg     71220
tttatgaagg aaactccaac gactcttcta ttgatattcc ggttgttggg accagcatac    71280
tgaagacaat cccaaaagca ttgtttcata tggtcgaatt ccgagtacac gctcgagagt    71340
ctaccctcgg tcattggcag acactgatg gcaaaatcgg ttatcgtggt gaagatctga     71400
tttatagcct gtataatcat gttcaaacca aaccgatcgc aaatatatct ttcagccaag    71460
atgtggacaa tatgattatc acgataacga cacttgaacc aaatatcaag tgccatttat    71520
cgtttattgc gggttattaa acctcaaaca ctgcatcggt gaaccaggtt gggaagaatt    71580
ctgggttgcg catcataaga gattcaaaag atgaatcaat gatgtatgtc gcagcccagt    71640
catcaacacc cctgaccgaa cgcccacaca tttgaacaat gcgcagtact gcattgcgga    71700
aatatgccga cggatccact gaattgatat gtgctatcag tggatcgccc agataatcat    71760
aagggacttt gatcagtatt tggaaacggc tgtaatcccc tttgaaatca taccttctt     71820
ccatggcagg actggcaatg acgcatgggg actttgttct aaaagcattt tccataatat    71880
ccatcaacgc ctttcgggtg cgcggaacat ggataaaatt ctgatatttg ctgaatttt     71940
gtattgccaa cgcgcgatca taactcactg tatggataat accggactga cctgggtgga    72000
acgcgattat ttcatcaata tattccgtca acctttcat ttcatagtca cccatattgt     72060
tagtcatctt cactatgggc atatagttga cttttctgtt ttcaatcggg atagggttgc    72120
cgatctgaat ggaatgataa tcccctgtc gaatacccaa tgaacgagca tacgaatcta    72180
taccacagat cgttgctgac atatgaacgt gataatcagc ttttcggaat aacccgaatt    72240
cacttacatc agaaggcata acgggtttaa accgaataaa gtcatctccc ttttcctgta    72300
cgataaaggt gctggccttt gtctgagaca taataccaca ataatcactc aagttatgca    72360
agacatctat aatgtctgcg agtttcatca cttgactttc actcaggcgg tcatcttcaa    72420
ccaattcttc aagaacttcc aacaaagact ccactttaag atggaggtct tcaaacatcg    72480
aatgcatttc accagacaaa gaatacaact tgcccaagac atagtccttg gtgcgttcta    72540
cgatatcggc aatgatagag actatctcct tcccttcggg gatagttcgc agtccgtcca    72600
cagccttgt attgtattcc attatcgtgt gctctaggag cgtagagggc atcttatgac    72660
actcgtctaa gatcagcata tcggaacggt tttcaggctt catacagatg gtggtgcaca    72720
tctcaatcat catagctgca ttagtgcaac gcaatgacga aatatcagtc cataaattgc    72780
gcgcctgtac ataaggacaa cggcgtttgc tacaatgccc gtcgcggcat gctatacggc    72840
attgcacagc gttgtaatac acatctgggt gtacgtggca acgatagttc ttcttgcctt    72900
tcaggatgtc tatcgccacc gctttttcag cagcatactg atcttgtaga cctttggtag    72960
gcgtactgat agacgtgcgg aattgcccat aaggatcggc ctgtaaaacc aaatggcgaa    73020
tcactttatg aatggtagtg ccaatcaaag atttaccgac gcctgttggg gcttcaatga    73080
ttacgtgttt gacttttttg ttgaccaagg catcaacgc ttcgacgata cattccatct     73140
ggccttggtt cgccttgtca tatggaaatt cgttttggc aaggctttgt atttcttcca     73200
```

```
caggaacctt acggcctatg gcgtcaattg cctttcggta ttgattaaat gctgtcacgt   73260
tgttcctcct ttggattctg ttatagttta cccgaatccc aacaacgaaa aagccgaggc   73320
attaacctcg gctttctctt ttagcctaac acgctgtgct aggcacgacc gctctggatg   73380
tgattactgg ccgttggcag cagctttcag accttcgccg actttgaatt taacaacatt   73440
tttcgcttcg atctgaatcg cttgcccgtt cagcgggttg cggccagtgc gcgcttcctg   73500
atgtttaact tcaaacgcgc cgaagccgac gaattggaca gattggccag ctgcgactgc   73560 agttttacg ccgttgataa aggatgccac gatcttctct gcttcgcctt tggtcatacc    73620
ctgagtctgg gcgatgtgag cgataaaatc agtacggttc attcggatta ctccagttgg   73680
ttgtttacga tgtttcacta caagaggact acagcttacc taacaaatat tattgaataa   73740
agcgtttatt tgccgacgtt tagcatttta cttgagccag aaccatcaac aatcagagta   73800
catttcccgc tgttggcgca agattgcaac accatgttat attcgtgttg taaatattca   73860
ggtgtcagag atgtcgtcag tttctgattc gccttggctt cttggtcgcg aatttcaacg   73920
ttctttcttg ctgtatccaa acgtttaatg aatgttgtta ttacgaatat gaacagataa   73980
cggattaacc cgatcatttt acacctgcat tttccacaat cgcttgataa atgtgacgtt   74040
caatagttcc atcacaaaaa cctggccgaa ataaaccagc tatcgcatcc caacacttct   74100
gagtcggttg aaccggaatc ataatgtgtt ctttgtcttc gacaggtgtg ggtaaacaaa   74160
taacctgacc aaccgtgata tggcctgggt tttggatatt gttgaatctg gctaatttga   74220
tatactgttg ggcatcacca tataatttta gagcgatgct ggacagagta tccccaggct   74280
ttacaatata ttttgaaatc atatttccca ccctgtgcta cgcagatgat caaaataatc   74340
gttgagttcg tcaatatctt cgatatcaac ccaacgatca tccagtccca tatcatttag   74400
atcttcttca gtcagatcat gttggtatat ttgaacgccg gaagcattac aataatccgg   74460
cttgatgtta ttgttatact gaaacaggtc gtaatcggcc agagtattct tcagacgttg   74520
cgcttcttca aatgttggaa cctcaacatg aaaagcgatc ccaggaacct ggggaatatg   74580
ccaaacgcga aatttaagtt caaacggttt attcgacatg gggttctccc tgagacagta   74640
tggttttcat ctgttcacgc gtgataattg tttcaacaag gttctcgtca atcatcattt   74700
cgtttaacag ttcacaaccc agaacatgtg gtcgcgccat atacggcatg gcgttgagtt   74760
tttcttctat gtcaagaacg cgcttgacag tcagacccat agaagaaaag ggaacaggat   74820
aaaagaatga aataatctgg ttatccatcc cgtttgaaaa tcttaccaac aatacatcac   74880
accatacgcc ggacatatta cacctccaga cggttacaat gagaaagcgc gttatcaatc   74940
tgttcccgag acagatattc caacggggttg cgagaatacg cgtctaacag cagcagttgg   75000
agcacagcgc gattacgagt ttcactctcc accatgatac cgttcatatg tggtgaacgg   75060
gctgtccata caacatactg acctaaatcg tcgttggcag tcaggctaat gcgaaactga   75120
ttgcacaatt tgtcgattaa cgcataatca tgtgtgaacg tcccttcagt tttccagctt   75180
gatttcttca cctgaagagc ttcaccacga gttctgaatt ctaacgtcac tccatgagtt   75240
tcattgtcga aatgaacaac tctctgagtt tcattttttca gagtccggtt catattatat   75300
gcgaagaaac gggcgtcgat ctccctattg ctcatggaat taaaatcgat cggccaaaat   75360
cgtgcacgca taatcgcgcc ttctggcaat acaattagtc cattttcacg ggagacatag   75420
caaagaacgt ttaactgcag ggtcaggatg ttccacacaa taaacggaaa ttccagtggg   75480
aaggatagcg tgggcgacaa caccagatct ttcaaaatat aaattaccct ggtcagcccc   75540
```

```
gatgataata cggctcttgt tgttcataat atagatctct caaataaagg cggtttaata    75600
ataaccgccc taatgttatt gaattatttt atatcaccga catacatgtt caaactttca    75660
tcccattcta aacgaacacg aatagtgcca gaatcgtttg ggaaagacaa tttgtcgcac    75720
atatgacgat ttgcatatgt tccgctctta ttaacaggat aatctttacc ttcaccgatt    75780
gcgaatcgtt tgaagttccg actcaccatc atattgatgt tagtccactg caattgttcc    75840
cgtagggttt tgcacaatat aatcttccca ttagaccgga aagacacgaa taaatcattt    75900
ggtgaagaaa atcgtctttc ttgcggacat aactgcctga ttgaaataaa ttcagattct    75960
tctttattct caaccggaga cttcacgggt tcttcttttc gttttctgc atattgctca     76020 acagccttt ggctgacagg cggcagatca atagaagggg agatgactgc tggcttaatg    76080
actggtgaag tacgagcagc aacaagtttt tcctgagctt ccagaattct ctcttggcga    76140
gattttggtc gagtatcaac cttggagctg aaatcacaaa ccgtaaccca gtcaccctga    76200
tcgttgcgct tggcaaccag agttaatttg taaatgatgc cctgtagctt gctttcacgc    76260
atagtgtctg caaaccagaa agcgcaccct tgctcaaatt tttcagcgaa gaccacgcga    76320
ccatcatcat ggatcagaat aacctttgct tgttaggtg cgaacatttt attcttttca    76380
acgatcgcct cagcgatctt tttggtaatg atcatcacga aatacacctt tcagttcaat    76440
ggggaataaa attttaacct gaaactatct ttgatttcca acgaaattag ttgcaatttc    76500
acggcacata gtcagatctt taatagtctg tttgctgttg tctgcggcag attccatcat    76560
agataaatca agcgcattct ctatctggtc cacactatag agatcaaggc gtttcaattc    76620
accttcataa tcagataaaa gaattgatgt atccttatca tccggatgga attgttgata    76680
tgtagacaac caagcagcac aaatattcaa cttactggcc ggagctgcca atacttggga    76740
agacatgaaa gtgcacagga ataacaataa gattttgatt ttcatctttc gttctccttc    76800
atcatattat cacagtcaat tcttgtttgc ttgagttcac gggaaagcct tggatcatca    76860
agattgacag acaaattagt ggaaagatct ttcaaaccat tctgaacacg gtcttcataa    76920
taatgatcat tttccaccag ccatgctctc aggccaaggg cgcgagtccg ccattccttt    76980
ttcaaacgtc gatcagattc ttgatcagca ctgtattcaa atactcggat acattggttg    77040
ccatcattga tgagatccag ctgacgtcgg ccaacctgca caccttttg taatgctgga    77100 gaaggaagag aacggcactg tcttacggtc attcgtcctt gtgtgcccat acgaccagtc    77160
atgatgagat cgccagcctc catgcctcct cggttaaatt cttcgtcgtt catatatcct    77220
tttaggttga acgcgccttg cttatatcga ttaaattcaa taccagcgtt tacaacggca    77280
tctgtgacat tacctgtggc ccagagttca gcaaagttct ctatggaacc agttttgtct    77340
atagcaacag cttgggagaa cccagcacag taggaaagat cagaccacag tttttcacct    77400
gtggagttca gcttggcggt ggcaggaagt gccagaccag ccagcacaac cccgatgatt    77460
aaacgtttca tggtgattct ccttatttca ttggataaaa tgatagggct gtcaccatgt    77520
tgagtaaagg gtttcaataa actatcgtat tcagaaacgg gtatcgctga ccgttctgta    77580
tcgcacaccc tgaaactgtt tagcgagttt aacaaattcc atcgctggca aatcaacttt    77640
gtagaccttc atgcgctgtt tgccgtccat gttcaacgca gccacaaatc ggtgagaacc    77700
gtcaacaacg taattgtcag aagacaccca aactcgaccc atgggcttct tatttctgat    77760
ctgcttcata atcttccaga ccttcatttt attgatttcg ttctgggtaa gacgaagcat    77820
tttgataggc acttgcgcag catctataga cacgccgtta tcttcaagat atttgtgaaa    77880
atcttcttgt ttgtcggcat cgatttgcgg catagaagaa cgagaaagcc cgaggttccc    77940
```

```
aacaggaatc ctcaggccat ttatgatatt catccagtca ataaaggatg taaggaacat    78000
gacacacctc gggatatagg gttatccctt agttagttca ttcggactta aacagcaatt    78060
cgcgaacaga attcccaacg atattttggg cgttcaacaa acgagttaaa tcatccatgt    78120
catatgctga attggtgaca tggcccaaga taatcgccaa cattccctcc agcgctctcc    78180
gattgttatt ctcttcaatg tcaaacttaa tttcaacaaa tcgagatagc attctggatt    78240
gagcatgagt ttcgttggtt ttgctctgta taatatcttt gatttccgaa cgagcaatac    78300
ttctttgatc tgtcatgata tagcctcttc aaaattggaa tgattgtttc ataacgctca    78360
ccatgtatga tggatctact ggtgttctgt tatacgtgat cttgcccatg ccattcagac    78420
gttcgacaat gcgctcggca ttctcttcta ctgcggcctg ggtcggttgg taatcgttca    78480
aatagatcgc gagttcctgt cgattgtcgg acgtcacctg attgcggagc gaaggatagt    78540
tgacaacata cccacgagaa atcagttcgg caacaagctg atcgtagcgc tcgatcagat    78600
aaatgagttt gtcgcggaag aacagcacat gaccttcgtt gagtttgtac tgctttggag    78660
cgcccttgag attacggcgt tttccattca ccacgttaag gacaactggc gcaagttctt    78720
tgtactcggc aaggaggtgt tggtcgcaaa gagattcaac gggaataaca ttgatacggg    78780
tcatggtata gttcctgcat ttcaaatcgg cggggtaatc ataccccgcc ataatttata    78840
gaattaattg atatgcttca gaagagcgaa aagaatattc gccttggctt taaccttacc    78900
gacgacaccc gtttcggcat caacctcttc agcaacccat acttttcctt tcttgctaat    78960
gataacatct cggcgcgaag catagacttc cttagtcatg tacacacggc ggaatccttt    79020
agcgcggagc aagcccaat  tgcggtctat ttctactgcc gtttctactt tcttgtttga    79080
catgttataa tcaacctatt caatttctga ccaaccccac gttagccagt tattgaataa    79140
tacggcaaat gtttattcaa gtaaagccct tgaaagtaaa aatccccaat aattattggg    79200
gatttcatgg attattattt gcagagaaca acgacgagtt cagctaactc tccgagggta    79260
ggatcatctc catgtttacc cacccactcg tcactaattt ctacatcgta ctcttcttcg    79320
atttccatga ccagctcaat catgtcaaga tcgtcaccgc cgagatcatt cttaacccgt    79380
aacggcgcta aagcatcgat attatcatca atgttatcaa acttgtcctt gtgatccccg    79440
ttgcgccagg tttccatgtt caggttgtca caagcgtact gagccagaac acgcattact    79500
tcaacataag ttggttttgtt tgacataagc atatctcaaa atgaaggcgg gtttccccgc    79560
cagttgaatt tagattttga cttcttttc  agccagttcg gcagtgacgg tgtatttcac    79620
cccatcaact tccacatcca tagtggattc ttccaaatcc aggtcggtaa accaaccatg    79680
gcctgcaaca atcccataaa ctaccttgga cagcgttttg ttcagggcgc ggacttcgtt    79740
aatggccgct tttgctgcgt ctccgatcca gctttcaatc agcttttct  gagtctcttc    79800 cggtacgctg gtgatcatcg gcgatttaac aaatgcattg tattcagcca gggcattagc    79860
gatcagctga tcagcgacat tcagtttttt accgtccgtc tgtttttga  taacagacgc    79920 gatgctcggc agtgaagatg cgcctttgat tttcacattc aattcacgac tcatatagac    79980
atcggttgat tctacagaag aagtcttcgg tgaaaatcca tagtcgcgaa ttccgtttgc    80040
tgacaggaaa tcagctgctt ctttgccata ttttgaagcc agaccagtag cgttgccttt    80100
accaaccagt tcatcacggt agaatttcag aactttctgt tttgccttca atgcttcacg    80160
gcgcacattg tctgcaaaga attcagcagc actgatattc tttgtcatgg cgcggttaac    80220
cattgggaca cttttccagat ttacaatgaa gacttccggt ccaccaaaca catgaacacc    80280
```

```
catggcagtc aaatcctgtg ccaccttagc ccgaacaatc ggagaatctg cagtgatagg   80340
cattgttttc aggttgatga taccatcctt gacaatggtg taattgcgat aacgccaggt   80400
ccccagctct tcaggaagtt catatttctt ctgtacaaac tcaggcacaa caaccgttcc   80460
gtgttgaact gtctgcacac tgatgttagg acgttctgaa ttgtagacca aattgctgat   80520
cgggacaatc cctttatcat ctgctggatt gaattcgggg gtccaatctt cgtgctcggc   80580
cagtttgagc gccagggctt tacgctcttc tttagaagtc gcattcgcaa tctcttcggc   80640
caacttgtct tcggtgtcat caactttctg tacagtaccg cgcccaatgc tcttgtaaga   80700
gaatagcgga tgcttggtga cgatagagac atcggcttcg gccaggtagg tcaaaacatc   80760
aacaatggtc gttgcatctt cagccggaac catattataa tcgatgccat caactcctcg   80820
cagagattcg tctacgatag cctgagtcag atcgactttg atgttggaat agtcctgctt   80880
ggtgaaacag ttgctgtact gtttgatgaa gcggacgtca cccgtcttct tcagcgcggc   80940
ccagaccaga tcggcgtcca tggtatacac gccgtaaaat gccagcacgt atgccgcttg   81000
gatgtctgcc agattatcca gctggtcgat catgttgggg tttacaaccc acagctgaga   81060
aacgctttca gggatgctga cgtggccaat agggtgctct tcatcaggat gcacagctaa   81120
aacagtcgcc acgccatttt caacataaat ggcatgggta taaaccagag gaacatcgac   81180
tacaactttc ggtgaagaag ttttcagcac gttttccaat tcggtctgat attcattctg   81240
tccttcggcg aatacgtggg tcgcaccaga acgttctgcc attagcccca gcagttcgcg   81300
attacaatac caaccgtatt cgatgaaggt aatgttatca aacgctttgg gcagtacttc   81360
agcggcatcc aggatttcat tagaacgcca gcagttgtca tatccgtcgg tcatgaatgc   81420
caggttgtta acataaccag gtttattcag gctaatggca gtttccgcag ccagtttcag   81480
tggctcaaca aaaccagtac aaccagaagg cttcaggaaa cggtcaatta gattattgat   81540
ctcactgagg tcggttgcac tgttaatctg acgtccggca ataccgttc cgaaatcacc    81600
gcgagatgaa aagtaaagga tgctcacagt atcttccggt ttcaccaggg aaggcaggtt   81660
ctccttcaga tgcttacgga cttctggaag tgaacgatac atggaaccgg agatatccac   81720
aacgattaca tggttagacg gcgcgacggt cgcaaccgca ttcttaaatg ttaatgattc   81780
aatcatcgtt ttgaccttttt tgggctttgg agtgtttgga gttcgcgtcg gcgttctcca   81840
gcatagtttc aatgaaatcc cggttgtttt ccatttgggc gaccagaaca tcactgggac   81900
ggaatgaatt gtcaagacaa tcaagtccgg cgcgttttaa tttgttgtcg gtcatcaggc   81960
tctcgtgagt tatatttccc aactatttca acatgggact attatattac gacaggcggt   82020
attgatgcca attaatataa taaaaatgcc cgattgaata taaccgggca ttatattatt   82080
gacaggttga aatattattc agaacttatt taaaggagtc tacaatggat ttgaaaatat   82140
aatctttgga gcgttgttgt accgggagtt ctccatacgg aaccatgcaa gggtgttgct   82200
tggtctgagg gtctttgact gggccataca cccatccctc agcctccttc tccgccatcc   82260
agctctcatg cgattcgctg gcttacgat caccagtgag atggaagata acacctttgc    82320
aagcgctctc acgctgccag gccggagatt gttcccaagg cagttgagag tcgtcaccaa   82380
cagacttgca gtatgcgcgg ttggcttcat gacaaatctt ggcgatgcgc agaaccaatg   82440
gcgaataagt gagatcgagt ttggagttgg cgcgcaggaa atcactaaca gccttacgag   82500
atttggcgtt gtgagagtca acaacaagtt ccatgtcatc cggcccacaa acgaaagacg   82560
ccaagaagcg ctcgccattt tccgctctga acatcacgtc ctgaatcatc acattgaagc   82620
cgaggtgata ggccgggcag agggcgctac gttcaacagc gtattgatcg atccggatct   82680
```

```
ctgccgtttc cgtggctttg gccaacagat cttgttcaac aagcgcccgg tacgcctcca   82740
gctgccacag ctggtcgaag gtgttattgt aggaaatctc tttgcccagg gcttcatcga   82800
agttggccgg gtctatggat gtgctgggct tggtgccgtg aacgacgaag ccgttatcca   82860
tcttgaaatg acaagtgata gcccggtgac cgccgacttc gcggtcttcg taaatcacct   82920
cagcgatatg tgacttcagg acttcaggag tgagtttgat gccagtacga gttgtcatgt   82980
gttatcctat gatatttgtt tacagacctc cactacttta cggcacatga cgatatcgaa   83040
caagccgata tggcaatcgc gcttcttgat ccccagatta tgagccagcc agctgtaagc   83100
atcactcctg ctcctctgcc cacttttcca gatagggtca aacgacctat gagcttcctg   83160
cttagcagca cggagagcgg cattcgccat ccttcccaga ggttgtctac catccccatg   83220
ggtatggcaa cccacacgag cgtcgcatgg cgagcatccc cagaacttca gtttgtgtag   83280
atctgggcga tgagggtaga gtacatcacc actgacgtat ttggcaggaa gaccgcaata   83340
atcacaaata acttgtttca tattctttac ctaaaagaaa ccccgcacac ggcggggttg   83400
ctcaggccgg agccgacaga ttatttcagg agttttttcca gttcttcaac agagagacct   83460
tccagttcct gctgtttctt acgctggatc agttccatga tcgcctggtt attcgcttta   83520
cgttcggcgg cggttgcgct ttcgtcacgt tctttcagtt taacaccgat gatcgctttc   83580
acgatatcga aacgcagttg taactgagag tcgactgcgc ttttcacgcc gatgaaatct   83640
tcttcatcgc tggcggcttc cttcacctga cggctgaggt ctttcgccag ttcgtttagg   83700
gcattcaggt tcagatccca aacctgctca acagacagca gacctttgtt agagttgaaa   83760
cgcagtttta aacgggttgc ttgatcaaac atttcattgt tccttattac gaatttgtgg   83820
tcaaatcaat tagaaaatga cttttacagt acggttaaac gcgccggaca ctttgacgaa   83880
cacgtggttg cgttgcgtcg tcgagaatcc cagaccggac agttggtttt cattcggctg   83940
gactttcatt ttactaccca acatttcaaa aaccttacga tgtttatcca gttccggctt   84000
cagatattcg ttgtagaaac cacgagtacc ttcaggatta gcacagcctt caagaatgaa   84060
gaacacgtgc ttgttgcctg tctgctcgcc atcccaatgg tttggtgaat tcaggaccag   84120
ctgtactttc tggaaggtcg cagtcttgat accccaaact tctttagact tatcaacatt   84180
agccagttcg gacttaatgc caacaacttg tttgtcttta acagtcagga tgactgcagt   84240
gatacgcccc tgatctttca ggccaggatg gctgaaacga tgcgttgcgc ctttgtattc   84300
tacttcgact tcaaacccct tcgtcgatttt ttcacgttga ttgtagttgt ggatttcgaa   84360
acggtattca ccatcgcgca gcttgctttc atctgtaaag atgatatttt ccaccggagc   84420
gcggtttgga tcaataccat ccataccgtt catatcgata tccagatggg cacctgtcat   84480
agagcggcga tcacggaagt aaacgtgctc catgttgttg aacatatgca gatcgaggtc   84540
gtcgttgttg tgccacgcca aggaaacgcg cagatacccg tcaactttac caccagcagc   84600
ctttacacgt tctttaatgg aatcggtcac ttcaccgttg taagaccagg agaaaccgtt   84660
gttccacttg aacaggttag gcgcatctgg gttcgccgga gcaaccaggg acatcaggtt   84720
gctagtatga gaattctcta caagcacttc cattgaatgc gcttttggca gaacattgct   84780
caggaaatca tcaacgctga tctcttcaac tttttccagg gatttggtcg gagttttcac   84840
ttcggcggcc agctgtgcaa acggatccat cgctttctga gcggccagat ctgcgaacag   84900
aacgttgttg attgtcagat catcgtaaac cgcataacga cgcgcagtg agtcttccaa   84960 acccagagca ataacttctt tctgagcgtt ttcgatcatg gattttgaaa ccagcgctgt   85020
```

```
cggacgtttg tagttcgccg gagcaacttt ggattcaaac gatttaacag ccttttccag    85080
ttccacgcct tcgctgatat ctgtcagcag agtgccgata actgtgttgc ggatgccgtg    85140
tggaacatga ttgtttgaac ggtatccagt atgccacgcc cacagagaac gggctgattc    85200
ggggacttgt tcatatgcct ttttggtttc aacaaatccc ttcactgctg ctttgtgttc    85260
tgcgccgcga tacagagaat tctggtcaat cagttccaga acgatttcag ctgattccag    85320
agtaatttca cgcagaccgc gttcaaacaa ttcaatagcc tggcgaattt cacctttttt    85380
cgaagcgatt gcgtccggac gcagaacata gctaccaagt aattgggtat ggaaatgatt    85440
gtaagtacgg attttgccat cttcaccaga ttcgtgattg tgagacaggc cgactttggc    85500
agaatcgtta aaataaacat cgacgattgc gtgttgtttg acatacgcgg aaagagccgc    85560
agccaccacg tcatattcat tacccagatc aatgttgtcc cagatagaaa ttacgttcag    85620
gtcggagtcg atggtgacca caccgccgat gttacggatg aattgtttac agcaggtgca    85680
atcgtgttca gtacgttcgc ggtacagcgg gttagtacca gcaggaaaag atgccagata    85740
cagatcccaa agagcatctt tatcgatatt ggtcatgaac agaccagttg cggacatcgc    85800
cagcacgttg ttattaactg ccgttgcgaa gggtttgaat tctgccatgg tatagtcttc    85860
ctgtttcagt tcaaagtgag cgcccttatc ggggcgcgtc gttaaagtga ggtcaatata    85920
cgctgaaaag atttattgaa aagtttaaac gggaatcatg tttactcgaa tacttctgaa    85980
ccgtttcccg tcataactgg tgtaaccaac aaccgtaact gatcttgttc cctttgata     86040 acccttigga gtactcacaa cgcgcacagg gcgcttgctt tctttatcgt atttcgaaat    86100
caatttcaaa agatgtttat cgatctggct taaactatca ccatacacgg tatattgata    86160
ttgctcgcaa ttacccaaca aaatgataaa tttataaatt ttgtcgacca aagatcgaca    86220
ttttggatca tcataatgat gccgacagac ttgacattca tatttcccag tattcatgtt    86280
gaacaatttt gtcgcccgac ttgaacacgc tgggcatact ttccatgaac gatgatgttt    86340
tacgggtttc attttttcat cttctctaac agattaatag aacgaacggg agtcttctgt    86400
aatggctgat taacttcacc accattatac cccacctttc ctcgaggttt ctccccgcgc    86460
atcaccgcct caacgcagcg ggtatatttc tgaagttcac agaacatgtt ctccaactgc    86520
ataacattca tgcaacggtc ttccggttct tctgccgacc aaaattcatt acgtttatac    86580
ccgtactgag cgaacaattg atcttgatga tcacgaaccc agaatatgca ttcttcatgc    86640
gtcatgccgt ccttgtccaa aaataacaga tcgataccag cacggcaacc tggaccagcg    86700
atagtgaagt ggttttcact gaatggatat tcatcgatgt atgtaaaatc aacccaaatc    86760
tggtatgcca agaatggtcc aagcccctca atgtcgtcat acatcgcctg gtaaacagag    86820
tcgggacggc taaattccct gaggcgatca aagtaatgag ggtgtttgtt gacgaatgcc    86880
ttcaaagagc ggatgactcg catcggcatg tatggttccc agccttctat tttgtattca    86940
ccaggattat cttcggccag cttcttggca accttgtaat ccatttcatc tataacaccg    87000
ccaacccgat ggacttttac cttcatgccg ccaaagcgtt gctccttgtg gttgacaact    87060
agttcaggga aagccaggca ttgtttcaga ccgcctgtat taaacgcatt ggtgaaaact    87120
ttgccacctt tagattcgaa ttcctgaaga acatctcgac accattcaag atttatgttt    87180
ccgaattctt cgatcgtcca tggaccaccc aaagcctgta taggttccca catgttgtac    87240
atgcggaaca atacacagtt gaacattttg tcagatagcg tgagatcctg atcgaggatg    87300
atattattga tcaaatttcg agactgccta tcgtgctctc tccgcacgtt acaaaacttg    87360
acttggcgta ataccggatt atccgtccat ggcgctggaa ggcattgcac gtccttcttg    87420
```

```
acatgtatcg cataacgatc cctcatccat tcatatgcca gctggcggtg gaatgaactt   87480
aacataggat gggctgattt gattttggtt tcacggacac cgcaatatgg gatgtcatgt   87540
ggtttatctt tcatggtatc ctctctagaa tacaaaaaca gaggccatta tagcctctgt   87600
tgtttagtga ataacggatt atattaatcg aagcgagaga ggtgtgtcac agtgttttga   87660
acaggtgcgc acgcgtatac acgaacatta gcaccccaca ccccacacag cttaggcata   87720
ttggtatcgt taatgatata cgctggcaca taactttcaa tttggccgtt aacatctacg   87780
ggtcgagaag atttttcaac tgccatagaa agaattactt ccaacgtttt tggagatacc   87840
aacgccacgc cgttcatatc atcaacaaat acctgacctt cttcaattgc catgctggca   87900
acgatgtcat tgatctgacg ggaaggggta ttcgtcagca tatcagagaa atcaggctct   87960
ttgaacacag ccatgttttt caggaatttt cctttcggat attctttgcc attccacatc   88020
acagtctcat tcactttgat gcatgcctga gggaattcac cttcaacgcg taactggcca   88080
tctgggaaac cgcgtgaata ataatattcc agtgccggac cgacttcatc ttctgagcga   88140
ataaatttgc tcatgttaga ggcaaacaca cgttgtaaac attcatcacc attaaaacca   88200
gcgatatggg ccacgccgtc attaacagtt gtgatatcac cctgagcgtc catgatggct   88260
ttcaggattt tatccatatc aacatcatcg gtgtcttctt ttggagttgc caccagctca   88320
agtttgatgt catgatcgaa ataagccgct tccagtaatt cgcgggtctc ttccagaacc   88380
agtttggcct gattgcgaat tttaccgaag tcagggctg taatatctcc agccgcatta   88440
ccaaaagcca aattcaatct cacgttttta ttaaatgtag ttgtcataat atagcgactc   88500
cagttattcg cttttttgccc gacttgggcg aatagtgtat tttggaacca atttccactc   88560
agaaacttgg tcatgttttta caactttgat ccgagacatg tcagccactt cggttatttg   88620
ttccggatgc aagatcttaa ccatattcca ttgctccaga agccgtataa tccgattcat   88680
acgcaggaca tcttcacgcg taaagccgtt atagtgccca tctagcatga acaaatgctt   88740
gaaatgcacg atgtgatatc tgccaaattt atgcaggata tgacacgttt gatacaaggt   88800
gttaggctct tgacgagtgt taaccccctat ccgactcagc gtttccttga tacccaggaa   88860
aatccctggt ttgtcttggt tcaattgaac ttcaaccata cagtcaacaa tgctggcctc   88920
atcgttgaca gctgaaagtt ttaagatgtc cagcgtatta cgcgccatga ctcatacccc   88980
tttaacaatt atttgaatta cttagccttg cgcggtttgg cttttcgtt gctgttgaa   89040 cgttcgacct tcgccttgat ttcagccagg acttctttcg gcaggaatcg aacatattct   89100
gaagcctttt caggactgat gtaataatac tcagaaatca atttcacatc aggatccata   89160
gctcccttct tagaccactt gtcatagcga cgttttgccg gaatgctatg aaacgccagg   89220
ttccattgca tccaaggagt aatggcatgg aagcggttca tttgttcagc aaccacaagc   89280
gtgtctttac tctgagcaag gccgcgccga gtcatgaaag gatcaaaagc ctttctgatt   89340
tcggggtctt cggtcatcaa cagattctct ttggtgctat tcaacgcacc gaggtaatcg   89400
aacagtgacg gagcggccat aatattactt ccatttgatg ttgagcatga cgttagtcaa   89460
gaagtaaacg ccgtgcaacc agacgtcgcc gacggaacga tgttcgatct gagactgacc   89520
acagacgcat accagatcag ggattgactc gttttgaatc aaaggagtct tttccttgtt   89580
ctggggaacg cagaaatgga agaaacggga ataaaaatct tcagtgatgt agttttggtt   89640
gtcggtcacc cactgcttca tcccagccca atcattggtt tttaggaaat ccaccaacgc   89700
ttggaattcc cctgctttaa cctgtgccag agcgcgttca tcgattttac caaacgtggt   89760
```

| | | | | | |
|---|---|---|---|---|---|
| ggcattatcc | tgaagagttc | ccataatttt | gcgattatct | gggaaatatg | atttcacaat | 89820 |
| ggaagcaatt | acaccagctt | catacggaat | gccttcctct | gtcaggatag | ttgcgcaacg | 89880 |
| acgcatgaat | tgaagtttaa | cttcatctgc | ttccttttca | gaccagataa | aatcaatttc | 89940 |
| gcgacagcgg | gaacgcagag | gttcgttaac | gcgctgtttc | gcattagtcg | tcaggatgaa | 90000 |
| ggagcagttt | ttggagactt | tctctacgat | gcctttcagg | gattcctgtg | ccgccataga | 90060 |
| aagtcgctca | acttcatcaa | ggataacgac | tttacggcca | ccgaaaacac | tgacgccagt | 90120 |
| tgcgtattga | ataacacggt | cacggatgac | atcaatgctg | ttatccagtg | acgcattgat | 90180 |
| catcaacggt | ttgatacaac | cgatttcgtt | gcaaacagcc | agagcagaag | tagtcttgcc | 90240 |
| cgtaccaggc | tgagggaat | agaacagcat | tgagggatg | ttccattgc | ctgatgtaac | 90300 |
| atagccatgg | atttttgcac | ggacgtctga | agggaggacg | atctcatcca | gattgtcagg | 90360 |
| gcgatatttg | ttttcccacg | cgtattgatc | tgtgacgata | gtgatgttag | acattgcagc | 90420 |
| ctctttagat | aaaacgtttc | aaagggcggg | gaaaccccg | ccaccgataa | taaagcgccg | 90480 |
| aatcgttatt | gattaatcca | gctgcatgcc | gacgtaatag | ttgatggtgc | cgtctgcgga | 90540 |
| ttggaagtta | accagttgca | tttcggcaca | ggcgcggatc | acgtagttgc | cttcgatcat | 90600 |
| tttcaggttg | accacatcaa | caggcatagc | aaaatcaccc | agagttgttt | cacccaactc | 90660 |
| aacagtgtaa | tcgttggaat | tgtcgatagt | agtggtcgtg | cccaccagac | gagttttacc | 90720 |
| gccgctggca | accagacgta | cagttttgtg | gcccagagta | aacaggcgc | gagtcagctc | 90780 |
| tttcattttt | tcaggagtga | ctgttgcttc | aaattctaca | gacggaagat | cgatgctgtc | 90840 |
| tgccggaacg | acagtcagtt | ctttagcgga | acgccagaat | tgcagttggg | agttttcacc | 90900 |
| tttcagcaaa | atgtggtctt | ccgacatttc | aattttaccg | cctttaaaac | tcggcagacg | 90960 |
| ctggattgcc | agcaatttgg | tcagatccag | aatcgggaat | tcgaacggga | agtcttcgtc | 91020 |
| aatgtcggca | atagcgataa | ctgtactgga | atcgttaaca | gtgcgcaact | ttttaccagg | 91080 |
| tgccagaacg | atagaggggc | agatggtttc | aaagttagcc | agcagttgta | aagtgcgttc | 91140 |
| ggagagagtg | atctcttgca | ttagttgtat | cctcaaaata | tagtgggtt | caagtcatat | 91200 |
| ttgacgcaaa | ttagtatcgc | gtgtttgtag | ttatagaaca | agtgataaat | tgccctacgc | 91260 |
| gcgataaata | aatgcctgac | ggcatttata | atattctgtt | ttaataaaac | cttctcttat | 91320 |
| cagtctactc | gcttcgctcg | tgataatact | cgttgctcgc | aaagctcaca | actcgtatat | 91380 |
| tacgcacgga | ttgttcaaca | agaaagcgat | ttttattcaa | caattaaaat | attttatttg | 91440 |
| gtctaaacag | agcatgacat | tattatgtag | ccaagtttgc | taacacgcga | gaaatacata | 91500 |
| tgaagcaatt | tgttggttta | tacgcagtag | gggaagacca | agaagcaatt | ctttccatat | 91560 |
| cagaacaacg | ttcgtcatta | aaaggcgttt | atttacaaag | cctttctgt | acatcggggt | 91620 |
| ttgttgtgac | accgatgatg | gtgataccat | tactcccaaa | taacaaaggt | ctgtatgttg | 91680 |
| gcattattca | acaaggccag | gcgcgggaag | tgaaagttgt | tccattgctg | gcatctaatg | 91740 |
| aagaattgtt | ttctcagatt | cttgagccga | aagtgctaca | acaatgtatt | ggcacgatcg | 91800 |
| actgtttatt | tggttccaac | aaagaaggcg | aggcaacccc | cgcctatgtg | aaccaagatc | 91860 |
| tttgaaatag | ttagagcgcc | accttttttca | ttttaacagg | gtggcgctcc | ataagataaa | 91920 |
| atttatatct | ctcatgagaa | tgcctgagag | catggttgta | ggaaccgttg | tagcgcaggt | 91980 |
| tgtctaccag | gtcccagatt | cgcgcaacat | ccttagagga | atgctgacgc | atcaaacgcc | 92040 |
| ccaatgtctg | tataacacgg | atataagatt | tgctgggatg | ggccaatatc | agatgatgga | 92100 |
| gtttttttgat | agatacgccc | tgttgcatag | taccgtatga | agccaacagt | gttatatctt | 92160 |

```
caccttcttc catagcagcc tgaatctgtt tacgaacttc tgtcttgact tccccgttga    92220
tgacgaatac gttttcttg actgccgata gcatttcata aaccaacatc atgtgtgcat     92280
cgatacgttc gaacatgacc gccacgttcc ctttcaaaga cagagccatt cgggctatca    92340
attcattgcg gcgttcgtta gcaatgagaa attctatttc cttttgatac tcagcaccgt    92400
gcatttcaat acagtctgcc ataggatgta tgacttcaat catattaaca ttgatgtctg    92460
ccgcatatcc tagatcgatt aaatcgcgcg ctgtaataat tttatgatat gcgccaaagt    92520
gagcaacgac ttgtaaccct gcgacctttg tattcgccag ggttccggtt actcccaaac    92580
gttgatcagc gttaatacag ttgttcaaga tgtaagacaa tttatctgat tttgatgtat    92640
gtacttcgtc gacgacgata tctccaaatt gatggaacca ctctttgggt tggttctgga    92700
taccttgcca agttgaaata actatggggtt tgaaaatctc tttcgttgcc ccttcgtata    92760
ttgtctggac gttcatcaat ggcttccatt ctgtcccgtg gctatattct tcgaagttgt    92820
catacaactg agtcaccaaa tgaatggatg gtacaacgat taacgtcctc agattacttt    92880
cgagggcatc tctgcgttgc ctgtagtaac gcgccatgat gtacaaaata aaggatttac    92940
cagcactcgt ggcagcttcg aggacacatc tactttgccg tattgctgtg caatagaat     93000 caaattgata ttcgcggaca aacgcttttt gatattgttt gttttcgtct cggtacactg    93060
cattcaatgt atcgatgaac gcatgaattt cttcatccgg aatatcttga atatatttta    93120
aggccggatc taatttgatg gtgtaaccgt tcatcttaca gaatttgaac acctcaaata    93180
acaggccgat gtcgataagc ccagaactct ttgtgaacaa ccgcactacg ccgtcccatt    93240
tactgaacgg attcggttgg aaattaggat cttcaaattt gaagtaatcg ttgagttctt    93300
cacggatata atcctcggca aggatccgca ttctaacttc gttcactttt actatttgga    93360
tctcagacat cactaatttc ccccaatatt atggagtatt tagcgatccg cccagattcc    93420
gttctgttct ttatccattt tgtgatacag acggacacgg tcaaacattt tagaaataac    93480
gtctttgcga tcgaattcga ttatggtggg aacaagggca ttttcgttgg atataatatt    93540
gattaaacgc tctatcttga cattaaacat ttgttgaaac atgacggagt atagacacaa    93600
ttgaatacta taatcttcta tcatgcttcg agttttagg gtgttagatg ttttgaaatc     93660
gattatgctt ggaattcctt cgtaaacccc gatgaggtca acacgaccag caagacccag    93720
gacttcgcta tataatggaa tctcttgtgc atatatcttg ctcattttgt taaggtaggg    93780
gaaaacctgt ttgaacataa acacgtattc ccctgcagct tccagaactt ccttcattgg    93840
tctgtttttg agatacaact cacaagccaa atgaagtttt tccccacggt ctgcgcaacg    93900
atgtgtttct atatcagcag cttcatgccc caacttgtcc cgccaggctt ctaaccatgt    93960
gtggtcacca gtacgcccta acatggtcgt cactgaagtc agtttgactc cagtgggaga    94020
aacatagtga cgaccatttt cggtagttac gcaagtcaat tccttaaaag gcaaggaata    94080
ttgctgaaat gtatgatgac gattttcaaa gtcattaagt ttgcgcaaag cctgtagaga    94140
aaccattaca tcccatccaa atattttcgc caatcaatag cattcttcac ttcatatccg    94200
agtttgttca aacgatctaa gcaacttcg atgaacttga ctttggcttt ctgctcttga     94260
agcatgctag acaattcgat ataatcatca tctgctttta cccaaacatc tatatcagat    94320 ttcagggggtc gaactttaa tgggcgttca acataaacgt tgggcggcaa ttcccctgca    94380
taaaatcggc gtaaatagag atctatttgg cgaaatttgc cagttagata ctccagtatt    94440
cttccttcac gaatataatg gcgttgcaca gtcatccacg aacgaccaat tttcaatgac    94500
```

```
atttggtcta agttcatgtc ttcaggattt accgaaataa gaggttccaa ttctgccatt    94560
atatcttcgg ttttcatcgt ttcaagtttt gtttcgctca tgatttattc cctgctgttt    94620
caactctctg tattataact tattgtttat caatttcgcg ggtgacgcga gtcggagtca    94680
gtttcaaata tttgaacgtg acagtcgtga ccagttgggg aaccgcagca tccacatcca    94740
ccaatacgtt gtccaaagct gtgggacggg cttcttccaa caacaattgt agaccaacag    94800
ggcgattcat gttatcaaga aggtcgatgg tgatgtcacg gctaacagct aaatcagatc    94860
cagcattaga cgcaatccaa ttgtaaatct gttcccagtt gtaccaactc tcatcgataa    94920
cgaacgtaaa tacgatgggg tcatacgtga cgttctga aggtatggag ttgagcacat    94980
cgccagggga tggtccctcg ataccttcag aatacactcc aggaatactg aagtcatgta    95040
ttgaacgagt aagcaatatc aggtctccga tagttaagcg ccatttatcg gaagccgcga    95100
aattaggatt ttcgttttg aattgtacac ctgtcatgtt agcacctttg ctgtggagaa    95160
cgttttagtg ttcctgatac gcggattcag aaaatggatc atgacgatga taatggtgct    95220
tgcactcaca agttgccgta tctttgtcac gtccgtcatt tctgtaaccg acctctggga    95280
tcctgaaatc agaaccatac ctgttaacat ctcagccgac attgataaat gcaataaaaa    95340
tattctgaat caagtagtat ctgattttca gaacttccag actcttcaag ctgttggttg    95400
ttttgatgat aacaaccagt cactgagacc atactggaaa accacgattc ccctattgag    95460
gaaaggtgac gaaggaaaga tcccatatct atccgcaagt atttattact ctcagaataa    95520
tagcatcata gcgactttca atccttcttt ctttgacaaa ctcagaagga atactcaagc    95580
aagggacgtc gaaatcacca gagacgttgc aatatcattt cagatagtta ataacaccaa    95640
atctccgatt cgaattgcca ctcagggtgt tttcgttaat ggatctgctg tgggtaatga    95700
aatgaacatc tatgaaataa gaccaggcgg taaagtatgg attcgaatga gtgatgttgg    95760
ggtgaactcc ctggtgatgg aaggtatcga accagtggga gttctccccg ctagacattg    95820
attatttcag ggactctttt aattctggag tccctatttt atcaataacg cctcagcac    95880 agagatcttt agcccattct ccaagaacat cgcaaaaga gaagtttaga cattctttga    95940
tcatactttc aatatgagca agttctgcag ctatcccatc ggtgatatcg tttataactc    96000
cattgacggc ggttattgcc tcattgatat gtcctgttac ttcagcagcc aattgctgta    96060
gttttgccat cccttctgag gcaccttcca taatcatgtc atacaattcc gatatcttgt    96120
ttgttacggt ctgtagagca ccttccatag cattcagcca ttggcgtcct aaatcctgaa    96180
caacaccaaa agccttgttg atcaaatcac aattgtttgg ctctcgtgat atacccttca    96240
gacctgattt gtatgacacg gaagtaccga tgcgagaata cgcgtcattg atactttggt    96300
cgccatatgt gttcagtgtc gttatccccg tgttggcggt gctatacatg gtggtggctg    96360
ctgtgagttt ttctggtgtt agtccaccag caaccatagc cgcctgcatc tccggagtcg    96420
cgttggcagt tatcaatggt atattggtac taccactggt gattaaatcc tgtgagggac    96480
cggagaggga cggaagcggg ttgctaaatg cgttaccaga ggaaaggaca tcgtagattt    96540
gtgcgttcat aaataccccc aattttgggg gtatttataa tcacggaaga tgatagataa    96600
aattctcgca gaactttttg gtgtatttct ttagaaatat aaatttaggt tcgcgtggtg    96660
tatctttcag atcatttagt gtgatataac tgattcgcgc cagaaagtac atggtaaaag    96720
cgacacaaag aatcaaaatt aattgcagca tagctaactc catatgggtg tgaaggcaaa    96780
catatttata caatcgtttt ggttttgggt ttgcccatga gagtgatatt gacattgact    96840
cctgcttttt tcatgcgggt aatcatgtct tgcgtcccag tagacgaacc atcccataac    96900
```

```
gcaattccaa agacctcaag acctttttgt ttggccaggg ttgtagcttt gtctaacata   96960
tctttgttac gttggtttcc tgcgcctttc ccatatatcg tgtgataatc cttagggatc   97020
cccattggcg taacatggac ataattgatt tcacaccaat cacgagatat caagtccaca   97080
ccaaccgctt caccttctat aaaagtttcg atctcgtggg gatctaacag ttcatctaat   97140
ttggcaaata ttttgtcccg ctcagttata gaacgggaac ccgttataag aacgatatac   97200
ttcttcatag aactcacggc accccaagat tgctgatgac gtacaggctg catagcgggg   97260
ttcccgatga acggggttct atgttcatcc ctgataggcg tatcagttcc agcaaaccgt   97320
cggtggtctg atacgctcga gtcgaaccgt tcggacgata tagctccaac tcggttcgcc   97380
cttcctttaa tgcgttacgg atgcgtgtga atacgctgtg gtctccgaac ttctgcttca   97440
gaagatccag cttagtggtc aggcgacggc gaggtttgcg agtgcgtggg ttctctttca   97500
cgacttcttc tgaaattgag atgctgttga ccatgataaa gtcctctatt tgtagggggat   97560 agggtatgca gttaacatac cccgttcaaa ggtttagaac aaatgctcac cttccacatg   97620
gtatgctaac acgccgtcag aacattcaaa atacatgtta tcatattccc acagagcggt   97680
gatttcttca ccctggcaaa ctactgaaaa cttcggctgg ctagccttaa ctggaaattt   97740
ttcaggggaa gagattggag tgaatttggc atttccgacg gccataccaa caaattgctg   97800
caatgttact ttgtaacgag agtgagtgat agtgccagca ttcagggctt cggacaattg   97860
cgctttagtt gccatgatat atttccttca tttcagagtc agtattgtgc tgcttatgga   97920
atgaagtata cggggtttat tgaagaagta aaccccgttt attgaataat ttttaaattt   97980
atttgaagcg atcaggaaga gtgtcgtgaa cctcagcgct cagcaccagg aacttgccgt   98040
ctttagtagg gaagcagtag tcttttcttga tgtggcgcat gtgttcagcc gtagccgcta   98100
cacagtcgtt agtcacgtcg gtcttctcac ctacccacat actggttttg gtattcaatg   98160
taccttggaa gatagtgccc gtcaacgggc ttgctccaat cttttttgatt tcataatttt   98220 ctcccaagtc catgtttgcg ccttggcttt tacgactact ggaacgttac ggtgcatgtt   98280
tctgaagctg cctgtctgat aaaaacagat cctgatgcgt tcattttcgg tatgctgtgc   98340
ccaaacatga tgaccgtctg ggtatgggtc gtgaccagcg ctacctcctt gtagagctgt   98400
tttggtaacg acataatgcc cttgcatgta accgaagaat ccctcagggg tgatataacc   98460
agagtccgtt tgccaatctc ccttgcaatt agaatacaag aaatgtttag gcacctgagt   98520
ttcaatggtc atttcttctg tgagaacgaa cacatcgccg acttgaagca gtggtaaatt   98580
gctcatatat taatctctca catgttgctg attttaaata aagtcggaac atagcacggg   98640
tgttgttcac aggacatgaa ggtatcaaaa cgggaacctt taaccaagcc aggcagttcg   98700
cctttcttca ggagatcacg cactaactct tgcgtgtcat accaactttt tgctggattg   98760
gattgggctt ctgaaactcg gattttcaac tccccagtcg aataatattt accgctttcc   98820
ttcatataat aaaggttgac ggtcagatat tgaggagaat ctatttcttc caaccgttta   98880
tcaaccaagt cttggcggtc attgtcgtga ctttgataat caatgtcacc gctggccaat   98940
ttatagcatt tgaaaatgcg aaaaccttcg ataggtgtat cgatgtcgct acgaaaaaac   99000
tgggaacgtc ctggactaat aaagatataa ttttgtttag acatgatgta gttctctctc   99060
caaagtgtta tgttgtgaca gttgggtaat gatggttcat tacccatttta ttgaaaacat   99120 taacaattat ctttagactc gtcttcacaa tttgggtgat aaaacgttcc cagtttagta   99180
tggatgacgt ccatgtgggc attgattcta tcgatgatat cgtcctgctc tccttgtatg   99240
```

```
ttaaggatag caccaacaag acctggattg tgtgttgatt tttcttcaga atcagattcg   99300
ggaaattcac catctaattg tcgacgaata ttgatcacat tagtgaggat gtcaaaaaga   99360
cgttcttttt gggtgcggga attaatgagg atttgtgaca cggattgttc agaggtaata   99420
tttcggttg tcatgactga tactcctgtt gtaagaaagt tatatcgtac aacaggaatt    99480
gttattgaac tattcgcgta ttaaatcgtt acgataaaca atcacgtatt ttgagaaaca   99540
tatttcagat atgcgtattt gtaaccttcc tcggtgagta cgcacagatg tgtatctcga   99600
ccttttggta cgttttaac atcaactcgt ttacaaaacc ccagggaggc caattcggct    99660
tctccagatt tagcaggtat ttccccagct tcacgaggtc caaaccagaa agaacgaat    99720
agagtatcga ctgcaccgcc agataattga tgagacattt taacctcctt tgataaatga   99780
gactttatta tcttacatat ccctataaag aaaaacccg ccgaagcggg gtttgttatc    99840
aaaacctgtc gattagaaca gagatttgat caagcccttc ctgaagtaag ggttgctgtc   99900
ctgagcaata ccgtcagcag tcacgtaaac ctgcgggtct tggttagccg aatctgtac    99960
gaacgggtta gcacagatgc cgtaacgggt tttgaacgcc atacgcggag cgaaggtggt  100020
ttcaccctgg gtgcggtaca tttccagcgg cacatacggc gcgaagaaga taccggcatc  100080
cagcgcagtt gcgcctttgt atgccagggt gatatattct gctacagcat acgggtcaac  100140
atagacgcgc ataccgttgg acagaacacc agcgaaggtc tggccagtcg ggtcaacagc  100200
cagtttagtg ttttcctgca gaaccggagc atagtccagc atgccagaca tcgccagagc  100260
ggatgccacg ttcggagaac acagaacacg gttgccttta ccacgacggg tgtcaacacc  100320
gataccgttc gcttcaactt ccagcatgaa agtcaggaac ttccattttt ccagcgccca  100380
acgaccggag atgtcctgcg cgatatcaac aacaccgttg gtgccgaatt ttttgaagcg  100440
aacagcactg aagttcatgg tacggatgaa ttcacggttc atttccgcct gaatttcagt  100500
taccatcacg tcagacagga tattatccac gtcttcgccg tgaattgcca tcatgtcctg  100560
acgcagttca tggctgtaat cagcgtacag gccgcgagac ttggcagtaa cggtcgcttt  100620
ctgaacagtg ataccaacac gcgcccacgg attggtggta gtacccagca gttcagcgtc  100680
acttgacggc ataccttac cgatagtggt cacgccagag ccagaacctt cgatttcagc   100740
ctgactaaag ccagacgggt cgccagcctg tacagtacca tcaccggaat agccggaatc  100800
ggcttcctgc atgaacagtt cttttacgaga ctgtgcggtg ttggaactgt caccaacgcc  100860
ctggcgagcg cgcagtgcaa agatctgacc gtcaggacca gacagcggct gaacaccgaa  100920
gaagtccatc gcgatgttga tcggcgccag acgttttgcc atgtcgatca gaactggctg  100980
ccatttaccg acagtgctgt tcacagaacc aggtgcgtca gattcgccca ggttttttgc  101040
gttccattca gcctggttct gcatcagacg gatggtacg ttttcggcag acagaggttg   101100
aatagcttca gattctttt ggagaactgg cagccactgt ttgcgcattt cttcggttac   101160
aagtttctta gtcatgatgc tcgttcctta cattgatatt cagttaagtt gaaattactt  101220
agtagttcaa aatcaagccc cctttcgagg gctgtggctg ctaaaattag ccgttcagca  101280
aagcactgat ctggcgacgg acggcttcgt tgacttcttt gccaacttcg tctttgtcat  101340
catcgtcatc gtcatcatcg tcggcttcac cttcttctt cggttttta ccttcttga    101400
tgtcttttc agacttgtcg ccatccggct tgccttttc attgtctttg ccgactttat    101460
cagagaagtc atctttgcct tctaccaggt tacggaaggt gcgcacacgg gattcaaatt  101520
cagactcggt ctggaattca ataccttcca gcaggttgac aacagtgtct ttcttggtgt  101580
caaccatacc ttcacaaata cgatcaatga catcattgcg ctggcgtttg gtttcacttt  101640
```

```
ctttgagctg agccaattca gtattggcaa tgctggcgcg tttctctgct tcagccaggc   101700
ggttggtgag agctgcaatc tgaccgtctg ggtcagtagc gaaactcaca cctgcttctt   101760
tcagcacgtt ggagaaacca gtgaggaagc gttcagcagc ttcagttttg atctgagcgt   101820
caatggccgg agcattttg ttagcccatt cttcaacaac cgcgttgagg aacgaatcaa   101880 cttttccgc caactgaaga gtgaaatttt ctttaaggtc tgcgacttct ttctggtggg   101940
cttctaccag agtcaggcgc tcaacgttac cagccgcttc agtttcttga atagcttgca   102000
gacgggcggc ttcaacttta gattccagca gaccagatac tttgtccaag aaatcggtgc   102060
tgaggccatt aacgccttca aacagttttt gcaattcagg tttcatgata gtttccttct   102120
gaacgatttt tcagtattta gtgagctgaa tttcagccca gatgattcaa tgctgcatca   102180
aggcggcgca ggaagtcgtc ttctacttga atattggctt tcaccaactg atcaacaacg   102240
tttcctttaa catcccgagg catccaaata ccagaagcct catcaagctg ccattcaaca   102300
gattcactca cagccttaac ataacaaact tgtccagaag gacggtcgac tgcatcaaca   102360
gcggtgagca taaagccagg ttgaacgtcg tcataaccgt ttactgactt ggtctcaccc   102420
agaccacgtg tagacacggc cagattgaag tctgcttcag ccaatgcacg tatgatttgg   102480
ccttttggtg tatttaaaat tcgcgcccga ccgatggcat tggtgccttc ccagcgaagg   102540
gattcggttt tgagagctgc ttccaccaga ttagggaaag gatagtcagg atgtgtgact   102600
tcaccgattg cgcgacgatc ttggatatac tctttgtcat atgcttcgac agcagggata   102660
cccactttct gtagatcata gttacgcccg ttccggttta cttggttaca catcacaaac   102720
ggaccttcga tgaacatggc cttcccacca gttgaggtcg tatcctcacc gatttgaaga   102780
tccttcccta tcgctgtgat ctcacgcaac agtttcatca taaactcctt acttgttctt   102840
actcagtccc atcattttgc ggaacttcat agccttttc ttacgacgct cgattttcg   102900 ttggtagccc atacccatac gcttttgga gcgaagagct tttcggttgc cgattttgcg   102960
cacacgacgt tcgctggcat ccatgacttc acaacgtgaa ccatcagccg acaatttgaa   103020
cccaggggca catttcaagc ggcggcggcg tttaccacga gcgttcactt tatcgatgac   103080
tcgctgctcg tccatacgag aggccaggaa atcagcgaac gtggcgatct ctgtgatttc   103140
catcatgcat ctccttactg gccgttgttg tttgaattca tatcagctgc gatagaatcc   103200
agaacatatg ctgtgccttg gtttaatagt tcttgactac gtgcatcaag ttccatgttg   103260
cattctgcaa cagcagtttc agtgtcaccg tcaattactg cacgaacgat atcaattgcg   103320
ctcatgattt tgatctccga attaattttc tatatttagt tgaactttaa atactatcgt   103380
ctgttgaacc ggagaatggg atagtctcag gtttaaactt caacggacta acatctgaac   103440
cgctataatt gccagtttca tctgcttgaa ccttcggata gagacctttc ttcttctctt   103500
ccgcgatctt cgtttgttgt tctttaactt cttcatcaga catacgcaat acatttctca   103560
tgacgtagtc tatggagaaa atggaaccaa caaatggctc aacagtgttc aatgaagcca   103620
gacgatcatt caagatagcg ttttcttgtt gttcacgaat gtaactatcg gatgtgaatt   103680
caaactttat aaacggtttg atcttctcat tccaatcctt ttcatccgta acgcctttca   103740
aaattaactg gcggcgcaag aattccataa agaaatggga gtaacggcgt cgtaacccag   103800
cacagaactt gctgaagcgc agctcttcct gtgtaatctc cgcaaggtta gaaccccccaa   103860 tgttaataga tccttcctct tggaggcggc tcttagggat cattagagca tcatagagtt   103920
tttcacggaa ataattcaca tggtccattt cacccaattg attcccacca ccaacagttg   103980
```

```
caatttctgt ggcgttttgg ccttcacgac gaggcaacca ataatcctct gcaataccca 104040
taagatgggc attacctgtt atcttaccag tggtgcggtc atatgcgttg cggttttga 104100 atttacccat catcatggtc atgtattctt cagcagattt cttaccgaga gtaccgacgt 104160
caagatagaa tgcgcgtttc tcaggggcgc gagtgatggc ataaattaca gtcgcatctt 104220
cagtcgtaac caggttgttc aacggacgga tagcaggatt taaaaggcct gggacaatac 104280
cattggccaa tggctcttca ccactatcga tgtaaacaat gctttcgtca tcgaatacga 104340
gttcttgctg tgaaggctgg aagttttgag aagtaccaga ttggccagtg aattggtttc 104400
gattataatt cggggttgtaa taatacttca atgttacaga ttctattgct tcaataccgc 104460
cttcacgcat cgccttctca acgatataga caggacgaat gcaacgagaa tcaagcataa 104520
ccaatttctt gatcccgcct tttttattcg tgggatcaac gatgacatga tatgcttgtc 104580
gaccgtcaac ataccatttc cggatcttct gatatgctgt attgtcaaag tccatcaagt 104640
gcataacttc tttgaagcat tcggtgatag attctttaac agtatcagat atcccttcaa 104700
ctttgtcaag gtttactgtc actggagttt catcttcctc acaggtgaca acatcattga 104760
caataatgtc cacagctttg cgaatttcag gctgttgagc catggactga tattcttcca 104820
caactgtttt aacgctgaga agttcactct caacgccaac atagttgtag gtgtttgcac 104880
cgccctgaag gattatagaa ccgtcttgag catcgtccag agcaacaact gtcgccttgg 104940
tgagcaacaa ttcatcttgt ttttgggcta acttatcggt gtcgactttg cattgacta 105000 aaccgccgcc accaaacaaa ccgaagaacc ctctgccgta tccagccatg atctaagtcc 105060
tcaacatttt cttgtaatta gtgaggggga ataacattcc cccagcaccg aggacattac 105120
aatgacttgt cagaaacggc ttggaaataa cgcaagtcga cagtgaactg tgtgtaagag 105180
tccattgccg acatatcgag ttccagttgg ccgaggtttt gaggccagcc gccctgtaaa 105240
gtccatgtct tagtcacgtt gtcattcgcg tccagaagtt ccatgatgat atcacggaaa 105300
ataatcatct ggattcgcgc tggcgcggtt gttttcacta ccgttgatga attgctgcca 105360
cacttcaaaa gcattgtatg gagcgttgtt caccacgtta atgaacgtca caggaagcgc 105420
ttcgaaacga cgatcccctg ggaacggaag ttcacgacca ccccagggca ccagaatttc 105480
gcccagctga cctgttgggg tgttggtggt tacagccagc aaggacacgt cacgaattgt 105540
gtcggaacca gcaacaaaag aaggaaagtt tacagtcaca cgccagcggt gttggcgttg 105600
tacgccgccc cctcgtgaca tggctgcgcg aaactcattg actgtcgcca ttttatatc 105660 tccaaataag agtacacaat tctaattagt cgtcaatctt ttaatcttca aggaagaaaa 105720
atcaaatccg tggtcaacat tgcttaaaac gggttcgatt tcacacaatt cccaacgggg 105780
atctatgaga gaaacaagac caatgtgttc acctgtagat gtcaattttg ctgcagtttt 105840
acccagcata tgacttccat cattaccgcc tttattcatg ttgtaaccca tctcataaga 105900
attatattga gcgatgagtt gcttctctaa ttcccattta tggacttcat cggtctgagc 105960
aattacaacg aaagtaaatc cagacgttcc atacttacgc atagcatcat acaattcact 106020
ttggactcca tgatgaaaag cattcgcaaa atgctgatca tatcttcgtt gtgggtcatt 106080
ggtcacaccg atgtagacct ttccattagt tatcgtttca attttgtatg cgtatatcat 106140
tcaataactc aaatcaataa gacaaaggaa aaccccgccg aagcggggtt ggtcattttt 106200
atgaagcagc aacgatgccg ccaccggatt cgatttcgct gaactccata tccggtcgaa 106260
ctgcagcaaa atccaaataa atccagttaa tgctgtactc aggcttcaac caaatgccag 106320
cgaccatctg gtttgccgcg atgatgtcag cagtgttgtt atcttcatca cacttgactt 106380
```

```
taccatcgta aatcgcgccc atatttgcca gctggcgaat atatggacga accgcattgc 106440
tgaacagacc acgtgtaaac gcgtcattgt tctcaccaag atagtatttg gcgattgcgg 106500
cgatgttctg ctcagccatg atgaacagac cacgaacgtt gatgcggtca acgccgacg 106560 ggcgggtcag gccagttttg tcaccataca ggacgatgcc ttcattggag aaggttacga 106620
tgctgttgat ctgattgcgg tacaacacag cacgttcatc agaagacgca gaccacgcca 106680
ttcgattata gttgttgtat ttaccacggt tgtggaacgc cggagatttg tagatacccg 106740
cgatttcaat gcttcgcgcc caaacacctg cggtgccacc acaagccgga tccaacgca 106800 ttttgtcgtt gtacttgtcg tacacatatg cccagttatc atccatgaag aaataagaag 106860
agtcgcgaac aaggctttca cgccaagcaa cgacatcatc catttcacga ccacggttgc 106920
caacaaccgt atcacggagc ggggatacga aagataccgt atcttttcgc tcagtagata 106980
agtcgatcaa tgcttgttgc tcaatcagtt cttcacagta cgcaaatact ggcttcgcat 107040
catatgcttc agcattgttc aagacttgga tagccgccac gcggttgatg ttataatcgt 107100
ctacgccgcc ttctaattca acaacacctg cggccagagc ggtagcgaag gtgtacaccc 107160
aatttgatgt atcattgatg acatctttga agtacgcatt cgcgccatcg gatttttag 107220 aaccctgggt gttctgcatc agttcgtatt tttcaatgat ggaaccagaa gcgccaacag 107280
tggtaatcac ggctgttgca gtcagtcctt tgtcatcagg aacgatagct gtaacggcct 107340
gaggaccgat agctttatgt gtcacgatga cagtgttgga cttcacgaca acagaagaat 107400
aaacacttgt cagggaagtt agtgctgtac cgattttggt tgccaaatcg gctggagtat 107460
cagtatccag atatgcgata tcttcacctg ccacactgat ggtgccagca gcagtagccg 107520
taccagaaac ggagatacgg tcaacctgac cgaccgcgcc agcagagtcg gtaatgcgac 107580
caactttgtc tacgacaact acatggaatt caccagactg aggtgcgtat gcaaagttat 107640
tacggaattc ccaagtcgag aacccagcag catcacaaac attgatagca atatcattac 107700
ccagggaacc tggataacga ccagtccaag tgatggacgc cgaaggactt gctgtttcaa 107760
aatccagttt gttttgatc gcaatcgctg tctgaccttt ggtaacagag ttcttggcta 107820
gaggaccaac aacacgggtc acccatgcca tagagctgta agacaaaaag tccgcgatta 107880
cgagaaaatc ggtcgcagta ctgtcgttgg gttttgagaa tttcttcacc aacccgttct 107940
cacccccatt caccagccac tggaagttca atttccccc attgaaattt gccgacggtc 108000
gcgcccgaac aaacaacgga cggagacgtc tgaagcgtgg catcacgctc cgtccactga 108060
acggacggcg caacgctgaa gctttgagtt gccataatat cattccttct cggtagagtt 108120
tcgctcaatt tgaaagatat ttagtgatca attcttaaac cactcatcca tggtcatccc 108180
tgacatttcg ttgaaaactt gaataccccc gaaaccaggc aaatgctcag tttcggatgg 108240
ggtgtctcca acgactaaac caccaaatgg gaatacctgc tgagattcag ttgaagacat 108300
tcggtttctc atgtcctgag aaatacttgt agatgtcaag tcactgaacc attcttgttt 108360
taccgcccat gaatataaga ccaacggcat gacacagtca tcgtgacaac cgtcatcggc 108420
ttcataccga gcgcctttga acacaaatgt actgagttca tctatcgtgt cctggtcttc 108480
tatcaccaac atttctttct caatgagcgc tttcaggtta gcacaaccga tagatcggac 108540
ttttctgttg gtattgatac caggttccgg tttacgccca ccaatccgtt tccccgtccc 108600
tttgttatct gttgatgtga atatgatttc tggatattct atctcttgat aaagaattgt 108660
aataacctga ccgccgacgt cgttgtttgt ttcaacaagg acaggacatt ccccgtattc 108720
```

```
ggtgcacata tcagctatcg tgtatgcata catcatagga ggtatcgtgt tattcctgta   108780
cttggctgct ataacatgcg gatattcagt tatatccaga attgttaaga cggaataatc   108840
tccttccacc cccttcccag tgtccgcaat cccaaagtag agacgttgtg ggtcgtattc   108900
cttataaatc ttggtgaatt cattaggttc ccgatacaac ttggacgtca ttttatctaa   108960
gcatttggcc ggaatcaatg aacccacgga accacggaac ttaatgccaa attcttgatc   109020
gaaacgagca tcccccagac gagcgcgttg tttggtttcc caatctggat ctttggtgta   109080
cgccggaacc ttgtaccaag ggacttcggt aagatggaaa tcgttgtatt gtggatggcg   109140
tgggtcggct tttgtaacga tatcgtagaa caaccctcgc tggccttccg gagtactggt   109200
caggatacaa cgtgaagtat cagcagatgc gatcgctggg aatgttgatt cccaaaattc   109260
aaagtcattt tcgatgaacg ctacttcgtc cacgtacaag agagatacag aacgaccacg   109320
aatagagtcc gaagacgttg cataagcata tatcttagag ccgttctcaa actctatcag   109380
tgtagaacca aacttctcac aaccctgctg aaggaagaat gggaggtcct gatacgcctt   109440
cctgatacgg tcaagaattt caatcgcttg tttctctttg tttgccagta ccgcgatttc   109500
tttgtctgag tggaacatcg cataccaaag aagaaacgca gccacgaccg tggtattatg   109560
gctgaggaac ccattcgtgt aataacgttg atcgctggac ttgacttgca agtcatacat   109620
gtggtggtac tcaccagtct cccagatctc agagatgaat tctattccct cctgggtcat   109680
tatggcatct ccggcctcca tgtctttagc aaatacttcg cgcccatatt cattgaagaa   109740
catgtgctca tctgcgacat gaattgtgcg tccggtttca gtcctgacaa cgtattcagc   109800
gtattctttc gttttatgag cggcaataac cggaacccag ccagtgtcgg actcaacaaa   109860
atatcgtttc ccgaaacggc tgtctacaaa cttattgtgg ttgccaatgg tattcagtgg   109920
cacagcatgg ttcggtcctt cgaagcgctt gtgaagctct tctatggtga gatgcaactc   109980
ttgttgactg attgtatcat agacataaac aagagtatca ccacggacgc atttaccgga   110040
ctgacgagcc tggacgaccg cattgaatcg atagtcctga aagtcatgga acaactgctt   110100
ctgataatca tgcatatcga aaaggataaa gcctttatcg atcgtggtta tcttgtaata   110160
gttggcggcg aagtaatgcg cgtccattga acattcaacg aattcgtctt cttgttcatc   110220
tgtcagcatt aactcgactc ggggagcacg cacagaaggt ttgcgcatga acgtttggtc   110280
catacgcaat ttcacatcgt ctattttgaa ccccgtttta attggggcat attctatatc   110340
acgcttctga tacgccatcg tcttcttcct tcacatcaac tgtttcacca tcaatgattt   110400
catcttctgg ttgttgtgcg gcctttgctt gtgatctttc ttcagcgcga cggcgggcat   110460
cttcaatcgt cttcaataaa tcgcgagaag atcgcgcctt tttcccaacc gatactgttg   110520
ttgttccgtc tggtgaagtt gtaacatcca ctgtcgtgtc atcaacaggt ggttctttat   110580
cacctgttac tgccttgatg gttttctggt tttccatcaa gtctttattc agaccgcgca   110640
tgagttcacc caattcacgg aaaacagaaa atgctcgcgg agcttctgtg gatgcagcca   110700
atttagcggc ttgtcccatc atgaacattg tggcttcttg catggcatat gttgtgtcgc   110760
gtatccgttt gtaatccgtt gtagcatcag tgtccgcaaa ctcaggtact tggattcct   110820
tggaagcaat atcctccaat gaaggaggtt caggaatcgg ctgatacct tccggacgtt   110880
caccaaacca ttcacctgta ttttcatcga agtcaatacc tggacgaggg cgacagcct   110940
ccatcgcctc cttcccgact tcgtctcggg cggtcactgc atcaagcgtg gcgagtaacc   111000
tttctgacat attgctcatg atcaatcctc cggatgatgt atgccgtctt tatcaactcg   111060
gaaccactca ggaagttccg accatggcat gttcaaatca ttagacattt caataattat   111120
```

```
ctctttgatg acgtttggat ccccaccgcc cgaaccatca tcaacccaat aatcttctcc  111180
atagatgtga ccatgtaatt gaaaattgaa tgaacaatct atgtgtggtg attctgttgc  111240
gtccccttcc cagttgtcag aaatcgtgtg atttaccaac attatcttca cgttctgatc  111300
ttgagataaa gtatcgttgt cctttatctg acagtcaaca gaaggagtga acacagaata  111360
aatttgttct aatacttgca acatttcgac caatttttta gttctgatat tgtattcaaa  111420
atctataatg atcggaatgc gttgtttgga ccgtgccgta gcggtcgata tttggttgtg  111480
gtatgacttc gtcacctgtt tattgatttc gaactgacca aaggacattg ttgcaaatgg  111540
cagcatattg gctggcacgt tcctgttgag gtcattacgg cggccaatgg ccatatgcag  111600
cgggatttcc atcaagccac gttcggtttt gacttttaaa tctgacatga tagcgttgaa  111660
cacatgtatg tatttcaaca atgattcatg atagaaatat ttttcaaatg gtctggccat  111720
gattattccc cgaagtctat cttcatttta ttgggcgaaa gatctttctc tatttcgtcc  111780
gcaaattggt tatccgtttg caggctggcg tctttgtaca caccgtctcc ttccagatcc  111840
tgcaatcgtt tatcaatatc gtctatttca gatacacctg tatcgaaatc ttcgttaccg  111900
tattggaaca acgtacatgg tagggaatat gtgtaccatt tcccaaattg catgaattct  111960
tcatcgttat tcgggttatt cactttaaat attttgttag ccataggcag atatatcaaa  112020
tcaccttctt gaggcatttg ttcaaggcct ggaccattac caataacttc tgaaaaacga  112080
cgacgagcaa tagtgaatgt cacttcatct tgtaattgga taccgccgaa cttttcccac  112140
atctgtgtgt tgaagccttg ataatcctgc atatacactt cgatgtcaaa cgcttggtcg  112200
aatttgtgtt cggcctcgtt taaaattggg tatttttcaa caatagaacg tgggatatac  112260
ttgacgtcaa tcccacgcaa ttgtatcatc tcgaccacca agtcatcaat taatttttga  112320
gtaccttgat gtgctgtata gttgaaatat tttgaagtag ccatgacttt accctcaatt  112380
ttgaaggtat ttagtcaatc attaattctt ttgaggaatt gataaatgaa ggttgaagat  112440
attaaagaaa ctcgtgacgg aaggcgtgtg agaattatct gtgtagatgc taaaatcgcc  112500
gatggttcat ataacattgt gggtcttatc aaaggcgaaa agggaaatga ttttattgaa  112560
tggtgggacg aaaagaacgt ggttgatggt tatattctag caaattcaga tccttccgga  112620
cgcgacatca agttataaaa agaaaggcgg gataacccgc cttctcttat cccatcataa  112680
aatcaatggg gtattgctga ccagtacgca attcttcctc cagccgctct atctcggtct  112740
cggcctcact gaacatacta tcaccatcca gttcgatacc accagggaga cggatgcctc  112800
ttgccttctt aagcacctct gcccaacggc gcttgaccaa tgcagtcgca tacgctttca  112860
accacatatc attccatgct tcagcgtttt cttccgattc ggggtcgata ttttgataac  112920
aacgaaaagc cagagtttca tcaacaatgg cagcaaactg cgggtaaagg cgtcgctgga  112980
acttcttgta cacaaaatta cggcgaacat ttaagacgct tgtgatatcc gacaggcgtt  113040
gttgcatgga aacataatca atgagacgaa tagaaaccag cgctgctttg gggacaagca  113100
ttgcttgagc catttgccat tgaggagttg cccagtttcc gattgactca ataggaggtc  113160
cagggataac ttcaatcaca tcgtcaatat catcgggaaa ttctatatat cccttgtcga  113220
tatcttcttg tttaacttgg tacaggaaga acgcatcttg gctaccatca cgatgatatt  113280
cccaaaattt ctgcagagca tcatcgactg catcttcgac ttgtgaactg tcaaggttaa  113340
tttggatcac aggagcaccc aatttacgca agacataatt cataaagat ttttgtctc  113400
gaatcttatt gacggccatt gttattcccc ttttgctgca aatcagatac agtaatccgc  113460
```

-continued

```
agtgtgcgaa catcatctga aagactgctg ctattgagtt ttaactcagc catgttttgt   113520
ttgacatatg cgaggtcagt attcatgatc gccatacgtt cactcatgtc attcactttc   113580
tgaagaactt gatccatctt gttggaatct cgttccaata cattcacgcg cgtttccatc   113640
ccgcccatga accaaaggaa tgatgccgca gagaccaatg cagaagccac gacagcggtt   113700
aagataccac ggatgtcaag ccccgttctt tcagcttgcg tcgccattct gacctccttc   113760
ggggatttcg atccccaact tttcggccat cattttgatt gtcgcctcca gattagatat   113820
ctggtttgat tgttcaacaa tggtggcttc acgggtttca ttgcgttgac gggcttgcaa   113880
tgcagccatg ccagcggcgt gatcggtgca aataatcgcg ccagggcaag aactgcttct   113940
caacatggat gcgtgcccct gtactttcac tccacgcata tctttatcct ctattggttt   114000
ggtgggcttt acgcccacct ttcaacatta tttatgccag agcaataaga cggaagtctt   114060
tgaatgatgg aggagcaacg cggttccccc gtacaagcgc tcggactttc aggccaacaa   114120
acgggttatt gctcgccaca gtcttgtcat actcatattc aaagaatgtg aaccgtcgt   114180
taaccagagg cgaagttggg gtgacgtctt cccaagccac actatccatc tcttgccctg   114240
ctcgtagaag tttcacctgc accttcatcg aagactgaga tgggagcatt gcaccaaaga   114300
acaacttcac agtagaacac ggattatcaa atccgatgtc ctttgtcacg tatttgaaga   114360
catcttcaaa tggatccaca ccgtatgagt tgaagattac gctcaggtca tcgccatcaa   114420
tcattggagc agtgtacacg ttgttttcac tacgcgtcat ggtggctcgg atttggaaat   114480
ccccgacctg acgatagata ccttcagtcg gcaatgccac gtcagtgtca gtttcaaact   114540
cagcccaatc agacatagaa tttgaagtgg catcgcgata acggtattcc aatttcagaa   114600
ttgaaccttc cagagccgaa ttggtaacgc tggcatagaa catatcaacc agataattgc   114660
ccaagaaaga agcattatct ccaccgattt gtccattgct gtctgctgcc gtaccgacgt   114720
caatcttgaa tgaagtatag ctcgcatctg tcacagtaaa cgttttgtta agttgttcag   114780
gagtaaagcc acaaccgcct gtcaattcag aaagagtgac attgttccca gcaaccaaac   114840
catgaccagg tgcaaacaca gtcacaacag aagacccgct tacgcagttc agagtgttca   114900
atcccaacgg acgttgtttt ggcccgagct tcggatcaaa tgttacaacg ttctgtcccg   114960
cagcgaagtt acaacgatat atgcggaatt tcatatcagc catttggttt ggagaccatg   115020
tagaaccgtt tgaagaagtg aagaacaccc ctgtatacgg ttgtttggcg atatattcgt   115080
tggacagaag gttttctctg cccatttccg cgatatacgc gttgtaatcc tgagtattcg   115140
ccaacaaaac gatagcaaac tcagtcgatg cttgcagata caccggataa tcaaaggtga   115200
acttcgtacc gccggaagag tctgtagaga tcgtcacttc agacgggttc aaagttttac   115260
gagtaatgac tgtatgagaa ggtaagccat tctccatctc gcgaatttcc agagtgatcg   115320
gaacatcacg tgacttggta gagaagaata cttccacgcc ttcaatatac tcgccgccat   115380
tcttagtcgc taccataaac gattgggcaa tcggatcacg ccattggtcg accacaactt   115440
cagaagtgct ggtttcggtg cgagtactag cagtgtaacc caggacacga gtgttgacaa   115500
aggtcttttg aataccttgt ttcttaccga aagatttatg aacaatttct gcattggtca   115560
gtgtatcatc cgcagattta ctgtcaacag ggctatccgt taagcggaac acgttgtcgc   115620
ctgtgttgaa cttgattgta tcgttctgtg aacgcggaa tataccttta acagcaccat   115680
tggcatcagt ggtgattggg tcaccgaaat taccaccatt cggtttgcaa tacagattga   115740
cgtcacgacc agagaagaac gcatacatac gagtgaaagg tcgcagccca gatgcgtcga   115800
aagaaatatc gatctcgcgc atgtatggga taacttgcgt ctccacaatc tgttcaccag   115860
```

```
tcatggtcgt ggttgttttg tccgtgtatg tatatgtggt gacatcacgg gcagaaacag   115920
tcgtgcggta acgatatccc caccacacac caccagcacc atgcggttcc caaacacgat   115980
cagaaacaga aacagtacgc catgttccgt acactgaacc ttcttgtaca gtaccacggg   116040
tgttgatcgt ttcattgata atacgcggcg caacataata gttttcgaac cagtagtctg   116100
tggtcgggtt aatcttcaag aaaccttccc aattgaatac tgcatacggg ttaacgttga   116160
tcgtcgtcgt cgcatattct tggttcaccg agatttcagg cgtgtaatta caaaccacca   116220
tcccatccat cactttgttc cagccaaccg gagtcatgtc aacaacgttt tgttgtacaa   116280
acgggcgcag acgtccgttt tcggtatcga tagaacccat ccaatcttca gacaagtcat   116340
caatcaaccg gaagtctttg aacggatcag ccgcaatacc attttgaaa cggggattgc   116400 ccgtgatggg gtcgaacact tgctgtgtca tcgctgaaga ttccaactgt gacagagagg   116460
tatagtattc aacattggaa atacgggttt ccagtttacc gatatcgcgc atcgtataac   116520
gacgattgtc aatagtgcga atttggatat catcaatatt cggcgtatac ggtgggatca   116580
acaattcata caaacgcatg gcgttcgctg ggattgctgg agaagccaga ttattagaac   116640 taataccctcg agccacacca aacacaccgt tgtctgccag ataaatcgcg tcgatacgcg   116700
gcagataata ttctgtgtcc agaataactg cagtgtttgg acgaaccata tctgtgtcag   116760
aagttccgtt ggtgattttc ggacggaaat ccaaactatc tgccaggccg tacaccgcgc   116820
ctgatgtgga tgatgtataa ttcgggatat ctttataatc catcgaagta tacgaatcag   116880
cagagaagaa atcaccggaa ctgtgggcga agtattgata caccactgta tacgtccctg   116940
agattgctcc agcgctggat aacaagttag acttgtaata ccctgcatca cgctgtccgc   117000
catctaggac gaagctggag gtcacgtctg cgccagtatc gtttttgacc gacaccaatt   117060
tccaaccatc gtgattcgcc aaaggacggc tagtctgcga ggtgaatgtc actgtttcag   117120
ttgtttcagt gatggtcttc gttttgattg tggccgtggt acgaatcatc agcgccagca   117180
aattgattga ctggttagca ttaccactgc ccagagaaat ctgcagcgcc gaaccgaccg   117240
gagaaccagt caaagacaaa gaaccagaga tatcgaactg cgcttcagaa ccatcagatt   117300
tcgctgcaga gtacaacgaa aattctgggg aaaaactata tcccaatgga gcagaaatag   117360
aacccgcgcc gctgttgtcc aacgtcactt tatacgttct gagaacagtg tagttgatat   117420
ccacggagcc agttggtgct aaagtcttga caccgaatac cggaagagag aagatcagat   117480
ctatcataga actctggtta aactgattgg attccagttc agcagagaac atggtgatac   117540
cgctttcttc gtaagacact ttggtgatag tggatgcatc gccagtaacg accaggtcgc   117600
gcatatacag acgaaattct gttgaattac gttcagctga tatacaaagt gctgtagcct   117660
gggtaacgcc tgaagcattc agtaatttgt atcgaacggt gcgggatatc actggcacac   117720
ctttagaatt cttagtgacc agataattgc ctgtggccac cgcaacaggg gtgttattca   117780 ggacatcgg atcccgcgcc ttgtcgacaa taaccagttc ttccccgaca ttttcgtac   117840 gtcgaccgcg aacataggag atgcctggtt tcatcacaga aacaaatttg ctctcgtcac   117900
cgccatcagc ggcattgaat accccgccat tgttattgac tttcaggtgt tcgcggatgt   117960
cgatctggtg cgttgaaacg ttgtaatcgc cgttggtttc atacgtccgt tgggccaacg   118020
tgtcttccag aatattatag gtggactgag tcaccataga ctggatttta ccatcacgaa   118080
ctttggccaa ttcaacaaaa tcttcaacca cggcgtcata atcaaatcga gataagacca   118140
gatctattcg aagacgatga gcgcctgggg ctttggagtt aatcgttccc tgagcatttg   118200
```

```
aataaaggga ttcatcttct gtttcggtga caatagtttc ggtgacttta aatccgatgc    118260
ggtgggaagt gatgttagaa gttttatcaa cgataagagt tgcgtcatca acgtctagga    118320
acatcccacg aatgaagtaa acgcctttcg tcatacgagc gacgatagaa ccagttactg    118380
cagctgcgat accataacca atacgaatga aattatcatt cacgtcgtaa gtctggaaat    118440
acagattatc gttaacatgg aatccgtcag cattacccgc ttcagtcatc tcaaggatag    118500
ccagcatcgt atcaggagca gacagatcac gttcaagaga caacacacgt gctttggcat    118560
tattgtcctt ccccaaaacg tagagttcag aaataccttc cagatcagtg aattcagtac    118620
caccagccaa agtgaatttc aaagagactg cggcattggt aatcgtcaga ccgccaggga    118680
taaccataga accatctttg aacaaatggt tgcctagttt ttcaatttga tcctgaagaa    118740
tagtctgcat ctggttcagt tctcgagtct gaaccttgat aggcatcgga cgaaaaagaa    118800
tccgtgaaaa acgtttccca ggattccagt catcccaata cgggcgacgg tttaaatttg    118860
tagattgcat tttgatgctc catagagtgc catttataga gatatttagt atacagccaa    118920
caaacaggat agaaataaaa cccccgccga agcggggttt ttactatgat cctataattt    118980
tataggttag agaagtatta ccatcaactg gatcagcatc tattcctgtc ggtcttgacg    119040
ctgtcttaac catgacacca gcgatagttt gtccagctgt tgcacctaca tacttagaac    119100
aatttacaga atagaataat tgcctgtatt caatattacc ctgaatctca cttagtacaa    119160
cataggccgc accagaatcc actgggcagt tagtatgtat gtttacttt tccgtggtgg    119220 agactctaaa catatggccg ccatctgtag atataccagc aagcccaatt aatgataatg    119280
tcccaccggt tttgataagg aagctactac cagaatttgc cttcaagcta ccagtacctt    119340
caaaattaac catcggcaac tccgtgttag aggtaatggc tatctcacct gggttaagat    119400 aaaactctttt gcacttgaat agctggcata actttgaaat attaagtagc tctcttatag    119460
gtttggttcc gttaaatccc cagttgtagt tattaccatt tacaggatct atgtatagag    119520
tgtctgcttt tacaccaaca acatctttga tatagaaaat gtcaccaact tccccaaatt    119580
ggaattgact tcccatattt gtacagtcga gtaccaatgt agggtagtta ccagtacctc    119640
taacgagttt taaaccacct actggcattt gtcctctgac aacatttcgg gcagtttctg    119700
ggcagttttt aaggaagtac atactatcta gatcagggtc ttgtccggaa agacctaccc    119760
ctgacaacgt aacatctgaa ctggtattga tcaggtagaa actatgtttt ttcttcccac    119820
cagatgattc aatgtggggt ttatcaacca taaataaacc gtaggaatca gtatcccggc    119880
cagcgtgaac aaagtcgaat gatgcttgtt cgatgattgg gctattaaac ttaacctctg    119940
aacctgcaaa ctgagtgatg gcaacatcac ctacctcagt aaaccctgct ggtttataca    120000
ccgcttgttc tagctcacca ttggtattac caaggcggga aatgtaagca ttgtttacag    120060
tagcaccgcc attagagtca atgaacactg cgccctgagt tttatacagg atgcgtagat    120120
tttcatgaac agaaccccat gatgctgact gcaacaatcc tactcttggc agtcttgctg    120180
ttgtaatatc gctccctgta ttctccccaa tagataaccc ttttgtagtg caacctgccc    120240
cacctatcca tttaacacca accttacac ctggtgctgt aatcaggtta aggttactaa    120300 tatcaattt tctggcacat gttacagcgt acccattatc aatatctaac ccagtaggat    120360
aataatctac atctttattg agtttgtatg aaccatcagg ttgtttacgg tacaccatta    120420
agctgattgc tgctgtattc ttatctactg ggtcataaaa caatccttgc ttacactcac    120480
gagtaaaaaa gtttggtgct ggcatttcaa ttgaaacacc tggggtatg tatagcgtct    120540 ctgtgaatcg gtataacttg gtcaggttaa ttttactgc tacttgctcc atgtacgagt    120600
```

```
ttacagccgc agcatcagga agtgtttcag gaacgttgtt tatgtctgaa agcatttctt  120660
ttaattttga agtatcgtca tctattccgt cgcctaccgc attgtactgt tcaggtgtgc  120720
gcacagttaa tacattattt agcgttccct gcgggtgaat tccaatcaac gagccattgc  120780
cgtttgccag ttgtgttctc aaagaagcat caccaacact aacccacgcg ccaagaccaa  120840
taccaccagt tgatgcagga gttgaaccgg cagggacagc tttaggtaat gctccatccc  120900
agcgatactt accatctgta taagtgagta attcattttt aacgttaagc gtagagccaa  120960
aatcaaatgt cccagccaag gtaacatatt cttcacgaga tacagctaat gcacctaagt  121020
ctacagaacc tgctgaatgt acaagtacag cagcagtatt aagactgacg gcagtagtac  121080
cagaagcaat accagcaggt aaggaataag ctctttgcgt ttccttgtca tagataactt  121140
tatacccccc taaatctaca ccaaccgaaa agtaaacaat ctcagattgt ttaacaccaa  121200
agtgtctggc tactgcttgt ttattggtta agattccagt tgaaccttta ccaccttgac  121260
taaacatttc gttcataagt acctcattgt tttttctagt aaagacccct ccgaagaggg  121320
gtatatttt aaatagaaga atccaatata cggtaactaa ttaacttagt agggtctaca   121380
ggattaatca ggttgtagta tcgtgaagct acataatcgt tctcggaaga gaacatacca  121440
acatacactt tagcgcccac cccagaacaa gcatccccac cagcattgct atccgagaag  121500
aatgttaatg aagaagttaa tccgaatata gaattaaatg gtacggctaa ataagcgcct  121560
cggaatgacc gtctgattct cttacccgtc tgaatattaa gaatactcca ccagaaatat  121620
ccaggtttag caccaatagc tatatgatat ggtacaccac tttgtagttt aaggtcgtta  121680
ggtaaatccc cagataaaat ttgggttgta ccatcgcccc ccaatagcaa agcaattgtt  121740
tgttttccag aagcgtctat aactaattga agatgaagac tgttggatgt atcactaaac  121800
cctgaaccaa tggccatgaa gttaaatact tcagctccag atatggtggg tactacaaca  121860
gcagccatgg taataccttc tggacctgct gttcttgaat acagtaattt atctttgttg  121920
gcttgtgata gtctcagacc atttacttgc cctacagaag atgggacact tacataaaca  121980
ggtgtagtgc taacaccatc aaatgtaggg gtctcgttca tggtttgcaa accagtcttg  122040
gaataattaa ccaatccgtt aatgctcagg tcggaattgg tggggttgat aatattgtta  122100
tcaccaataa agttaatgcc catataacca gtctcaacca caccattaat ggtgacacta  122160
caatcattag acaggaactg aaaattgcct gcactagagt tagcacctga accactattc  122220
gcggcataat tgagtcctac gaatccgttg ataactgcat cacttttgtt aaatacgatg  122280
ttgtagaaag tgttgttagc attgatgccg ttacgattgg tgttcaatcc gttcatggaa  122340
attgaatatg actcgctaat ctcaatacca ttcccgccac aatcttgtac ctcaatacca  122400
ttaataacca tattctggct gttattaata gtaatgcctg gaaactgtcc tactgtacca  122460
taaggttgcc agttagccca aatgaattta ccgccaataa tacgaccatt accacaacca  122520
tcaagaacta gacattgttt accgcaggta ttaacctgga tatttgtcca agtccaatca  122580
gtagtagcac aacggacacc cacctgattg atgtggttga ctaaaagaga atctgtagta  122640
acactaaagt taccactatc aatatttaac ccatattcat caaaacctgc tatatggacc  122700
ttagaaatac acaagtcccg tcttgggtct gcggtagtgt ggaacggata tcggctgag   122760
agacctgaag gagtttctac atagatacct gttgtgcccg cagtaaatga cgtgccttgt  122820
tgtgcacctg tgccatatac cccaaaggcg tctaatacaa taagggagca tgtatctttt  122880
atggtaatac aattcccagt agcagaaggc aactgatgca accttgagta atgtaatcca  122940
```

```
gacccataaa tagacgacgt attatatttt aactggatat tgctaacgta atgtacacca    123000
gttaattgtg tggccttacc actatccaca caagattgta ctggaatagt atcatcatta    123060
gaaccaccca aagcaccaaa catgaatggg ttaactctat cagcattaac acgtaaccat    123120
gctgcgccgc caacagtttt gatcacagta ccgttattat cagtcttttcc tgtaccatca    123180 attaacgcac ggaataccccc tccaccaaga agagtacccg cagtgtgttg cttaagaata    123240
atgcgttgtc catccatagt gggttcagta ttcctgagat cagcaacaga atggcattct    123300
ccaatatact tggcaccatc atttcgcccc agagtgttta tcacattaat aaatgaatct    123360
tctaaaggca acaaatcaac ctgcacatca cctggattgt aattcaattt cccagcagat    123420
acagaagaaa tgacagaacc atcaggaatg gttggtaaac cataactggt ttgcgccgct    123480
atgtcataaa caactttctt cccatccaac aaagatatgg tgtccgtact aacgatgact    123540
tcagagtctt ttacattagc agaacgggcg atttcttgaa tacttcggtc aaacgccgga    123600
ctgatattcg gttgtttaac agacatttca gcgactaccc aaacgcctgc agtcagtgca    123660
gtttgcaaag atacttttcc tgtcgtactg tcataggaat attcaatttc ggggttttg     123720 tactcgccac cgatataaag agattggact ccataagatg tgaaatcagg agtgaactcg    123780
gtttcacctc ctacggcctg aaatttgtat atgcggatac ctttggctgt atcttctggc    123840
gaaagaattt tatcgaataa gcaatacaca acatcgcctt tggacaatgc gcgtccgaga    123900
ttcaatgtat ttccttcgat ttcaaagttg tctaacggaa cttgcatacc accgttgatt    123960
gtgataacac cagtgacggg atggaacggc aaagaaagga agtttctcc accgacattt     124020 gatttatacg tgaaaggaat ctggtgggga gctgtgatta cgccgccgaa taattcttct    124080
acatttctgg tcatttgaaa atacccccata aggatttgcc aatatggggt atttagtctg    124140
aactaataaa atttatgaac aaaggtataa taagaacccc gccaaagcgg ggtttttgct    124200
caagataaat taaagtgtgt atgttacata acttccatct ggttttttag caagcaacct    124260
caatgctccg tcacttccga agaagaatcc tatagatgaa ttatgttcca gagcgctctc    124320
tggtaattgt aaaggggcag caggtatact catatgctta aagcctaagc ggttaagctg    124380
aaactcacct acacgtacac cctcctgaat tgccgaaagc ttgacaatac ttgcctcacc    124440
ccctggtgta gcaacctggc aatctgccgt cataagcaaa gatgggtttg tagtaccacc    124500
catagcaggt tgcattgcaa gtgtcatttg gttggcacta tgctgaacat tgatattacc    124560
tccctgaata tcgcttatat aggtacatag taatttctta gtaccggaac cagcacagga    124620
aacattactt acttctgaag acggagcgta tatagcgtaa ctttgtgtag tatatgcatg    124680
gatgttaata ccacgaagtc tactacctcc ctcacagggt aagctgattt aggttagtta    124740
aatccttatt cgcaccctact ccagtaatgt tagtaatatc attgttagta ccccatcga    124800 agacgccttc cttatgggcc tcataagtaa caacattatc aataatattt ttctgaccat    124860
cccaccaagc accaatcccc atacaatcac gagtaataat attacggatg atatgttgag    124920
taggtaggtg gaaccatgga tactctgcga gtgagtagtc atccacacgt tcagttggcg    124980
accctgtgtc agcattaaca tcaataccat catagtaaca ctggattgta gttatattgt    125040
cgaacactaa acggtagttc ctggctgaac gacctccaat ttcgttctga taggttttaa    125100
tacctgattc tccaacacgg tatgagatta aatcccttac tccaccatca tggtctgtac    125160
caccatcatt gcgaatgaac agtacagcgg aaccagagcc atattttatc tcaccccccaa    125220 caacccagtt gccagtaccc catgcagttg tatgatggtt ctcaaatgta atgcccgatt    125280
ccaaagcaat aaaattgcgt ggattcttaa caagaatcct attacataaa gtaaatagat    125340
```

```
aaccaccaaa tgtagcttct gggttctcta cgatgatatt atcgccgctc attattcgca   125400
aagtagcacc agcaacctga ttttttacat tatcaggaag gtcgtcccaa atatctaaat   125460
cgttaatatt tggcttatat ccaacatcca aacgctgctg aacagatgcc agaacttgtg   125520
ttgggtctgt aacccaatta ccgtttgcat cgaatcggta aacagtatac ggcgtagttt   125580
tagtatgcat gtgcggtttc ttaattactg agcccgcacc caaaccattc caaaccaaca   125640
taccatcgcc aatgaatttt cctttgcatt caatgattaa aactttaccg ctaaaatcta   125700
cattctcatc tgcagtaaaa gtgtagtcaa catcaataag caatccatct acggctgctg   125760
tcgctgcatc ctgtaatgta gaataatcag ataactttac tgaatatttg aatttcttat   125820
tagcttcctg cctaaatgca gcatcaccaa cactaaccca agcacctaaa ccaacgccac   125880
cagttgatgc tggagttgaa ccagcaggaa caactttagg taatgcacca tcccatcgat   125940 attttttcatc atcgtgaaca agaagttcat ttttcacatt aatagtatgg ccgaaattaa   126000
aagaaccagg taaagtcaca tattcttcgc ggcttactgc taattcccg agatcaacag    126060 agccagaaga atgagtaagg atggcttgtt cgttcagact tatcgcagtc gttcctgaaa   126120
caatacctga aggaagagaa taagcccgtt gggtagactc atcataaatt actttaaatc   126180
cgctgagatc aataccgaca gtgaaataaa tgacttcgtc ttctttgaca ccgaaatttc   126240
gagcgataga ttgtttgtta acttctatgg aagtggagcc gcgtggttga ttgaattgag   126300
aaatcatgat aataccccat aaaggatgac caatatgggg tatttagtct gaattaacaa   126360
aattttataa acatggatat aataagaacc ccgccgaagc ggggttttta ctatgatgta   126420
aatttcattg catcccatgt tgtaccatta tgtcgatacc cgaaatatt tgatgcccca    126480 gcaataacat catatctgtc accagacgca ttaccaaaag gcctgtcagg aacagaagtt   126540
gtgtcagttg ctaaaatgcc tttaaaccac catccattct gggtgtttgg tttgtatttg   126600
taaaattgtt taacatatgg ttgagttggc gagtcaacat taatttgccc atgaatacca   126660
gcgtatccgt ataaaggttc actggtattc acatcactgt atacatcaat gttgaagtag   126720
taatcctgta cggatagtgg agctatccca agcgctggat gcatccatct atctgttta   126780 atatcagcag tgaattgcac aacaccaaca gtcactcctg ctgcttgttg caataaaccc   126840
aggacaccac caaactgaca tttttgtcata ttccatttaa tatgcatttc atcaaggtga   126900
acaagataat cgttggcaaa tttattggta aaccttatgg ctgtgttgtc tgataattga   126960
ggtgaaccgt tggtcccgca agagacaaaa gagtcattgc tgttgaaagt agcacctgtt   127020
ttttgtttac ccaagcgaac acaccccaa aaacctgaga aagtgttatt ttcactaaca    127080
acttctttga aatagtccag gtcataagca acgtttgcag ctttttgttc agttgtccaa   127140
tctgcggctc tgttttttg caatatgtta ttatttgcag agtaaataat tgcattaata   127200
gtggttgggt cagatgacaa aacagacggc tgctgtgttg tgaatgccgc agtattagga   127260
tacccgataa cttgcttttc tgatcgtagc gttacagtat taccaataaa tctggcaaca   127320
gttgtaacgt taggtacggt atccagaacc aaagcactac ctgcgtcctc acagacgtta   127380
tttgtgaagg tgactataga tgtcgatgta gcaccgtcgt tagccttcag gaatgggtag   127440
cgagcttttt tggtgatgca tccatcaacg atccctac catgacactc aaataccgta    127500
cacatgtctg acatggttgg ctggatacat ttaacgttat ttataacgta gccatcggaa   127560
tgaattctta ttgatgagtg gtctattagg ttactgtttc cagtcacagc gtcagcaacg   127620
cgatagaagt tgcaattctc tacacgcgta ttgtagctgt tgaacgctgc ctgagcttcc   127680
```

```
tggaatacca ttacgtttgc accaggagca ttcttgacgt taactccaga acagtcaca   127740 ccattactac cttcgtaaca agctactgct ggacaatgag cttgtgctcc agaccagttc   127800
aatggcggga caaggttatt gtcaccattt tcatcaatta gcatatcgtg acatatgcg   127860 ttctgaattt cacgaatacc atcaccgaaa actacaaagc ctttagtgcc cccgttttcc   127920
ttattgcgct caacaacacc atcggcaaca tacagtaacg ttgcgtcgcc atcgccgatg   127980
aaagtaacgt tgttgcgaag aaaaatcata acttcctgat tacgataaat agtcagacca   128040
tgcgccgtgc cttccacaag agtcgtttta tccaacagat aagtgccagc aggaaccatg   128100
acaacttgct gggatccgaa tagttccgca cgtttctccg catgataacc tgcgaggttt   128160
atagcatcga ccgcgtctac accgatctta tctgcgatag aatagttgtt atcagcaccc   128220
cagtttgtaa cagactgcca atcataatct gttaaatatc caacacagta aaaatcggga   128280
tagtctggaa cagttcccgg cgctactgta taaccaccac tttgtatagc accatattta   128340
acccagaaaa gaccacttga atcaacaaga gcttgctcgt tggtggttaa aactgaacct   128400
tgcaagaaag acccaaactt ctcgaattta ctattgatat aattattagc tacccactgg   128460
cgggcagtgg catcaccaac actcaaccac gctcccgaac caacgcctcc agttgttgca   128520
ggtgttgagc cagcagctac agttttagga agtgtaccat cccaacgata ctttccatca   128580
gtatgggtga gtaattcatt tttagtattg atgacagcac cagaatcaaa tgtcccagcc   128640
aaggtaacat attcttcacg agatacagct aatgcgccca gatcaacact accagcagaa   128700
tgtacaagca cagccgaaga actaaggctg actgccgtgg ttccagtcgg taactctgga   128760
ataaaatatg atctctgtgt tattttatcg tagataactt tatacccgct taacacagca   128820
ccaacactaa aataaacgac ctctgtatct ttaacattgg ttacacgagc cacttcccgc   128880
aaagtataat caatttgatt atagatgttt ggcgttccat tgataattac aacaacttca   128940
tcctctgcat ccagttcttg cgcaagagtg attttactgg ttaatggatc gaatgtgaac   129000
cccagatttt tatactggcg acttccgttt atatcaatgg ccggaacatc atcaacaacg   129060
acgtctaacg tgatttcggt ttcaccgcca atcgctgaac ccccattata gacccaagta   129120
atcgtagaag aactagaatc accgccatta cccaattgaa taggagtata ttcaatcacc   129180
tgaagttctg tgctggctgg caaagaagga ctgaaagtga ttacattccc atctagtgaa   129240
tatttggatt ccgcaagacg ttttccgtca gcatacacgt ccacgattgt tggtggagta   129300
ttgagagtga cagcacttgt ttcagacgcc aaaatttgtg taaagatttc acgactgtag   129360
acacggcctt gaccaagacc gacgccggat gtaataaccc aaccttgttc aggtccagac   129420
caagtgaacg ttgctgatac gttatcagtt gttatagcca tgtcttcagt ggagccatac   129480
aaattatttc cagaaggaga cacggtcaat gggtaagtgg caaatttccc ataagcatca   129540
caaatagtaa cggaatcccc aatacgcgta gggggaggga gaaccactgt agatgcccct   129600
gtggtattat taatgagata gccacgacct tctaacaaat tgctagaggg agcgtgaggg   129660
agcgtttccc agcgtattcc accaccccc aaagacaacc aaccaccgtt tcgtaataa   129720 ccttcaaatt catcactatc aggattgtaa cgcacagaag atggaagacc tgtaacttca   129780
gtatcttcag gaaatgtcat tacggcacca ggggaatgct caatagtgcc ggagttgttg   129840 aagccttttta tgttcgaaga ctcagaagtt tctaaaccca aagggaaaag aggctgtgtt   129900
ggtttgttgg ccatttgtaa taccctaaa tgtattcatg tcatctaggg gtatttagtt   129960
ttagaaagaa gctgcaatag aatagtcgac agaacaagcg gttgtcgtat ttgcattaac   130020
aacggaaatt ctcaatttac cacccaccac agcccctgtg aacgtcactg taccgctcgt   130080
```

```
acttttctga accaacaact ctgatttgat cgttccgtca cgagttatgg ttactcgata   130140
tgtgtcaaca acgttacccg tcccccattg cgcagttacc agtatttgac aaaggttcac   130200
caaatcaaaa tctggaagag ccgtcgttcc agaagccgaa accgtgtatg acgacaagtt   130260 tgttttgtg cgataaactg cgttccctaa actgttatca attgtggtca ttttggcatt    130320
atacgttgat acatcgacct taccagtcgt gagagaactg atactgccgt ccaaggaagt   130380
catcttcgta ttatatgtgc tgacctcgac tttattaccc agagacgtgt tgatattgga   130440
gatactcaaa tccaacgacg ccatcttagt gttgtaagtc gaggtgttga cttttccgtt   130500
caacgacgtg ttgatgttat taatctggga ctctagactc agcatatctg cgtcatatgc   130560
tgtcgttgtc acatatccat taaatcggtt atctgcaaac aacgcatcaa aaaatgcagt   130620
cattgtccaa taacgcgctc cagaatctgt ttgtactgga actgaagtcg gcaacgttgg   130680
tccggtatac gcagacaatc tggtaaaatc caaattgaat ttgtaatatc cggatgtcaa   130740
caactcccca gccaaaccag aaccaggtgg ggtagtgtct tcactgacac catgctttct   130800
caacatgctc aggttaacac catctgtcga gttcgttggt tcatctgtga ttgaaacgga   130860
ttttccggcg ggaacttgta tgcccccatt ggtcaccaac aacgcattga aagtcttttt   130920
gccattgatt gttgttcac cactatctgt ccgaataact ttgttggcca gagtatcatt     130980
gattgtgtca acagatcttt tcaactcata tgtcaggcga gcagatggtg gaaacaatgg   131040
gtcgttaact tcaaaatcgt taataacgtc attttactt actttgtcat caacagaacc    131100
caatatctga tctatctgct gacctgtata ttgactcagg aaatcggcca tttttagctc   131160
cttgtgcttt ctaggaatac agtaaatcca gcaggatgga aatgctgacg gaagacgcgc   131220
tcaaacacac cttcaaaatc agatacgtcg cctgggactc ctataacata agtgtattca   131280
tcataatagt aatcatcacg catccctgtc gtgccgtcac attcaaaatt tccgtccaga   131340
ccgcctatgt cttctttcgt aaaatagacg ctgactggac aaccgaaata tatccaaaag   131400
aacaattcaa ttgctttctt tgttccacgt attttataga tgtgtttcaa caatttcagc   131460
caacgcggat gatccagagt tcttcgttta gttccttcga tataaacaga gaacgtatcg   131520
cccgtggttg tcaacaaaga atccgaacca actgggataa aatgaccaaa ttcctgaaat   131580
gatttatcaa cggttcgttg gaaaccaaaa tcattatacc agtcatctat ctgtttgttc   131640
ttatcttcta ttgacagtag cggccttccg tcggcatcta aaagttcttc ggcatccaga   131700
gccatcatgt tctcaaaggt acgaaccaag aatttatcag acaaataatc cttggcctct   131760
gagcctggag tcttgtcagc cttaaatca atcagctgtt taaccggaga atcttcactc     131820
tcaggattca tccaactaga cgtatctgcc agatatgcca agatctcttc ttgagtgaac   131880
ccctgctgtc tatacaacca attgaagaac gtgtccataa attctatgaa cagagggaaa   131940
tcattctggt agaacaacgg agtttcatac ttaaccccgt tgtgtccatt attaagatct   132000
ttggacatag cgcacctctg gcgtaacaac cacatccacca atcttgaata cttggttttg   132060
tgtagcctgt atgttctggt tcagtccatc cggtaacacg actatggtca ccccttcagg   132120
gttatagttg gagaccgtga tctgctgaag gtccacaacc ccatttgcat aatccacaac   132180
ccctgttttt tgaactaaaa actcttttgt cgtgtcattg ttattcactt tatacatgtt   132240
cagatcgcca ttatcgtcgc gcatgtagta agtgaaatcc acctcggcag gaagcggttt   132300 gaacccccgtt attttcacag aaccaggttt gatacttcgt ccataactga atgtgaaact   132360
gtctaagact ccataatcag gtttaaaatg gcgtttataa ccaactgaag taatattcga   132420
```

```
gttgatagaa cgttccattt ttgtaattgc ttcctgcaat atttctttgt caaacaattg   132480
atcaaatccg ccgagattat tttcacccca tttaacgata ctgtttccaa caacaacttt   132540
catctgttct tcaacgtaga ctgtagaagt aggatcccaa aatatagtcg ttgagacttg   132600
gatatatgtg atctcggaat ctaccacttt ggggtgata  gatcccacat tatacttgtc   132660
cagagcagca acgatatcgg ccttctcagc gtccgaaagt gtctcaccaa cagaaggtat   132720
aacagcgatg taaacatagc cagaatcagg aggagacagc gtgtcaccac catatgattt   132780
agctcgggag acgttggaga ataaccttc  agtcaataca ccataatctg tttctgtaac   132840
cgcagcacca tcagcctgat aagctaaagg agccaaccgt ttagtgtcct caatagattc   132900
cggatcgtct ccacctgcgc tacgttcgga aaccaattct acgtcgacct ggttaaaccc   132960
gcctatggat gacgctgatg acaggcttgt aatatcattc ccatcagcac cagaagtttc   133020
taagtattga aggaatatga cgttcccatc ttctactcga cgcgaaagat aaccatctcc   133080
gaattcaaac acatcagac  catcaatacc caattctacg aaatacaggt aggcatattg   133140
gctcagatca aatggactgt tgtaacgttg atatgtcgtc gaaacgtcgg aagactctga   133200
ttcttgtact tgcacgacca tatgattgat atcgacattc ccagaaggaa tcgtatatgt   133260
tgaaatcgcg cttccttcaa catcatatgt cttgtacaac caattcccct gtaccaactt   133320
tacattgttg aacatgtaat aaccgtctgc agtcaacgtt gccgacactg gtttctcaac   133380
agtaaagttg taggaactgc cgtcttttgc cccaacgaac attacgcgcc gatccatgat   133440
gatctcattg ggggctgtgc tggcgtcata aggcgtaact ttgatgttga catacatgta   133500
tgctgcccga tagttgtcag gcgtgtagga aagaaatgca gcagataaac cgacgtttga   133560
acgttgattt gctgtcttca aatggccttc accattaagc atgttttgca taaaggctat   133620
ggcgttcgcg tcagatgcca acaaacgaat aatcgcacta agaccagaac cttcaaagtc   133680
ataatcttta aaggtgggat cagctttcat tcgctgttta ataatgtatt caaatgctct   133740
gacgtcgagt gaaggaactg tttgcgtggc catgataatc tccatcacct gagtttgaat   133800
atggtgttga agatatttag ccaacgggaa tcaaaacgct cgcgcgcgtt taatttattc   133860
gaatatactc gcgaggggg  tgacgccctc gctcgtaaca ccgccttgac aggcagtccc   133920
attccacagc catggaggct gcttctcgtt gttcgttaac actcacaact cgaagggcac   133980
cgcgttaaga tacagtttct tgatgttgta gaaaagtagt ttttacctat taataaatca   134040
cgctcctatt ttgttggcct ttaattcaat aacacttgta cgaatataat agtctggaca   134100
aacaaccgtt atcaaggaac ctctcatgca tatcaacact gctgtattaa acatatcat   134160 ccctttgtta gaaaaatatg aagggaaagt aatgtctgaa gtgccatttg agaaaattcg   134220
caccgaaata aagcgtctga caaataaga tgtcaattac cgtcgtgtcc tttcttctgg   134280
ggtagaactt gcaaagtctg acttcaaaac atcttcgaca ttctctttta atatcgatgc   134340
cactgcgaca ctaatgggtg aattaatgca gtcaacacaa tctcgccgtg accgctttcg   134400
tcatttatgt gttgctaatg atttaccgat cacccgcgtt ggaatcaaat tggaggcaat   134460
ccgttctgac acttgcttca cgataaatta tattgtcgag ccaggctctc aacacattta   134520

ttttgccgcc gtgatcggtt tctacggcac ctccatcaat gggtgggctg agcgcgttga   134580
attaaaagag acactgaaca aacacagcac tccttccact cattatatgt cacaggccgc   134640
cgcccgtgaa tatgtgtatc tgattgagcg cgatgtgaag ttaaagtgg taaaataacg   134700 ctttattcaa taaataattg tagtaaagtt agttgcatgg aagggaggga acactatgtt   134760
ttacatgatg ttactcctca tcctcctgat cgggattacc tgctctctcc tgggtctacc   134820
```

```
cgatcagtcc ggtaaacagt tgcccacttc ggcgcatccg gttttgagtg aaggttcgtc    134880
cgcactgctg tgggcagtgt agctcaaagg ggagaggact tttcaaatta gctgggctgc    134940
ggtaaagtat taaacatgag ggaaataaca cagtgggagt cgggtttgca gcccaaaacc    135000
agttaacccc tagtctcagg ggcttgtgtg aatagaggcg taatagccac ctcgctggtg    135060
tcagtggacg cacttgaccg tcggagaacg aaactccctg ttgtagcgtg attagctcag    135120
aaaaacgaga gcaccccgtt ggcaagtcga caccaacata taaggggagg tcggggcgc    135180 taatctccat cacgccgaca acattatgag tcttcataga gggttcataa tgttgcgtca    135240
aagggcaaca agaggattcc tgttggttga attaacttga ttcatagttc ctgctgatct    135300
tcccggattc agaagaacac cgacaggacg aggccgatg cgtaagttcc ggcaaatcga    135360
tggtgaggtg gtgcattgat gacacggggt agcgctcaga agtgtggttc gattccgcac    135420
cctcgccaac aaaaataaaa ggttttatca ataacgggtt acaaagtata gttaactcac    135480
tgaacggcaa gctgtttgag tcctggccac tcatagcgat gtgagaccaa gacaggtagg    135540
tttaggactc aaacaggttt tcgttttcgt tgtgcgtgac tttgcgggtt tttagaaact    135600
gaccacaaaa ataatcgcta atgataacac gttcctggca gtagcttaat agccatacac    135660
cagtgaggtc ttccgattcc tcatcaccaa attcggcgca ctaaaataga cgggagggtg    135720
tgattaataa tctcccgtcg acaatgagcg gagcgtgtac ttaataggtc gatgggagca    135780
gactacttct gagaaatcag gagcgtacat gagaaggttc gagtccttcc tccaatccca    135840
acgccgttat atctgactgt ccaaagggga taagctcctg agtaggcaga ggtgggttgc    135900
ctaagtcaga tgggatgtaa ggtcagcgct ggccaagcat ttgggttcga ctccctaaaa    135960
cggctccata tctttgaggg cattccgcgt cagacgcgag actgtatgga gtttcaggag    136020
aaaggcaact taaatccgag gcagtaatgc cctatgaaat atcggagcct gttgtacact    136080
gagtgccctc aaagatgtgt ctcacagcgc atcagtttgc agttatgcaa gcttcaataa    136140
gttaaaacgc gcctcgggcg ttatgggata aagccttaaa cagtggaatc cccagggcta    136200
gcaatccctg ttaaagaagt agccgtgtgg ggggttttgcc cccacaacgc aaatcgaagt    136260
tctctgggta tatcttttaa ccctcaaggt ctgtacacag aagtggccgt cccatgagta    136320
agttaggcga tatacaacat gttgggtcga acctgttaag cccagagaac ttcgatttgc    136380
gtacttgaga gagcgttgta tgaaataggg caatgccttg cagacctcga cgcctacaca    136440
ttctagacac tggtgggcgc tggcgaagat ctcaatataa gctggtcatc aagggtagct    136500
ccctgaccgg acgaacaatg agaggccgaa ctaaggggaa acccgagaca ggcgcagtat    136560
tctcgagttc gcaaaacagt gatcatctga caagtgtgat cactcttcga tagagacatt    136620
acatcgtggc catcaaccac atccttgctc tagtgttgag tggtgttttg tttcttcggc    136680
cagcctcgtt tggtccgagc gatagaggac aagtattcgg tgtgacgaag acattgaatg    136740
cgagttgtaa catttggttg caactttgat ggctctggat tttataaacc atgtctatgg    136800
gtgacgcggg atctttagta ccagagccat caaagttgtg tccaacccga tcttgcaagc    136860
ccgtatccct gtatggtcaa gacttgcaag tggaaagccc tggaaaaata aacgcctgtg    136920
gtgaggctac ggtgcaagcc aaagaccac agaagcgcgt tgccgcgagg cgcacaaaca    136980
ggcatgcatg aactgatcat gcacaaacgg gataaagggt tgagagacct tggttggtca    137040
cacaataaat tatggggcga tagtttaagg gattcgatgc gcgcgcatcg aatcctcata    137100
gagaacagct ggaggccaat ccagcaggtg aggtgaaaat cctcagaccc cgccaaattt    137160
```

```
tggccccgta gctcagtggt tagagcagtc gactcataat cgattggtcg ctggttcaag   137220
tccagccagg gtcaccacta aataaaccag ttgttcaata aacaattggt gagtatgatg   137280
aaaacgttcg gtgagtttct tactgagtgg gatggcctcg ctactgacaa caaagagatt   137340
gttgagtttg ttgaaaagcg aggcgataag tgggttgtcc ttgaccacac caagactaaa   137400
gttcttggga cacatgacac caaagctgac gcggacgccc aattaagggc gatcgaagcg   137460
aataaacata gttgaagggt tctatattat gaagaatatt tgggtggtga tttccaacag   137520
aattcgcgct agttgggaag gtcggatggt gagcatcaag aacgggtctc atccaaaaac   137580
ttacgatcgt tatgatcctg ccctgggtct tcatgcaaaa taagaatgt ttacgaaagt    137640 aagaataaat gacgatgtag ttcagtcggt agaacggcgg tctgttaaac cgtatgtcgc   137700
aggttcaagt cctgccatcg tcgccaggat tatgtcgggt cttgcaggat ggaatagaga   137760
ttctgttttg atgtccaggg gagtctagta ttcaaagtga acatatgata gctttgaaga   137820
aacacaaact aaagattggg gtttgaatcc cccgcccgac gacaaacaat gggtgtgaaa   137880
cgaaagcaag taagcacgaa gtacgcgaac gacaagttct ctcgagcgac gtccaatagc   137940
cgaacggaat ccgaacccga cgaaagtaac gcccaccaaa ttcagagtgt agaggctaca   138000
gtagtgcgca cctcacggaa agctacaccg gacactctga tacaaaatct accaccgcgt   138060
ggattagctg aggaaggatg gccgatgtcc tcaagcgtgg cccagcacgt ggtggtagac   138120
caaacacagt aagcgttgca gccagctgtg tataaaatgg ggtgactcca catcggaaac   138180
gatgccccaa cttccagaaa tggtcgggca cgaagcctgt aaagttccag gagatcgaac   138240
cagaaggcac tggtgccagt taaccaatcg gcgctgataa gcgcggggag ttgggctacg   138300
gcagatcaaa tgcacaatcg ggtgtgaagc ccgtcctaat ttcgcgggag ccatagggggt  138360 tggccagtag ctgactgctc tcccgctcca aattggaagg ttgcccgaga ggtttaaggg   138420
actcgactgc taatcgagtg gggcttttag cccccgaagg ttcgaatcct tcaccttccg   138480
ccaaattgct tcatagctcg agtggtagag cgcaggaaag tttcgagaga caaggtgcc   138540 tgaggtcact ggttcgaatc cagttgaagc aatcagaata atgagtgtga cttcctgaag   138600
atgaagaagg tgtgcatgcc gacttcataa caatctgggg ttaaggaagt taagaaagtc   138660
gcaggatatg caagtgaaat gcaaatagct ttcaacgtcc tgacgatttc gggttcgatt   138720
cccgacgcac tctcccaaac gcctaatact agaaattgct gtgagtagtc tttccatccc   138780
cacgatggtt taaccatagc ccgatcagga agatcgggct tcttttttgtc tataataaat   138840 agatctgact tgtaaaggag gtctgttatg gcaaccgcta agatcatacc aaacgcaagt   138900
acatggacac aagtctcaga cggaacatct ttgaaaactc ttcaagtgac tcacggttct   138960
gtgtatctgt gtgatagccc cagcgctcca acgggtaaca acgcgcatat catatatcaa   139020
ggaaatatgg tcgttttaac cccgccgacg gtgggttggg ttaaggcaat taattctgat   139080
gcgacagtta tcgtttctta aggggagat atggctattt tgacatctcc ctatttgggg    139140
aatatgcttc agacccaccg cattaaaaca gaagtcagat tttctggatt gtcacaactg   139200
ctaacttctg gggcaactgg aatagattta ttaactgtgt tggatgggaa gactccgaac   139260
ccttcttctc ctactggttt agcccgcttt tttaaattat cagatcacaa atttcatgcg   139320
tttccctatg attctattct tccggtgaag gttaatattg tcggatcatg gtctgggtct   139380
acttctaata gaactatgat attagatttt gtgggttctg tggggaacca gttatcaaga   139440
agtcgtgatg ctagcgtacc gccgccggac actttgtctt tcattacatt cttcagcgtt   139500
gacaaggatg ggaacctggc gaccaacgga gcgcaaatga aactgtactc ttatggtggt   139560
```

```
gactttacca ttaccgaggt cgtgttgatc gctgagcagg ttgtcccact ctatatgact 139620
agtatttgat ttgttcaatg agaataaggg gtttaaaatt taaccgttta taaaccccctt 139680 cattgatttg aggaaacaac atgcgtaatg ttacgatttg ggattacaac gatgtcgttt 139740
gtgacctgcc tccatttgct cgcctgtaca catacaaagg gaacaaacgt actcttaatg 139800
agttcttgta tccggcatat atctatcggg acgggcatct tgctccgcga tcacttgaag 139860
aaactggtgt gtgtactcct tttgatatca acaagaaagg gcaagcggta ttcattggtt 139920
attccagcga agacgacatg gtaaatggtc gacgcggtct gtatatggtg ttcaacacat 139980
ttgagcaagc cgtgaattgg ttattcaaaa atggttatga tttctatggt gaagagagtt 140040
ctactgctcg ccgccgtaaa gtaaagaatg ttgatttcta cacagagcgc aagaaatatc 140100
tggacatcgc tcatcagtat gagcagtcta agaaatccgt tctgatcaaa ccatgcgtta 140160
cggtcggtga agaagtgggt gtcgtggata attccgattt gaatcaggca attaaatctt 140220
tgaagccaac tcctctggcc agtggtgctc cggttgttaa acatgacagt tcaatcccga 140280
caccgcctac tcctccggcc agtcgtgttc tgaatgatca gggcgctccg gtaaaacaaa 140340
aggtcgagaa gccgactttc atggataaca tgatgaagtt ccttcgtctg ttcaagaagt 140400
aatccgagat tctccttttc tatactcctg tagatacgct atgataagcc aatgcctaca 140460
ggagaaatag aatgaacaaa accatcttcg atacccttc cctcgaccgt aatctggttc 140520
actgggaaga ctatctctac aaacacaccc cgtgcgaact tattgccaat ccagaaacca 140580
atcagcaggt ttggttcaaa cgtgaagatt acttcgcgcc tttgtcatgc tatatgaatg 140640
gcaagcaggg gatcaatggc agcaaactcc gccaggccat ctggctcatg atggagcatc 140700
tgaaagctgg aggatcccca gatcttatcc atggtactgt agttggtagt ccgcagtccc 140760
ctatggcgac ggcagtctca cggcatttcg gcggcaagac aaccactgtg ctgggtgcca 140820
ctaaaccaac cacatgcatg aatcatgata tggtttcaat gtcagcatgg tttggtagtg 140880
agttcaactt tgttggatct ggttacaata gcaccattca gccgcgctgt aagaaactca 140940
ttgaacaatt aaatccaaag gcgtattatc tggaatatgg cattacattg gatcataccg 141000
ttcattcacc agaacgcatt gctggattcc atatgctggg tggcgagcag gttgccaata 141060
tcccagacca tatcactgat ctgatcattc ctgctggttc ttgtaattca tgcaccagta 141120
tcctgacagg tttagcgatg catccgaaac caaatctgaa gaatgtctat ctgatcggga 141180
ttggacctaa ccgattagat ttcattgaaa gtcgtttgcg cattatcggt aagcaagcaa 141240
acctccctca cataactgat ttcactcgtc gctatcacga caacccagat tatgtgtatg 141300
gtaagaagga tcttcagcat gcctctaaga gcgtttcgct ggctggcctc ctaagtggta 141360
tcaggccaaa gaacgagccg gatatcgtgc ttcctcgctt tgaggtacac cattgggatc 141420
ttcataccac taattgggtt cgttacaacg acctcatgga ttaccagtgg ggagatattg 141480
agttgcatcc tcgttatgaa gggaaggtga tgacatggat acaggaacac aaaccagaat 141540
tgcttaatga gaactcattg ttttggatcg tgggtagcaa gccatatctg gaagcgatga 141600
aagctgcttg tcctgaatta tcaataccctg aacatgtccc tgtgaatgag tttgtcccca 141660
gctaatccat cctaaatacc ccatacgacc agtgtggggt atctatgaaa acctttctag 141720
aattttatcg cgaatcaacg ttacctgatt ttacgaatat cgttttgtat catgggtcta 141780
atgttgaatt cgatatcttt gattttgaaa aatttggcca gactgactct ggtacgatgg 141840
gtgctgggtt ttacctgacg ggggatccag aaaaggcaca gatctacgca gaaaatgccg 141900
```

```
tgcgctatcg tcaatctggt gaacctattg tcatggcatt tcgtgtcaag gccaagaaga  141960
ctcttgtaat agattccaca atgtttcggt gtgggaaaat aaatgcgaga gttggggata  142020
aagcctggta aatacatgat aatgtgaaag aacttatcaa caaagggttc gattctaata  142080
gctctatgag tgccataacg ttgaggaaat gggtggtgtt aagccaaggt tgggcgacca  142140
aaaagcctaa tagttccaag cggttttatt caaaaagaat ttaccttgcc aatttcgaaa  142200
ttattggaag cggattcccc cagcagacat gcttatctgg actgtggttc aagacgggac  142260
tacgattgaa ttctttgagc gcggggaaac aggcgctgaa gagatttatg cttccgtgca  142320
agggacagac gtcgtccgcg ccgccgtagc tcttgctaca ttttagagg acgccccga   142380 ttgacggtat cccgtttgaa gcccatgtgg acccagaaga cccgacgtct atcatcatta  142440
cagtccaggg tgctgaatat acatcttaca gtattgagca cgatgaagaa acaggggcgc  142500
tgtttatagc cacggatctt caattggaag atgacgaaat tgaatatctg aaacagaatg  142560
gtcgtcttcc agagtactct gacgaagaat tggattctgc gtttgatgaa gtagacgatg  142620
aagacgactt ttgggatggg aaataaacaa aggggcttaa tgccccttg ttttagatat   142680 cgtttgtgtg tactgtgaat ctcattgtta cgacatctgt tctttcatcc ttgtgtaatt  142740
cgaacttcaa accttcctt agaagactcg ccaccaacaa tgttttgaac ttttcgactt   142800
gcttgtctgt tgggtatttt tgagacttat atgcctgttg aaatgcggtt aatatttcgt  142860
caaacctgtg gccaccaaca gcgtacacca tgtcatcaat ttcaactccg cgatttgctt  142920
gggaaacgag ttgcttcttc attttgcaaa caaagatatc aacggctttt tcaactatcc  142980
ccatggcttc ccaaatctga gcctggtcaa tcgtagtctg taattcttgt gcgaagtttt  143040
tcatcatttc accttcctcg ttggatattg gttaaagagt ttgcccagct tggacacatt  143100
gataatcgtc tgagtcttcc agcgctcgat cccctctggt gtagtcacgg ttaggattga  143160 ataccccat atatgggaac cattcagcac agccgcgctg tgcccaccaa ttttgtcttc   143220
cagtttacaa atgaaagact catattgcat cgcagcgttt cgacgtgctt ctttgacaaa  143280
cagagcatgg cgctcaggat cagctttgac aatatccggc ttcccaggta tgtaagaagg  143340
attcactgcc tgggtcaaag aacggtagag cgcatgtttt gatttcattc gttggtaatc  143400
tggatcacca aacttgacac caaccgaaga tggccacgga gcgcacttct cgacgtccca  143460
gccgttggat gccagatcgt ccattatgtt cttgatgact tgttcgcgt  actgctcagc   143520 agcattctca gcatcaacca gcagaggctc gacggcaata cggacaggag ttttggtat   143580 attcatgata tagtccttca ttcagacaga agacgggcgc ggacataacc caggatgtac  143640
gaaaccatac cgtacagcag gacagtcagg tcactgggga ttaggtgata cttgccgatg  143700
tcggccatgg ccagaaatgc gaatactacc cacacgataa aaatcataat atagtccttc  143760
agttcaaagt aagccccga aggggctttg tcatattaga ggcgggaatc caaccatgcg   143820 ttctttcat tctgccattc ccaagcggcc tgaccaccag ccatgataac ttccagagaa   143880
ggagtattgt catcctcgcc gccgtgaaga tctggatcaa atccatcatc ttccggatca  143940
tcttcacatt cgttctgata tgcggaatat tcaatataat gcgcttcggc ttcgtaatcc  144000
atgtctccca gagcagtctc aagagtcatt ttaccttcgg caatcagctc agccgttgcg  144060
tcgtccagac ctgcgtcttt cgcttcaacg aacagttcgt gacgtttctg gaagaaaaag  144120
aattgcatgg cggcagaacg tgaatcaaag aattcttgac gaggagcagt gatatcacgc  144180
ccatcaattt tacttaccat cacgacacga gaaccgtact caaccaggaa gcgaccgcct  144240
tttacggggt tgctgccgtc aactgtgccc aaagtggtga ttacacggcc ttcttcggtg  144300
```

```
ccgaacaata cagttttgcc ggatttggat tgagcgataa tttcgattgc catgatgtat  144360
ttccttctct tcagattgtt gtttgttcgt actacaatta gaagtatacg ccagttattg  144420
aagaagtaaa ctttattcaa taaatatttt aataaatttt gaactctgct cctttgtaca  144480
ctgctgtccc tcgttctatg aggccgtcgg ggacaaccac ctttgtgggc catccgccgt  144540
ccggtgcttt gacagtcagg cgtgtcttat gatcacccag ctgaatctgt tcgtaaatcc  144600
ttcctctcac tatcgtcgcc ccgccttggg tgacgagcaa tctcttgttt accactttca  144660
ttccttaaca ccaaaagaaa ggggagtttc ctcccctcta acttatttct tcagatcagg  144720
ccacgcacca gaggtcgcag tagacccagc tgggggagca gactcaagat cgggagaacc  144780
cgactgagta acaacagtgg gatctttgtt aaccactttg accccaaact gcttgagagc  144840
atccacagct gcgccttcc ggctgttgct tttgtaatgg ttatacccct tgataccgaa  144900
tgatgcacta attgctgtca ataacgaata ggtataccat tcaggtgcgg tatcgagcgc  144960
ctggaggccg tcgattactg ctttgatgaa atccccttta tgatactcat cagggaacag  145020
aattagttcc acaaccggag cagtcatgac gaggatagcg ggaacagcta acacgatagt  145080
ccagaattcg tctttccaag acccgccgac ttcggtgatc ttagacagct cccaatctga  145140
ggaggacttg atagcctcta gcttgacatc gtgtttggcc tgaacaactt cccgcttgta  145200
ttggatcaaa tcagtcccga ggttccagag ttgcttgagc gccctggga tcatactcac  145260 aaggggatt gccataataa actccttggt cattgaacgt tcctcggcta aattacgggg  145320
acgtgctaac ggcacggtta accggagaca aacaatgact gttttctata cgaacgttgc  145380
ccgacagggt aacgaccttc tgattcgtat tgcagacgac aacggcaatc gccgtatgtt  145440
gcgtaagaaa ttcgaaccca ccttgtattt acccacagcc gattattcca aagttgaaaa  145500
gattggcctc ctcaatgaac cgttggtgtc taaaaaattt gcgtcaatgc gtgacgccga  145560
caactatctg gaggaatata aggaagtcga aggcgctgcc gtttacggac aaacggatta  145620
tgcatatcaa ttcatagcgc aaaatttttc tgggatgatt accccgatt actcaaatat  145680 tcacatcgcc aacgtggata tcgaagtttt ctcggctggg tggcgcgatg gagaaatgac  145740
taaaggccca tttcctcacg cgacgattga atcccacacg tttaagggga gcgaggcgcg  145800
tgttcgccga ttccataagc aagtgttggc caaccatgat ttcgttcgag agcacttccc  145860
aggttccttt atttccaaca acgtgactga ccagttccct atcattgata gtaatggtaa  145920
gatcacacag aacatgaatg ccgccttccc tattacgctc atccagcttc aagacatgaa  145980
caccaacaag ttctatgtct ggggtatgcc gtgttctaag gatcgccata aattcaaata  146040
tgatccaaat gatgaagaga taggtggtct tgaggttgaa tacaaagaat acacgactga  146100
acaagaactt cttcgcgctt tcttagatta ttggtctgaa cgtcaatttg atggttggac  146160
tggctggaac atcgaaacgt ttgatagccc gtacttggtt gaacgtatta cgcaggttct  146220
cggtgaaact caggcagagc gcctcagtcc ttggggcaaa ctcaagaaac gtttcatcaa  146280
agaccgtaaa ggcgacgtga cttcttatca attcgtgggt tgtcctatga tggactacat  146340
gcaagtttac aagaaacaca cgtacacaac ccgcgaaaaa tactcactgg attggatcgc  146400
ttattgtgaa ctcggtgaga agaagttgga ttatagtgaa agcaagtcat tgtatgatct  146460
atattttaat gattattgca aacacacccg atatggtatc aaagacgtca aactcgtgtg  146520
gcgtttagaa caaagctgc gtttgataca gctgatgttc gtattggcgt atcgcaccaa  146580
atctaactat gaagacggtc ttgggactgt agcaccatgg ctggcgatgt gttactatcg  146640
```

```
tctttatgaa aagggggattg tccctaaaat acagcgtgta tatgatggtc caacggactt   146700
tgaaggcgca tatgtcatgg aggttgcacc agggatatat ttctgggtat tctctgagga   146760
cttaaactcc ctgtatcccc acatcataca gcaatacaac cttggtcctg agactatcgt   146820
ttctgacaag cacacacgtc gcgatatcat tgagtccatg tgtgaagaat tgaccaaagc   146880
gatgaatgat atgacaacgc ctatgaacaa gcgccgtcat ctcaaaaatc ttcacgacaa   146940
gctgcagcgt gctattgatg aacgcataca agttgttgat gaattggtcg cgctgggtga   147000
attccatttt gaaacattac gtcgatataa cgtttcgttt accccgaacg ttcaattctt   147060
cagtaatgag aagatgtctt tccttttccga aattatgcga ggcatatacg ctgaccgtaa   147120
aggagagaaa gcaactggtc tgaagtatga gcaatgggct ggttggtgta aggaaatgtc   147180
taaaggtgat ttccaccttg aatctgccat gaagtctcgt ttctacgatc ctgaatggta   147240
tgaagaacac aagcatatcg accttgatca cctgactgaa gtcatgcaca gtgggaaga   147300
tttgggagtt gcccaagata cgttacaaca aggtctgaag atcttgatga acgcaggata   147360
tggtgcaatt tctaacgtct ggtttaaaga atacttcaac atcaacatcg ctgaagcaat   147420
taccacttcc ggcccagttg atcaataaat ggaacaaacg ccacacttga tgattatctg   147480
aacaaacttt gtggtactac tggtcaggat tttgttatcg caggtgatac agactccaac   147540
tacatttgca ttgaacgcct ggtcaagcaa ttgtggcctg aagaaaagga ccatcacaaa   147600
ctcgttgata acattgacca atggatcaaa gagaattacc agccaaaaac cagtgaatgg   147660
gcgcagttgt tgtgtaatac catgaacggg tttgagcagc gcatggtctg ggaacgtgag   147720
gtcatcgcat cgtctgctgt atggcgagcc aagaagatgt attgcatggc agtatacgat   147780
agcgaaggca tcaagtatga gaagccaaag atcaaattca aggtctggga agcgcgtaaa   147840
tcaaccactc ctgagtggtg tcgtgagcgt ctggttaaat gttatgagaa agtcctgctc   147900
ggtactgagg cagaggttca ggaattaatc gctggataca aaaggaata tatggaactc   147960
accgtggatg atatcgctca ggcatctggt gtaagcgata ttgagaagtg gttagacgcg   148020
aacgggaatt acatcagcgg tacgcacttt gctgccaagg cttgtattat gtacaacaag   148080
ctgatcgata agcacgaaga tctcggtctt cccctatcg aatctggcga taaggttaaa   148140
atcatcaacc tgaaacctgg caatcctgtg gggaatgatc gcatagcctt ccctgacttc   148200
cttcctccag aattgggatt ggataaatgg gtggattacc acaccacgtt tgaaaagacc   148260
tttatagagc caattcagtc tatcttggat gtggttggtt ggtctcataa acgtcgagtt   148320
aatctgttgt ccatgatggg caagaaaggt tgattcaata aaccaaaggg ggatataatt   148380
ccccctgtta tcccttttgac aacaggtatt gttatgaaac tcaataagat tcttctggtg   148440
tgtgctctgg ctttctctac cactgcatgc tctacccttc tggacgttgc gtctactgtt   148500
gacctcgatg cgccgacgtt caccaatcag caagcggtga ataagatgga agacacaatc   148560
aaggcacatg ctgcgttgga taacaccact cctggtccgt tgcaaactgt ttgcaattat   148620
gacgattcca tccaggaaga tgaaacctat cactgtacca cttacgtgaa ggaatcttct   148680
gtggttctgt atgcagattg cacagaagag caatgcaccg caactggtta tgatcaagtg   148740
gagaagtctg atgaataatc atgttggtct gtatgatgcc aattctaaaa tcggtggaat   148800
gtatcgtatc ctggtagacg tagacttgac tttggttgat agcctctccc cttgggtgga   148860
ttggtttaat atttccaatt caaaagctgc tgctgaaaac atgggttgtc atgattatcc   148920
caatgatttc cagcgtatca ccaaagagtg ctatatggct catgctggtg atttggcgat   148980
cctcatgcgg gaacgcgctc acccagcatg gttgacgcgc cgtgtgtttg ttgctggtca   149040
```

```
atggatggat tcacctacag gacgtgatcc tatggattgg tggcgcatgc cggacctgta 149100
tgccaagatg aacccgcttc caggcgctta cgagttcctg gtgaatctga agaagatcct 149160
tctcgaagac tttgaaaatg ttgaattgat cgcagtatct aagtgtgagc cagaacacga 149220
gcgcagcaag cgccagtttg tctatgacaa gttccctggc atcttcaacg ggtttgtcag 149280
caccgacgaa aagcatcttt tggcaggtga tgttttaatt gatgataacc cgaaatacgt 149340
tgaaccctgt gcgatgaaca atattttgt catctttgtt ccccagggaa attatgaaaa 149400
actggatctt tcgaactcgg aagatatgct ttatattaaa ccagtcgaag gccagaacca 149460
cttcgacttc ctgaaccgca atattgtcga agtggtgaac cgcctgattg gccattatca 149520
atacgtccat tgaggaggac atcgtgcaag aacaatccaa gtttggggaa accccagaca 149580
agcgttccgg tgatagcgat atggatggcg ttattatcca tgtgaacaac ttcattcgta 149640
aacaaaccac acccacttcc gttggtgcgg cgctggagtt aaagcgtgtt ctgatagaaa 149700
acggtatggc accagatgac gatgaaattt tctataactt cgacgaccag tataaagtga 149760
agtttgtaga aaacgatcgc ccacaggttg ctgttttctg gtctccctgg ttgggcggtg 149820
tgagctggcg tattgaggaa gatgcataat ggctaaaata attgtagtga aggaacaag 149880
tggcgtgggc aagggtacga gagtagtcca gttcatcgaa tggctccgca ctaagctgga 149940
gcctactgaa ctcacctaca ccattggtga caagacgcgc ccattcggcc tgaaattcga 150000
agagctgaag ttaatcttcg tcggccagta tactgtgtcc aacaaatccg gtctggcttc 150060
ctggacttcc atggacgcca tccacgccgc cacaggctcg ggtgatatcg cccgtgatct 150120
ggtcaaaggc tggctggctc agggttacac tttggtgtgc gagggtgaac ccctcatgct 150180
gtcagataaa tggcgtcctg aatggatgtt caagaactat ccgattgaat ctctggcgtt 150240
gctttatttt gcatacccag accgctatca gtatgatgcg cgcatccgtg tcgctctgg 150300
taaggaagca ggggactccg gctggtcacg caacgaatct tactccaagg agtttgaaga 150360
gtcgaagact gaaatgctgg tgctgggttg ggaagtggtg gtcaatgact acagcgggca 150420
agacgtgttg tatcgtcaat cgcctacaaa cactcaagaa ttcaaaacag gaaatgatag 150480
cgaattagcc atgatgccgt tgatgcacc tttgtgggtg attggcaacg ctattcatca 150540
tcaaatgcgt ggtgagtttc acgccatggg tctggacatc aaagatttct acggattctg 150600
tgaaactgac ccaatgacgc gcgaagtcgg tggggatgat cctctagcgc atcgagtccc 150660
tgagaaggtg accaaatcta aaaccaaggc gagcgccaag ggagaggtaa caaagtcctc 150720
tgtatccctt ctcggcctgt tgagtaaggg ttagaaatga aacagatgtc taaatatttt 150780
gtgttcgtcg gattggtgat gtgtatcaca gctgtgctcg tcggtgtcat gaaatatttg 150840
ggcatcgttg agttggattc aaccgaaata ttgaacgttt acgcgttata ttatttgggg 150900
ggtgctatct tattaacgcc tttcgtctat aacataattc agagtttcaa aaggaattaa 150960
aatgaaaatc ctcattccac gcaacgttgt cgctgttgct attgattacc gtggtgatgc 151020
gaagatgatt aacgctgtcc gttactatcc ggaacagaat aaaatcgtcc cacaatttca 151080
actgaatacc aatccttctt ctaaggattt cggttcttgg cgtcaggtgg gtttggctcg 151140
tacccaagtc aatgcccagc atttatttc cgaaaagacg aaaaccgcca agcaaatttg 151200
gttggtgacg aatgatcgtc gtttcctgcc tatctggtct ctgggacagc ccgtagtaag 151260
ccccgaagaa attcagctgg ctcccgaagc tgagcctgaa gttgtttctc ctgtagagga 151320
agtgaaagat gaaaatcaag caggttgatt ttatcttcat gatgttgatg ttcgttatct 151380
```

```
ttacggtttc gctggtcggc gtcatggtca cagaaggggt gcaacagcgc ccattcttgg   151440
tgatatgtcc tgtatctatc gccactttct tctatctggc gttccgtgtt gaactcggga   151500
gtaaaatcgg atgaataaca tttctaaaat gccgactggc tatgcgcccc cggctgaatg   151560
gaagtacccg attgacctgg ctgttgacta tcgcaagcct gagaatcgga tgtacctgct   151620
caaggcttgg gtggaggcgc tgtcctacac cgaagagcac aaccagcaga tgcgtctgat   151680
ggactatgcg atcgaagtca ctgaaggcat cacacagctt gagaagatcg agcgcaagat   151740
ctggatgtcg ttcctttggg gctgctgtta taacgccatc ggtccatgga caatctacag   151800
tgagttccct gtgcctcctc agtccaaaga agagatgcag cgcttttctg attggtacaa   151860
cctgaacttt gagcgtatgc gcttcgatac cgattgccgt taccgtaagt cgaagatgat   151920
cccgtgtgtt cagtcctaca ttgattggct ggctgggcgt actcagatgg aagcattccg   151980
accgatgctt gaattggata tccctgtcca ccaattcacg aatctgtggg acacggcgat   152040
gtcctggaaa tactttggcc gcctgagcgc ctgaacttc ctggaagccc tgaacatggt   152100
attcggcaac atgtgggaga tcgacgtccc tgggttcatg ctgcgtgacc gcgatggcag   152160
cgagtccaac cgcaacggcg cggcattctt gtcaaaccgt gacgactggg tgaccaagca   152220
cgggaagaaa aagatcaacg gttgtcctat tacagacgaa gaatgtgata tactcgaaac   152280
cgaccttgag aaagcgtttc aggaatgcgt tgaagagttt ggccacatca cgtttatcaa   152340
tcgtctgaac tttgagacct ccggtgcttg ttggctgaag aaattcttcc gactgaagaa   152400
tacccgttac atcgggtggg acgccgagcg tacatgggac gagatcgatt atatggaacg   152460
tatttggcct gaatactcct gtaaggcatt atgggaagcc cgttcactct ggctaccaga   152520
taccctgttg tgcgaaaaag ctcctgcagg gcacgttcct ggcgtccaga gtggaagat   152580
gcctgtgttc tttgagacgg gtgttcctct acatatatgg catttacagc agggtacgcg   152640
ttgggaacca tctgaggttt acactaatct gaaaatgccc gtccgaaaga tagaggacaa   152700
tccgaagtcg accagtgtaa acctcatgtc tttgttgaag cgctgatata aatatcctca   152760
cctataaagt gaggatatta tcatgttaca agatctgttg gtgtacgcgc ttcctggcgt   152820
tgttgtcggc ttcgtagctg gcgctctggt ctttcgtaaa cacgcgcaag acggtgaagt   152880
gattgttcag aagggtaaag acatcctgga acaaatcgaa gccaaactgg acgagctgaa   152940
gaaaaagtaa tctgattgcg attgcgttct tcaataaagg ggaatgggtt attattagcc   153000
cgttccccctt tctttttgca aggattgatt tatgacacct caatacaaaa tattggtcac   153060
cagccgttgt tatgcttatg dacagggtga agcaatatca gtacacacag ttgtagttga   153120
ttttgaaaac aaagaacaag cagatttggc attctataat atgcagcaga gcacagctcc   153180
tgccgatatt ggcgttaaac aagtttatac gaaattatac tgaggtccta tatcatggca   153240
atgcaacgaa ttgaagacat gtctgtgctc gatatggaag cgacatttgg cgactatttt   153300
gaatctaccc cgaaacaaga aaagggtcat ctggtagtgt cggaagagtt cgcacaaaaa   153360
gttcaagata cgcttccgac taaattgaac ggtgggcaag gcggtttccg tcgcggtgaa   153420
ctgaatatca tctgtgccgg agggattacg agatgaagcg ccccgaatac aaacaatatt   153480
tgtacgatct gttcatgaaa gaaacagacg gcgtgttaca tcctaagaaa gcgactattg   153540
ttaaattgca ttctgaaggt gatttgtcta tagcatatat ccgaaaagaa ctcgatttga   153600
tgggaatcga atacgaagac cacatcacgg atacacgtgc tttaaaaaga gaaacagcaa   153660
tcgttcttca taccgttgca acaattatgc atcgccacca tgtttctttt gacgatgcaa   153720
tgactccaca gtatcatgaa gaacgttggg atctgttgtt gaaaaatggg gctaaatctg   153780
```

-continued

```
agcataaaaa tcaacttctt ggtatgacga aggaacaact cgtggatggt gtgttatgat 153840
ttaccttctg tttgtggttc ctgtaatttt ggccatcttg tttataatat atcaccgcaa 153900
gacccatgag ccaaaggaga ctttgatcgc cacggccatt gttatcgtat tgtcttgcct 153960
tatccagtcg ggattatatg ctgctttctc ccttggtagt tctggggacg tggaaatcct 154020
gaatggatat gtaactgata agcaacggaa taaggtgggt tgtgaacatt cttatgaatg 154080
tatgtgttat tacacaacat cttgctctgg ttcaggaaat aaccgatctt gtacacaaac 154140
gcgtcattgc agcacatgct atgagcactc ttatgacgtt gattgggacg tattaacaac 154200
cgtcggtgat ctgagcattg accgtattga tcgtcaggg actacagagc ctccgcgttg 154260
ggcacaagtt aaaatcgggg aacctgcggc acgtgaacat tcatatatga attatgtgct 154320
gggcaacaaa gattcattat tctctaaatc tgaccagcaa ttcgccgaga agttcaaaga 154380
gcatatccct tcatatccga gggtgtatga ttattaccga gtaactcgtg ttctgaatat 154440 gtcaggatg gacattcctg ttgattactg gaatgattat ctgaacaata ctctgaaaac 154500
attaggtgct tcacgtcagg ttaatatcgt ttgggttgtg acttctggcc agcctgttga 154560
atattttcag ggacttctat atgcatggtc tggcggtaaa aagaacgatg ttattgtagt 154620
caccgatatt tcaaaggata tgaaaattaa ttgggggtaag tctacgtcat ttgccgacgg 154680
catgaacaac atggaactcc attctcgtaa cggactttca ttgactggga accaatgggg 154740
catatccgtg ttccaagaag ttgcggtcaa tatcagtaag ggatacaacc gagtcgagat 154800
gaaggaaatg gaatatctga aatggcgaga tcttaaaact tgggaagtga ttatcgtcgt 154860 gttgttttgga tgtatcccat ttaccgcagt tttcatatta ggccgcatgc agtacaatgg 154920
tcgcacttac aaacgtttgt tttaacaaga ggaagtaaag atgtcacaac gtaaaggtat 154980
ttcaattggt tggatcgttg ggttggcaat tctagcattt gctgtaattg ggattggcag 155040
tgtggttagc tatttcaatg atttcaaccg cattgaacaa caggtcaaaa agttcaacaa 155100
agattctgaa aaccacctga gcaactacac gctcaaagtt caggagacgg cgcagattcc 155160
tgacatgtac aaaaacggtt tgaaggaagt gatcaaagat actttccaag gccgttatgg 155220
tgcagacggt tccaaagcag taatgcaatg gattcaggaa cagaatattc agtttgattc 155280
atctttgtac aaagagattc aggttgttat cagctcaggt cgggatgaat tccgcattag 155340
ccaaactaaa aaattggacg catgtgcgat ctatgaaact aaacttggcc agttccctgg 155400
ttctctgata gcaggaatct ttggatatcc gcgtatcgat cttgacaaga catgtcaggt 155460
ggtgagtgac acccgtaccc aggccgcatt tgactctggt gtccagactc cgattaactt 155520
caaaggctga tcttatgagc gtgaaactaa ccgaatctct gacgctggaa cagcaacagg 155580
cgttactgga tgaagtggta atctctgctg tcaagcaggg cattatcaaa gatgacacgt 155640
tgttgacgcg ccccgaaatg atacatcatt tggtggtgtg tctgggcgaa gccaataatc 155700
ctcgcaaaaa gattgtaatg ttcaaagaag gcattattta tcccaacgga agattcgctt 155760
ggttaaccct atcgggaagt catccggatt tgaaggatga acagaaagaa atcaaaactt 155820
ctgttccggt aacgccatac actgaaggag ttgatttatt gtcttggttt gagaccatca 155880
ataccatcta tgtcatggca cctgatgta agccagcaca ggatctgcgt ggtgggttg 155940 taggttcgga agactaataa ttcttcaata aatggggata gggtattatt gctctatccc 156000
cttttcatgg acaagaacat gacagacaag ccaagaaaga tagcgattat tggaggagga 156060
atcggcgctc ggactatggc cattatcctt caagaaaagt tgaaaggtgt tgaagtagaa 156120
```

-continued

```
tgtatcagtg tagacgatat tcctaaacgt cgttgtgaac caggtgaacg catgataatt 156180
tgtgatgatc tggtagaaag tgaacgcaaa acattggtat ctcaagcggt ggctcagtta 156240
cggaaggcag atatttcgta ttgtgaagca gaagccgatg acagagacat aattgcgtca 156300
caacgttatc aaaagccgcc gcgcctatat ggagccgccc aacataaacg tcaggctaag 156360
aaatataaaa atcggagtaa acgaaaatga ctactcaaaa accgacttat gaggaattgg 156420
ccactgcgtt gatccacatg gatgatgcct tccaagatct cttttggccaa gtatgctcta 156480 atccagtgat gaatgcttgg ggcaagcccg ttaactttgc tgttatgaac aaacaccgcg 156540
aacaggcaag ttcaactatt agcaatttgc gtcaaacgat ggatgtaaaa caaccaagca 156600
tccaacggta tcttgaaaac ttcgatgagt attctttcaa agaccttctg ttcaaagatc 156660
tagtcgagca agagcaacgc agacagagta agaactgctc tgaagtacaa tcttctgatg 156720
aaattcgtca gaacatagaa caagaattcg acaatgcata cgatcctatc ggtttggctg 156780
ttatgatcgt aaaagctctg tcgtatgcag caaaaggaga aacaaatgtc taaaccatta 156840
tctgctgcgg ctgtagcaac ccttgctttg tccgccatgg ctgaagatat gacgcataat 156900
ggtcgtctct gggatgatca tcgttatgca caagggtgta cccctgggga acctgggcat 156960
gctcgtcctt ccgtcagtcg tcctaaaaag gccaagaccc atggaaagaa caaaagaaa 157020 cgccgtaaat gatgtcatcc ccgaatatcg ccttcacgca ttatcggaag gtgaacccag 157080
atcatcacga tgtcatgtta tgtttcaaga aggtaaaatg atggccgatg aaatcctctt 157140
ccttcgagca gaggtgatcc gtttaagtaa caataaaccc ccaaagaaat gaggatatgt 157200
catgagttct attgaacagc tgatcacacc acaatatgtt tacagcaata ttgtagagca 157260
cctccgctct caattgaatg tgaagcagtt gaacagctct gaattgagtg gtttagaaat 157320
aacagaagtt gaagttgcgg ccttcggtag tcgttatcat tttgttgtca atcacactca 157380
ggttgaacaa gtcacttcga gcattattga cctcggcgca acgaagcctt cccgcgcaga 157440
gccgaaatct gtgacacgca atattgtggg ttatctggaa gagacgttag agccaggtgc 157500
cacccacccg atattcaatt tcaacgccac cgttgtaaac gttcagggaa gttaatcctg 157560
attaaagcct ccgattggag gcttttctat tgaaccaccc gccagtatca taaccttacc 157620
caataatgtg ttcttctttg atctgaacag gaattctata ct          157662
```